US012357646B2

(12) United States Patent
Garcia et al.

(10) Patent No.: US 12,357,646 B2
(45) Date of Patent: Jul. 15, 2025

(54) CHIMERIC ANTIGEN RECEPTOR T CELL THERAPY

(71) Applicant: Kite Pharma, Inc., Santa Monica, CA (US)

(72) Inventors: Rhine Shen Garcia, Santa Monica, CA (US); Vicki Plaks, Santa Monica, CA (US)

(73) Assignee: Kite Pharma, Inc., Santa Monica, CA (US)

(*) Notice: Subject to any disclaimer, the term of this patent is extended or adjusted under 35 U.S.C. 154(b) by 44 days.

(21) Appl. No.: 17/743,288

(22) Filed: May 12, 2022

(65) Prior Publication Data

US 2022/0378830 A1 Dec. 1, 2022

Related U.S. Application Data

(60) Provisional application No. 63/328,364, filed on Apr. 7, 2022, provisional application No. 63/248,941, filed on Sep. 27, 2021, provisional application No. 63/188,916, filed on May 14, 2021.

(51) Int. Cl.
| | |
|---|---|
| C07K 16/24 | (2006.01) |
| A61K 31/664 | (2006.01) |
| A61K 31/675 | (2006.01) |
| A61K 31/7076 | (2006.01) |
| A61K 40/11 | (2025.01) |
| A61K 40/31 | (2025.01) |
| A61K 40/42 | (2025.01) |
| C07K 16/28 | (2006.01) |
| C12N 5/0783 | (2010.01) |

(52) U.S. Cl.
CPC .......... *A61K 31/675* (2013.01); *A61K 31/664* (2013.01); *A61K 31/7076* (2013.01); *A61K 40/11* (2025.01); *A61K 40/31* (2025.01); *A61K 40/4211* (2025.01); *C07K 16/248* (2013.01); *C07K 16/2803* (2013.01); *C12N 5/0636* (2013.01); *A61K 2239/31* (2023.05); *A61K 2239/38* (2023.05); *A61K 2239/48* (2023.05)

(58) Field of Classification Search
CPC .... A61K 35/17; A61K 31/664; A61K 31/675; A61K 31/7076; A61K 2039/5156; A61K 39/0011; A61K 38/1774; A61K 39/001112; A61K 39/4644; A61K 39/4611; A61K 39/4631; A61K 39/464412; A61K 2239/38; A61K 2239/48; A61K 40/11; A61K 40/31; A61K 40/4211; A61K 2239/31; A61K 40/42; C07K 16/248; C07K 16/2803; C07K 2317/622; C07K 2319/03; C07K 14/7051; C12N 5/0636; C12N 2510/00; A61P 35/02; A61P 35/00
See application file for complete search history.

(56) References Cited

U.S. PATENT DOCUMENTS

| | | | | |
|---|---|---|---|---|
| 9,855,298 | B2 * | 1/2018 | Bot | A61K 38/2053 |
| 10,322,146 | B2 * | 6/2019 | Bot | A61K 31/7076 |
| 10,844,120 | B2 * | 11/2020 | Wiltzius | A61K 39/4631 |
| 11,779,601 | B2 * | 10/2023 | Bot | A61K 39/4611 |
| | | | | 424/93.21 |
| 2015/0283178 | A1 | 10/2015 | June et al. | |

FOREIGN PATENT DOCUMENTS

| | | |
|---|---|---|
| WO | WO-2016/034666 A1 | 3/2016 |
| WO | WO-2018/167486 A1 | 9/2018 |

OTHER PUBLICATIONS

"NHL Subtypes", Leukemia and Lymphoma Society [online]. Retrieved from <https://www.lls.org/lymphoma/non-hodgkin-lymphoma/nhl-subtypes#:~:text=Indolent%20lymphomas%20are%20slow%2Dmoving,common%20subtype%20of%20indolent%20NHL.> Retrieved on: Mar. 6, 2024 (Year: 2024).*
Kingwell K. Nature Reviews Drug Discovery, 16:301-304, 2017 (Year: 2017).*
ClinicalTrials.gov ID No. NCT02625480. First published online on Dec. 8, 2015. (Year: 2015).*
ClinicalTrials.gov ID No. NCT02348216. First published online Jan. 27, 2015. (Year: 2015).*
Hay and Turtle, Drugs, 77(3): 237-24, published Mar. 2017 (Year: 2017).*
ClinicalTrials.gov ID No. NCT02625480 published online on Dec. 13 Retrieved from: <https://clinicaltrials.gov/study/NCT02625480?tab=history&a=24#version-content-panel> Retrieved on Oct. 16, 2024. (Year: 2019).*
clinicaltrials.gov NCT05333302, version 28, published online May 13, 2020.*
Reagan and Friedberg, Future Oncol., 17(11): 1269-1283, published online Jan. 15, 2021.*
Castro, F.V. et al. (2012) "5T4 oncofetal antigen is expressed in high risk of relapse childhood pre-B acute lymphoblastic leukemia and is associated with a more invasive and chemotactic phenotype" Leukemia 26(7):1487-1498.
Maude, S.L. et al. (2018) "Tisagenlecleucel in Children and Young Adults with B-Cell Lymphoblastic Leukemia" N Engl J Med 378(5):439-448.
Owens, G.L. et al. (2018) "Preclinical Assessment of CAR T-Cell Therapy Targeting the Tumor Antigen 5T4 in Ovarian Cancer" J Immunother 41(3):130-140.

(Continued)

*Primary Examiner* — Kimberly Ballard
*Assistant Examiner* — Stacey N Macfarlane

(57) ABSTRACT

The disclosure provides methods of treating a malignancy comprising administering an effective dose of an immune cell therapy (e.g., a chimeric antigen receptor genetically modified T cell immunotherapy) and methods for manufacturing such immunotherapy. Some aspects of the disclosure relate to methods of determining objective response of a patient to an immune cell immunotherapy based on the levels of patient and product attributes prior to and after administration of the immunotherapy to the patient.

4 Claims, 18 Drawing Sheets

Specification includes a Sequence Listing.

(56) References Cited

OTHER PUBLICATIONS

Teachey, D.T. et al. (2018) "Toxicity management after chimeric antigen receptor T cell therapy: one size does not fit 'All'" Nature Reviews Clinical Oncology 15(4):218.

Wayne, A. et al. (2021) "ZUMA-4 phase 1 long-term results: KTE-X19 Car t-cell therapy in children/adolescents with r/r b-all" Pediatric Blood and Cancer R 68:S102 -S103, Retrieved from the Internet: URL:https://onlinelibrary.wiley.com/doi/full-xml/10.1002/pbc.29060>.

Wayne, A.S. et al. (2020) "ZUMA-4: A Phase 1/2 Multicenter Study of KTE-X19 in Pediatric and Adolescent Patients With Relapsed/Refractory B Cell Acute Lymphoblastic Leukemia or Non-Hodgkin Lymphoma" pp. 1-6, Retrieved from the Internet: URL:https://ashpublications.org/blood/article/136/Supplement%201/42/471540/ZUMA-4-A-Phase-1-2-Multicenter-Study-of-KTE-X19-in [retrieved on Oct. 7, 2022].

Invitation to Pay Additional Fees dated Nov. 2, 2022 for PCT/US2022/029047.

Office Action dated Mar. 22, 2023 for Taiwanese Appl. No. 111118020.

Intl. Search Report—Written Opinion dated Dec. 23, 2022 for Intl. Appl. No. PCT/US2022/029047.

Office Action dated Dec. 3, 2024 for Japanese Appl. No. 2023-570138.

* cited by examiner

CHIMERIC ANTIGEN RECEPTOR T CELL THERAPY

CROSS REFERENCE TO RELATED APPLICATIONS

This application claims priority to U.S. Provisional Patent Application No. 63/188,916 filed on May 14, 2021, U.S. Provisional Patent Application No. 63/248,941 filed on Sep. 27, 2021, and U.S. Provisional Patent Application No. 63/328,364 filed on Apr. 7, 2022, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jul. 22, 2022, is named K-1130-US-NP_SL.txt and is 846 bytes in size.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens may be used by the body's innate immune system to specifically target and kill cancer cells. However, cancer cells employ various mechanisms to prevent immune cells, such as T and B lymphocytes, from successfully targeting cancer cells.

Human T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) which comprise binding domains capable of interacting with a particular tumor antigen, allow T cells to target and kill cancer cells that express the particular tumor antigen.

There is a need to understand how attributes of CAR-positive T cells and patients' immunological status correlate with clinical outcomes of immunotherapy.

SUMMARY

Provided herein are methods and uses of cells (e.g., engineered T cells) and/or compositions thereof, for the treatment of subjects having a disease or condition, which generally is or includes a cancer or a tumor, such as a leukemia or a lymphoma. In some aspects, the methods and uses provide for or achieve improved response and/or more durable responses or efficacy and/or a reduced risk of toxicity or other side effects, in subjects treated with some methods, as compared to certain alternative methods. In some embodiments, the methods comprise the administration of specified numbers or relative numbers of the engineered cells, the administration of defined ratios of particular types of the cells, treatment of particular patient populations, such as those having a particular risk profile, staging, and/or prior treatment history, administration of additional therapeutic agents and/or combinations thereof.

Also provided are methods that involve assessing particular parameters, e.g., expression of specific biomarkers or analytes, that may be correlated with an outcome, such as a therapeutic outcome, including a response, such as a complete response (CR) or a partial response (PR); or a safety outcome, such as a development of a toxicity, for example, neurotoxicity or CRS, after administration of a cell therapy. Also provided are methods to assess the likelihood of response and/or likelihood of risk of toxicity, based on assessment of the parameters, such as expression of biomarkers or analytes.

In one aspect, the disclosure provides methods of treatment of cancer expressing a tumor antigen in a subject in need thereof comprising administering to the subject a therapeutically effective amount of CAR T-cells expressing an antigen-binding molecule that recognizes the tumor antigen. In some embodiments, the cancer is a leukemia or lymphoma. In some embodiments, the cancer is mantle cell lymphoma (MCL). In some embodiments, the MCL is relapsed/refractory after ≥2 lines of systemic therapy. In some embodiments, the cancer is (relapsed/refractory) Indolent Non-Hodgkin Lymphoma (iNHL). In some embodiments, the cancer is follicular lymphoma (FL). In some embodiments, the cancer is marginal zone lymphoma (MZL). In some embodiments, the subject has MCL with the high-risk feature of progression within 24 months from initiation of first anti-CD20-containing chemoimmunotherapy (MCL POD24). In some embodiments, the cancer is iNHL with the high-risk feature of progression of disease within 24 months of diagnosis (iNHL POD24). In some embodiments, the tumor antigen is CD19. In some embodiments, the CAR T-cell treatment is administered early. For example, the CAR T-cell treatment may be administered as a first line of therapy and/or prior to progression.

The following embodiments are exemplary of the disclosure and non-limiting:

1. A method of treatment of cancer, Non-Hodgkin Lymphoma (NHL), comprising administering to the subject a therapeutically effective amount of immune cells against a tumor antigen.
2. The method of embodiment 1, wherein the subject is at high-risk of disease progression.
3. The method of embodiment 1 or 2, wherein the NHL is mantle cell lymphoma (MCL) or indolent NHL (iNHL).
4. The method of embodiment 1 or 2, wherein the iNHL is marginal zone lymphoma (MZL) or follicular lymphoma (FL).
5. The method of embodiment 2, wherein the subject is at high-risk if the subject shows progression of disease within 24 months after initial diagnosis.
6. The method of embodiment 2, wherein the subject is at high-risk if the subject shows progression of disease within 24 months from initiation of first anti-CD20-containing chemoimmunotherapy.
7. The method of embodiment 6, wherein the chemoimmunotherapy comprises an alkylating agent.
8. The method of any one of embodiments 1 through 7, wherein the immune cells are administered as a first, second, third, fourth, fifth, or sixth line of therapy.
9. The method of any one of embodiments 1 through 8, wherein the immune cells are selected from tumor-infiltrating lymphocytes (TILs), NK cells, autologous T cells, allogeneic T cells, and engineered autologous T cell (eACT), and any combination thereof.
10. The method of embodiment 9, wherein the immune cells are CAR T cells.
11. The method of embodiment 10, wherein the CAR T cell treatment comprises axicabtagene ciloleucel or brexucabtagene autoleucel/KTE-X19.

12. The method of embodiment 1, 2 or 9, wherein the therapeutically effective amount or effective dose of the immune cells is at least about $10^4$ cells, at least about $10^5$ cells, at least about $10^6$ cells, at least about $10^7$ cells, at least about $10^8$ cells, at least about $10^9$, or at least about $10^{10}$ cells.

13. The method of embodiment 1, 2 or 9, wherein the therapeutically effective amount or effective dose of immune cells is about $10^4$ cells, about $10^5$ cells, about $10^6$ cells, about $10^7$ cells, or about $10^8$ cells.

14. The method of embodiment 1, 2 or 9, wherein the therapeutically effective amount or effective dose of immune cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

15. The method of embodiment 1, 2 or 9, wherein the therapeutically effective amount or effective dose of the immune cells is between about $1\times10^6$ and about $2\times10^6$ immune cells per kg body weight up to a maximum dose of about $1\times10^8$ immune cells.

16. The method of embodiment 1, 2 or 9, wherein the therapeutically effective dose of immune cells is between 75 and $200\times10^6$ immune cells.

17. The method of any one of embodiments 1 through 16, wherein the tumor antigen is selected from a tumor-associated surface antigen, 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, survivin and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gpl20), as well as any derivate or variant of these surface antigens.

18. The method of embodiment 17, wherein the target antigen is CD19.

19. The method of embodiment 1 or 2, wherein the NHL is (relapsed or refractory) diffuse large B-cell lymphoma (DLBCL) not otherwise specified, primary mediastinal large B-cell lymphoma, high grade B-cell lymphoma, or DLBCL arising from follicular lymphoma.

20. The method of any one of embodiments 1 through 19 further comprising preconditioning the subject with one or more preconditioning agents.

21. The method of embodiment 20, wherein the subject is preconditioned with the administration of an alkylating agent and/or platinum-based agent.

22. The method of embodiment 21, wherein the alkylating agents are selected from the group consisting of melphalan, chlorambucil, cyclophosphamide, mechlorethamine, mustine (HN2), uramustine, uracil mustard, melphalan, chlorambucil, ifosfamide, bendamustine, carmustine, lomustine, streptozocin, alkyl sulfonates, busulfan, thiotepa or its analogues, and any combination thereof.

23. The method of embodiment 21, wherein the platinum-based preconditioning agents are selected from the group consisting of platinum, cisplatin, carboplatin, nedaplatin, oxaliplatin, satraplatin, triplatin tetranitrate, procarbazine, altretamine, triazenes, dacarbazine, mitozolomide, temozolomide, dacarbazine, temozolomide, and any combination thereof.

24. The method of embodiment 20, wherein the preconditioning agents comprise cyclophosphamide and fludarabine.

25. The method of any one of embodiments 20 to 24, wherein the administration of the one or more preconditioning agents begins at least seven days, at least six days, at least five days, at least four days, at least three days, at least two days, or at least one day prior to the administration of the cell therapy.

The following additional embodiments are exemplary of the disclosure and non-limiting:

1. A method of treatment of cancer in a subject in need thereof, wherein the cancer is Non-Hodgkin Lymphoma (NHL) or Relapsed/Refractory B-precursor Acute Lymphoblastic Leukemia or Relapsed/Refractory B-Cell Non-Hodgkin Lymphoma (R/R B-ALL), comprising administering to the subject a therapeutically effective amount of immune cells against a tumor antigen; optionally wherein the subject is a pediatric or adolescent subject.

2. The method of claim 1, wherein the subject is at high-risk of disease progression.

3. The method of claim 1 or 2, wherein the NHL is mantle cell lymphoma (MCL) or indolent NHL (iNHL).

4. The method of claim 1 or 2, wherein the iNHL is marginal zone lymphoma (MZL) or follicular lymphoma (FL).

5. The method of claim 2, wherein the subject is at high-risk if the subject shows progression of disease within 24 months after initial diagnosis.

6. The method of claim 2, wherein the subject is at high-risk if the subject shows progression of disease within 24 months from initiation of first anti-CD20-containing chemoimmunotherapy.
7. The method of claim 6, wherein the chemoimmunotherapy comprises an alkylating agent.
8. The method of any one of claims 1 through 7, wherein the immune cells are administered as a first, second, third, fourth, fifth, or sixth line of therapy, and/or prior to disease progression.
9. The method of any one of claims 1 through 8, wherein the immune cells are selected from tumor-infiltrating lymphocytes (TILs), NK cells, autologous T cells, allogeneic T cells, and engineered autologous T cell (eACT), and any combination thereof.
10. The method of claim 9, wherein the immune cells are CAR T cells.
11. The method of claim 10, wherein the CAR T cell treatment comprises axicabtagene ciloleucel or brexucabtagene autoleucel/KTE-X-19.
12. The method of claim 1, 2 or 9, wherein the therapeutically effective amount or effective dose of the immune cells is at least about $10^4$ cells, at least about $10^5$ cells, at least about $10^6$ cells, at least about $10^7$ cells, at least about $10^8$ cells, at least about $10^9$, or at least about $10^{10}$ cells.
13. The method of claim 1, 2 or 9, wherein the therapeutically effective amount or effective dose of immune cells is about $10^4$ cells, about $10^5$ cells, about $10^6$ cells, about $10^7$ cells, or about $10^8$ cells.
14. The method of claim 1, 2 or 9, wherein the therapeutically effective amount or effective dose of immune cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.
15. The method of claim 1, 2 or 9, wherein the therapeutically effective amount or effective dose of the immune cells is between about $1\times10^6$ and about $2\times10^6$ immune cells per kg body weight up to a maximum dose of about $1\times10^8$ immune cells.
16. The method of claim 1, 2 or 9, wherein the therapeutically effective dose of immune cells is between 75 and $200\times10^6$ immune cells.
17. The method of any one of claims 1 through 16, wherein the tumor antigen is selected from a tumor-associated surface antigen, 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, survivin and telomerase, TAG-72, the extra domain A (EDA) and extra domain B (EDB) of fibronectin and the Al domain of tenascin-C (TnC Al), thyroglobulin, tumor stromal antigens, vascular endothelial growth factor receptor-2 (VEGFR2), virus-specific surface antigen such as an HIV-specific antigen (such as HIV gpl20), as well as any derivate or variant of these surface antigens.
18. The method of claim 17, wherein the target antigen is CD19.
19. The method of claim 1 or 2, wherein the NHL is (relapsed or refractory) diffuse large B-cell lymphoma (DLBCL) not otherwise specified, primary mediastinal large B-cell lymphoma, high grade B-cell lymphoma, or DLBCL arising from follicular lymphoma.
20. The method of any one of claims 1 through 19 further comprising preconditioning the subject with one or more preconditioning agents.
21. The method of claim 20, wherein the subject is preconditioned with the administration of an alkylating agent and/or platinum-based agent.
22. The method of claim 21, wherein the alkylating agents are selected from the group consisting of melphalan, chlorambucil, cyclophosphamide, mechlorethamine, mustine (HN2), uramustine, uracil mustard, melphalan, chlorambucil, ifosfamide, bendamustine, carmustine, lomustine, streptozocin, alkyl sulfonates, busulfan, thiotepa or its analogues, and any combination thereof.
23. The method of claim 21, wherein the platinum-based preconditioning agents are selected from the group consisting of platinum, cisplatin, carboplatin, nedaplatin, oxaliplatin, satraplatin, triplatin tetranitrate, procarbazine, altretamine, triazenes, dacarbazine, mitozolomide, temozolomide, dacarbazine, temozolomide, and any combination thereof.
24. The method of claim 20, wherein the preconditioning agents comprise cyclophosphamide and fludarabine.
25. The method of any one of claims 20 to 24, wherein the administration of the one or more preconditioning agents begins at least seven days, at least six days, at least five days, at least four days, at least three days, at least two days, or at least one day prior to the administration of the cell therapy.
26. The method of claim 1, wherein the subject was administered allogeneic Stem Cell Therapy (alloSCT) after treatment with anti-CD19 CAR T-cell therapy.
27. The method of claim 1, wherein the subject has high tumor burden.
28. The method of claim 1, wherein tocilizumab is administered for management of neurologic events only in the context of cytokine release syndrome and/or steroids are initiated for management of grade 2 neurologic events.

The following additional embodiments are exemplary of the disclosure and non-limiting:

An embodiment of the disclosure relates to a method of treating Relapsed/Refractory B-precursor Acute Lymphoblastic Leukemia in a subject including administering to the subject a therapeutically effective amount of immune cells against a tumor antigen, where the subject is a pediatric or adolescent subject.

An embodiment of the disclosure relates to the method above, where the therapeutically effective amount of the immune cells is between about $1 \times 10^6$ and about $2 \times 10^6$ immune cells per kg body weight.

An embodiment of the disclosure relates to the method above, where the immune cells are administered in a total volume of between about 40 ml to 68 ml.

An embodiment of the disclosure relates to the method above, where the immune cells are administered in a total volume of between about 40 ml.

An embodiment of the disclosure relates to the method above, where the therapeutically effective amount of the immune cells is about $1 \times 10^6$ immune cells per kg body weight.

An embodiment of the disclosure relates to the method above, where the immune cells are administered as a first, second, third, fourth, fifth, or sixth line of therapy, or prior to disease progression.

An embodiment of the disclosure relates to the method above, where the tumor antigen is selected from a tumor-associated surface antigen, 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, survivin and telomerase, TAG-72, the extra domain A (EDA) and extra domain B (EDB) of fibronectin and the Al domain of tenascin-C (TnC Al), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface antigens.

An embodiment of the disclosure relates to the method above, where the target antigen is CD19.

An embodiment of the disclosure relates to the method above, further comprising preconditioning the subject with one or more preconditioning agents, where the one or more preconditioning agents are selected from at least one of an alkylating agent and a platinum-based agent, where the alkylating agents are selected from the group consisting of melphalan, chlorambucil, cyclophosphamide, mechlorethamine, mustine (HN2), uramustine, uracil mustard, melphalan, chlorambucil, ifosfamide, bendamustine, carmustine, lomustine, streptozocin, alkyl sulfonates, busulfan, thiotepa or its analogues, and any combination thereof, and where the platinum-based preconditioning agents are selected from the group consisting of platinum, cisplatin, carboplatin, nedaplatin, oxaliplatin, satraplatin, triplatin tetranitrate, procarbazine, altretamine, triazenes, dacarbazine, mitozolomide, temozolomide, dacarbazine, temozolomide, and any combination thereof.

An embodiment of the disclosure relates to the method above, where the preconditioning agents comprise cyclophosphamide and fludarabine.

An embodiment of the disclosure relates to the method above, where the cyclophosphamide is administered at a dose of between 200 mg/m$^2$/day and 2000 mg/m$^2$/day, and where the fludarabine is administered at a dose of between 20 mg/m$^2$/day and 900 mg/m$^2$/day.

An embodiment of the disclosure relates to the method above, where the administration of the one or more preconditioning agents begins at least seven days, at least six days, at least five days, at least four days, at least three days, at least two days, or at least one day prior to the administration of the immune cells.

An embodiment of the disclosure relates to the method above, where the subject has a high tumor burden.

An embodiment of the disclosure relates to the method above, further comprising at least one of administering tocilizumab for management of a neurologic event only in the context of cytokine release syndrome, and administering a corticosteroid for management of a grade 2 neurologic event.

An embodiment of the disclosure relates to the method above, where the subject is at high-risk of disease progression, where the subject is at high-risk if the subject shows progression of disease within 24 months after initial diagnosis.

An embodiment of the disclosure relates to the method above, where the immune cells are selected from tumor-infiltrating lymphocytes (TILs), NK cells, autologous T cells, allogeneic T cells, and engineered autologous T cell (eACT), and any combination thereof.

An embodiment of the disclosure relates to the method above, where the immune cells are CAR T cells.

An embodiment of the disclosure relates a method of treating cancer in a subject in need thereof, where the cancer is Non-Hodgkin Lymphoma (NHL) or Relapsed/Refractory B-precursor Acute Lymphoblastic Leukemia or Relapsed/Refractory B-Cell Non-Hodgkin Lymphoma (R/R B-ALL), comprising administering to the subject a therapeutically effective amount of immune cells against a tumor antigen, and where the immune cells are autologous T cells expressing an anti-CD19 chimeric antigen receptor (CAR).

An embodiment of the disclosure relates to the method above, where the cancer is NHL and the NHL is mantle cell lymphoma (MCL) or indolent NHL (iNHL).

An embodiment of the disclosure relates to the method above, where the iNHL is marginal zone lymphoma (MZL) or follicular lymphoma (FL).

An embodiment of the disclosure relates to the method above, where the cancer is NHL and the NHL is (relapsed or refractory) diffuse large B-cell lymphoma (DLBCL) not otherwise specified, primary mediastinal large B-cell lymphoma, high grade B-cell lymphoma, or DLBCL arising from follicular lymphoma.

DETAILED DESCRIPTION

Definitions

Figure 1:
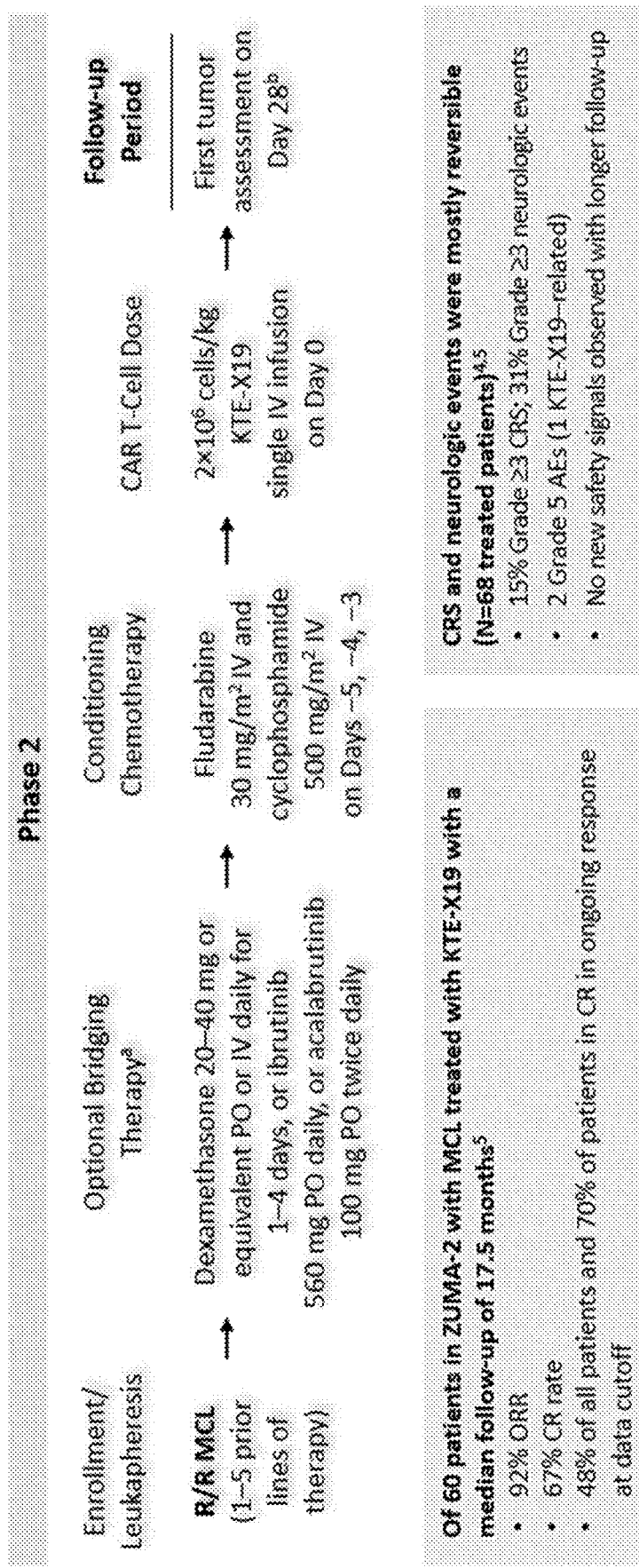
FIG. 1. Design of CLINICAL TRIAL-2 Clinical Trial. a Administered after leukapheresis and completed ≥5 days before initiating conditioning chemotherapy; PET-CT was required postbridging. b Bone marrow biopsy was to be done at screening, and if positive, not done, or if indeterminate, a biopsy was needed to confirm CR. AE, adverse event; CAR, chimeric antigen receptor; CR, complete response; CRS, cytokine release syndrome; IV, intravenous; MCL, mantle cell lymphoma; ORR, objective response rate; PO, oral; R/R, relapsed/refractory.

For the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e.," as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided. The term "consisting of" excludes any element, step, or ingredient not specified in the claim. In re Gray, 53 F.2d 520, 11 USPQ 255 (CCPA 1931); Ex parte Davis, 80 USPQ 448, 450 (Bd. App. 1948) ("consisting of" defined as "closing the claim to the inclusion of materials other than those recited except for impurities ordinarily associated therewith"). The term "consisting essentially of" limits the scope of a claim to the specified materials or steps "and those that do not materially affect the basic and novel characteristic(s)" of the claimed invention.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" may mean within one or more than one standard deviation per the practice in the art. "About" or "approximately" may mean a range of up to 10% (i.e., ±10%). Thus, "about" may be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg may include any amount between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. Exemplary routes of administration for the compositions disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering may also be performed, for example, once, a plurality of times, and/or over one or more extended periods. In one embodiment, the CAR T cell treatment is administered via an "infusion product" comprising CAR T cells.

The term "antibody" (Ab) includes, without limitation, a glycoprotein immunoglobulin which binds specifically to an antigen. In general, an antibody may comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies may include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to CD19. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e., expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocks a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

In one embodiment, the CAR T cell treatment comprises "axicabtagene ciloleucel treatment". "Axicabtagene ciloleucel treatment" consists of a single infusion of anti-CD19 CAR transduced autologous T cells administered intravenously at a target dose of $2\times10^6$ anti-CD19 CAR T cells/kg. For subjects weighing greater than 100 kg, a maximum flat dose of $2\times10^8$ anti-CD19 CAR T cells may be administered. The anti-CD19 CAR T cells are autologous human T cells that have been engineered to express an extracellular single-chain variable fragment (scFv) with specificity for CD19 linked to an intracellular signaling part comprised of signaling domains from CD28 and CD3ζ (CD3-zeta) molecules arranged in tandem anti-CD19 CAR vector construct has been designed, optimized and initially tested at the Surgery Branch of the National Cancer Institute (NCI, IND 13871) (Kochenderfer et al, *J Immunother.* 2009; 32(7):689-702; Kochenderfer et al, *Blood.* 2010; 116(19):3875-86). The scFv is derived from the variable region of the anti-CD19 monoclonal antibody FMC63 (Nicholson et al, *Molecular Immunology.* 1997; 34(16-17):1157-65). A portion of the CD28 costimulatory molecule is added, as murine models suggest this is important for the anti-tumor effect and persistence of anti-CD19 CAR T cells (Kowolik et al, *Cancer Res.* 2006; 66(22):10995-1004). The signaling domain of the CD3-zeta chain is used for T cell activation. These fragments were cloned into the murine stem cell virus-based (MSGV1) vector, utilized to genetically engineer the autologous T cells. The CAR construct is inserted into the T cells' genome by retroviral vector transduction. Briefly, peripheral blood mononuclear cells (PBMCs) are obtained by leukapheresis and Ficoll separation. Peripheral blood mononuclear cells are activated by culturing with an anti-CD3 antibody in the presence of recombinant interleukin 2 (IL-2). Stimulated cells are transduced with a retroviral vector containing an anti-CD19 CAR gene and propagated in culture to generate sufficient engineered T cells for administration. Axicabtagene ciloleucel is a subject-specific product.

In one embodiment, the CAR T cell treatment comprises KTE-X19, an autologous anti-CD19 chimeric antigen receptor (CAR) T-cell therapy that is approved in the United States and European Union for the treatment of relapsed/refractory (R/R) MCL. (TECARTUS® (brexucabtagene autoleucel) Prescribing information. Kite Pharma, Inc; 2021; TECARTUS® (autologous anti-CD19-transduced CD3+ cells) Summary of product characteristics. Kite Pharma EU B.V.; 2021). The manufacturing process of KTE-X19 was modified relative to that of axicabtagene ciloleucel to remove circulating lymphoma cells through positive enrichment for $CD4^+/CD8^+$ cells.

In one embodiment, the products are characterized in terms of cellular composition. Cells may be labeled with fluorescently-conjugated antibodies to CD3 (pan T cell marker), CD14, CD19 (B cell marker), CD45 (pan-leukocyte marker), and CD56 (activation and NK marker) and assessed by flow cytometry. Cell viability may be assessed using negative staining of a viability dye (SYTOX near-IR). The lower limit of quantification (LLOQ) of the assay may be 0.2% and for NK cells and monocytes was 5%. The percentage of NK cells may be determined (NK cells were $CD45^+$, $CD14^-$, $CD3^-$, and $CD56^+$; T cells were $CD45^+$, $CD14^-$, and $CD3^-$). The median percentages of NK cells from 23 lots of axicabtagene ciloleucel and 97 lots of KTE-X19 may be 1.9% (range 0.8%-3.2%) and 0.1% (range 0.0%-2.8%), respectively. The median percentage of $CD3^-$ cellular impurities from the same lots of axicabtagene ciloleucel and KTE-X19 may be 2.4% (range 0.9%-4.6%) and 0.5% (range 0.3%-3.9%), respectively. The results of KTE-X19 (brexucabtagene autoleucel, TECARTUS) and axicabtagene ciloleucel (YESCARTA) in cell viability may be ≥72% and ≥80%, respectively; in anti-CD19 CAR expression may be ≥24% and ≥15%, respectively; in IFN-γ production may be ≥190 pg/mL and ≥520 pg/mL, respectively; and in percentage of $CD3^+$ cells may be ≥90% and ≥85%, respectively. Brexucabtagene autoleucel may be predominantly composed of CD3+ T cells (99.3%±0.8%), which may be further delineated into the CD4+ (37.9%±16.5%) and CD8+ (59.3%±16.5%) subsets.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. In this application, the term cancer is synonymous with malignancy. Examples of cancers that may be treated by the methods disclosed herein include, but are not limited to, cancers of the immune system including lymphoma, leukemia, myeloma, and other leukocyte malignancies. In some embodiments, the methods disclosed herein may be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, and combinations of said cancers. In some embodiments, the cancer is multiple myeloma. In some embodiments, the cancer is NHL. The particular cancer may be responsive to chemo- or radiation therapy or the cancer may be refractory. A refractory cancer refers to a cancer that is not amenable to surgical intervention and the cancer is either initially unresponsive to chemo- or radiation therapy or the cancer becomes unresponsive over time.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, B cells, T cells, and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response.

Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

As used herein, "chimeric receptor" refers to an engineered surface expressed molecule capable of recognizing a particular molecule. Chimeric antigen receptors (CARs) and engineered T cell receptors (TCRs), which comprise binding domains capable of interacting with a particular tumor antigen, allow T cells to target and kill cancer cells that express the particular tumor antigen. In one embodiment, the T cell treatment is based on T cells engineered to express a chimeric antigen receptor (CAR) or a T cell receptor (TCR), which comprises (i) an antigen binding molecule, (ii) a costimulatory domain, and (iii) an activating domain. The costimulatory domain may comprise an extracellular domain, a transmembrane domain, and an intracellular domain, wherein the extracellular domain comprises a hinge domain, which may be truncated.

A "therapeutically effective amount," "effective dose," "effective amount," or "therapeutically effective dosage" of a therapeutic agent, e.g., engineered CAR T cells, small molecules, "agents" described in the specification, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. Such terms may be used interchangeably. The ability of a therapeutic agent to promote disease regression may be evaluated using a variety of methods known to the skilled practitioner, such as in human subjects during clinical trials, in animal model systems predictive of efficacy in humans, or by assaying the activity of the agent in in vitro assays. Therapeutically effective amounts and dosage regimens may be determined empirically by testing in known in vitro or in vivo (e.g., animal model) systems.

The term "combination" refers to either a fixed combination in one dosage unit form, or a combined administration where a compound of the present disclosure and a combination partner (e.g., another drug as explained below, also referred to as "therapeutic agent" or "agent") may be administered independently at the same time or separately within time intervals, especially where these time intervals allow that the combination partners show a cooperative, e.g., synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time.

The terms "product" or "infusion product" are used interchangeably herein and refer to the T cell composition that is administered to the subject in need thereof. Typically, in CAR T-cell therapy, the T cell composition is administered as an infusion product.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory TSCM cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

In the context of this disclosure, the term "TN," "T naïve-like", and CCR7+CD45RA+ actually refers to cells that are more like stem-like memory cells than like canonical naïve T cells. Accordingly, all references in the Examples and Claims to $T_N$ refers to cells that were experimentally selected only by their characterization as CCR7+CD45RA+ cells and should be interpreted as such. Their better name in the context of this disclosure is stem-like memory cells, but they shall be referred to as CCR7+CD45RA+ cells. Further characterization into stem-like memory cells may be done for example using the methods described in Arihara Y, Jacobsen C A, Armand P, et al. *Journal for ImmunoTherapy of Cancer.* 2019; 7(1):P210.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy may include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. Nos. 7,741,465, 6,319,494, 5,728,388, and International Publication No. WO 2008/081035. In some embodiments, the immunotherapy comprises CAR T cell treatment. In some embodiments, the CAR T cell treatment product is administered via infusion.

The T cells of the immunotherapy may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by reference in its entirety.

The term "engineered Autologous Cell Therapy," or "eACT™," also known as adoptive cell transfer, is a process by which a patient's own T cells are collected and subsequently genetically altered to recognize and target one or more antigens expressed on the cell surface of one or more specific tumor cells or malignancies. T cells may be engineered to express, for example, chimeric antigen receptors (CAR). CAR positive (+) T cells are engineered to express an extracellular single chain variable fragment (scFv) with specificity for a particular tumor antigen linked to an intracellular signaling part comprising at least one costimulatory domain and at least one activating domain. The CAR scFv may be designed to target, for example, CD19, which is a transmembrane protein expressed by cells in the B cell lineage, including all normal B cells and B cell malignances, including but not limited to diffuse large B-cell lymphoma (DLBCL) not otherwise specified, primary mediastinal large B-cell lymphoma, high grade B-cell lymphoma, and DLBCL arising from follicular lymphoma, NHL, CLL, and non-T cell ALL. Example CAR T cell therapies and constructs are described in U.S. Patent Publication Nos. 2013/0287748, 2014/0227237, 2014/0099309, and 2014/0050708, and these references are incorporated by reference in their entirety.

A "patient" or a "subject" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell may include a T cell. The term "in vivo" means within the patient.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that may comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex that specifically binds with a cognate stimulatory ligand present on an antigen present cell. A "stimulatory ligand" is a ligand that when present on an antigen presenting cell (e.g., an APC, a dendritic cell, a B-cell, and the like) may specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody, an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. In certain embodiments, a co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD33, CD45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD11a, CD11b, CD11c, CD11d, CDS, CEACAM1, CRT AM, DAP-10, DNAM1 (CD226), Fc gamma receptor, GADS, GITR, HVEM (LIGHTR), IA4, ICAM-1, ICOS, Ig alpha (CD79a), IL2R beta, IL2R gamma, IL7R alpha, integrin, ITGA4, ITGA6, ITGAD, ITGAE, ITGAL, ITGAM, ITGAX, ITGB2, ITGB7, ITGB1, KIRDS2, LAT, LFA-1, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions. Similarly, the term "increasing" indicates any change that is higher than the original value. "Increasing," "higher," and "lower" are relative terms, requiring a comparison between pre- and post-measurements and/or between reference standards. In some embodiments, the reference values are obtained from those of a general population, which could be a general population of patients. In some embodiments, the reference values come quartile analysis of a general patient population.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In some embodiments, "treatment" or "treating" includes a partial remission. In another embodiment, "treatment" or "treating" includes a complete remission. In some embodiments, the treatment may be prophylactic, in which case the treatment is administered before any symptoms of the condition are observed. The term "prophylaxis" as used herein means the prevention of or protective treatment for a disease or disease state. Prevention of a symptom, disease, or disease state may include reduction (e.g., mitigation) of one or more symptoms of the disease or disease state, e.g., relative to a reference level (e.g., the symptom(s) in a similar subject not administered the treatment). Prevention may also include delaying onset of one or more symptoms of the disease or disease state, e.g., relative to a reference level (e.g., the onset of the symptom(s) in a similar subject not administered the treatment). In embodiments, a disease is a disease described herein. In some embodiments, the disease is cancer. In some embodiments, the diseased state is CRS or neurotoxicity. In some embodiments, indicators of improvement or successful treatment include determination of the failure to manifest a relevant score on toxicity grading scale (e.g., CRS or neurotoxicity grading scale), such as a score of less than 3, or a change in grading or severity on the grading scale as discussed herein, such as a change from a score of 4 to a score of 3, or a change from a score of 4 to a score of 2, 1 or 0.

As used herein, the term "polyfunctional T cells" refers to cells co-secreting at least two proteins from a pre-specified panel per cell coupled with the amount of each protein produced (i.e., combination of number of proteins secreted and at what intensity). In some embodiments, a single cell functional profile is determined for each evaluable population of engineered T cells. Profiles may be categorized into effector (Granzyme B, IFN-γ, MIP-1α, Perforin, TNF-α, TNF-β), stimulatory (GM-CSF, IL-2, IL-5, IL-7, IL-8, IL-9, IL-12, IL-15, IL-21), regulatory (IL-4, IL-10, IL-13, IL-22, TGF-β1, sCD137, sCD40L), chemoattractive (CCL-11, IP-10, MIP-1β, RANTES), and inflammatory (IL-1b, IL-6, IL-17A, IL-17F, MCP-1, MCP-4) groups. In some embodiments, the functional profile of each cell enables the calculation of other metrics, including a breakdown of each sample according to cell polyfunctionality (i.e., what percentage of cells are secreting multiple cytokines versus non-secreting or monofunctional cells), and a breakdown of the sample by functional groups (i.e., which mono- and polyfunctional groups are being secreted by cells in the sample, and their frequency).

As used herein, "myeloid cells" are a subgroup of leukocytes that includes granulocytes, monocytes, macrophages, and dendritic cells.

As used herein, the term "quartile" is a statistical term describing a division of observations into four defined intervals based upon the values of the data and how they compare to the entire set of observations.

As used herein, the term "Study day 0" is defined as the day the subject received the first CAR T cell infusion. The day prior to study day 0 will be study day −1. Any days after enrollment and prior to study day −1 will be sequential and negative integer-valued.

As used herein, the term "durable response" refers to the subjects who were in ongoing response at least by one year follow up post CAR T cell infusion. In one embodiment, "duration of response" (DOR) is defined only for subjects who experience an objective response and is the time from the first objective response to disease progression per (Cheson et al, 2014) or disease-related death, whichever comes first.

As used herein, the term "relapse" refers to the subjects who achieved a complete response (CR) or partial response (PR) and subsequently experienced disease progression.

As used herein, the term "non-response" refers to the subjects who had never experienced CR or PR post CAR T cell infusion.

As used herein, the term "objective response" refers to complete response (CR), partial response (PR), or non-response. It may be assessed per revised IWG Response Criteria for Malignant Lymphoma (Cheson et al., *J Clin Oncol.* 2007; 25(5):579-86).

As used herein, the term "complete response" refers to complete resolution of disease, which becomes not detectable by radio-imaging and clinical laboratory evaluation. No evidence of cancer at a given time.

As used herein, the term "partial response" refers to a reduction of greater than 30% of tumor without complete resolution.

As used herein "objective response rate" (ORR) is determine per International Working Group (IWG) 2007 criteria (Cheson et al. J Clin Oncol. 2007; 25(5):579-86).

As used herein "progression-free survival (PFS)" may be defined as the time from the T cell infusion date to the date of disease progression or death from any cause. Progression is defined per investigator's assessment of response as defined by IWG criteria (Cheson et al., *J Clin Oncol.* 2007; 25(5):579-86).

The term "overall survival (OS)" may be defined as the time from the T cell infusion date to the date of death from any cause.

As used herein, the expansion and persistence of CAR T cells in peripheral blood may be monitored by qPCR analysis, for example using CAR-specific primers for the scFv portion of the CAR (e.g., heavy chain of a CD19 binding domain) and its hinge/CD28 transmembrane domain. Alternatively, it may be measured by enumerating CAR cells/unit of blood volume.

As used herein, the scheduled blood draw for CAR T cells may be before CAR T cell infusion, Day 7, Week 2 (Day 14), Week 4 (Day 28), Month 3 (Day 90), Month 6 (Day 180), Month 12 (Day 360), and Month 24 (Day 720).

As used herein, the "peak of CAR T cell" is defined as the maximum absolute number of CAR+ PBMC/µL in serum attained after Day 0.

As used herein, the "time to Peak of CAR T cell" is defined as the number of days from Day 0 to the day when the peak of CAR T cell is attained.

As used herein, the "Area Under Curve (AUC) of level of CAR T cell from Day 0 to Day 28" is defined as the area under the curve in a plot of levels of CAR T cells against scheduled visits from Day 0 to Day 28. This AUC measures the total levels of CAR T cells overtime.

As used herein, the scheduled blood draw for cytokines is before or on the day of conditioning chemotherapy (Day −5), Day 0, Day 1, Day 3, Day 5, Day 7, every other day if any through hospitalization, Week 2 (Day 14), and Week 4 (Day 28).

As used herein, the "baseline" of cytokines is defined as the last value measured prior to conditioning chemotherapy.

As used herein, the fold change from baseline at Day X is defined as $$\frac{\text{Cytokine level at Day } X - \text{Baseline}}{\text{Baseline}}$$

As used herein, the "peak of cytokine post baseline" is defined as the maximum level of cytokine in serum attained after baseline (Day −5) up to Day 28.

As used herein, the "time to peak of cytokine" post CAR T cell infusion is defined as the number of days from Day 0 to the day when the peak of cytokine was attained.

As used herein, the "Area Under Curve (AUC) of cytokine levels" from Day −5 to Day 28 is defined as the area under the curve in a plot of levels of cytokine against scheduled visits from Day −5 to Day 28. This AUC measures the total levels of cytokine overtime. Given the cytokine and CAR+ T cell are measured at certain discrete time points, the trapezoidal rule may be used to estimate the AUCs.

As used herein, treatment-emergent adverse events (TE-AEs) are defined as adverse events (AE) with onset on or after the first dose of conditioning chemotherapy. Adverse events may be coded with the Medical Dictionary for Regulatory Activities (MedDRA) version 22.0 and graded using the National Cancer Institute (NCI) Common Terminology Criteria for Adverse Events (CTCAE) version 4.03. Cytokine Release Syndrome (CRS) events may be graded on the syndrome level per Lee and colleagues (Lee et al, 2014 *Blood.* 2014; 124(2):188-95. Individual CRS symptoms may be graded per CTCAE 4.03. Neurologic events may be identified with a search strategy based on known neurologic toxicities associated with CAR T immunotherapy, as described in, for example, Topp, M S et al. *Lancet Oncology.* 2015; 16(1):57-66.

Various aspects of the disclosure are described in further detail in the following subsections.

Pre-Treatment Attributes

Pre-treatment attributes of the apheresis and immune cells (also referred to herewith as engineered cells such as T cell) and patient immune factors measured from a patient sample may be used to assess the probability of clinical outcomes including response and toxicity. Attributes associated with clinical outcomes may be tumor related parameters (e.g., tumor burden, serum LDH as hypoxic/cell death marker, inflammatory markers associated with tumor burden and myeloid cell activity), T cell attributes (e.g., T cell fitness, functionality especially T1 related IFNgamma production, and the total number of CD8 T cells infused) and CAR T cell engraftment measured by peak CAR T cell levels in blood at early time points.

Information extrapolated from T cell attributes and patient pre-treatment attributes may be used to determine, refine or prepare a therapeutically effective dose suitable for treating a malignancy (e.g., cancer). Furthermore, some T cell attributes and patient pre-treatment attributes may be used to determine whether a patient will develop adverse events after treatment with an engineered chimeric antigen receptor (CAR) immunotherapy (e.g., neurotoxicity (NT), cytokine release syndrome (CRS)). Accordingly, an effective adverse event management strategy may be determined (e.g., administration of tocilizumab, a corticosteroid therapy, or an anti-seizure medicine for toxicity prophylaxis based on the measured levels of the one or more attributes).

In some embodiments, the pre-treatment attributes are attributes of the engineered T cells comprising one or more chimeric antigen receptors. In some embodiments, the pre-treatment attributes are T cell transduction rate, major T cell phenotype, numbers of CAR T cells and T cell subsets, fitness of CAR T cells, T cell functionality, T cell polyfunctionality, number of differentiated CAR+CD8+ T cells, number of CCR7+CD45RA+ T cells, CD4/CD8 ratio, IFN-γ in coculture).

In some embodiments, the pre-treatment attributes are measured from a sample obtained from the patient (e.g., cerebrospinal fluid (CSF), blood, serum, or tissue biopsy). In some embodiments, the one or more pre-treatment attributes is tumor burden, levels of IL-6, or levels of LDH.

T Cell Fitness

In some embodiments, the intrinsic cell fitness is assessed based on the capacity of the CAR T cells to expand during nonspecific stimulation in vitro (e.g., shorter doubling time), the differentiation state of the CAR T cells (favorable juvenile phenotype), the levels of specialized CAR T-cell subsets in the CAR T-cell population (e.g., the numbers of CD8 and naïve-like CD8 cells (e.g., CD8+ CCR7+ CD45RA+ T Cells) in the infusion product), and the in vivo CAR T cell expansion rate.

In one embodiment, T cell fitness is the capability of cells to rapidly expand. In the context of engineered T cells, in one embodiment, T cell fitness is a measurement of how fast the engineered T cell population expand pre-treatment. As described herein, T cell fitness is an attribute of engineered T cells that associates with clinical outcome. In some embodiments, T cell fitness is measured by doubling time or expansion rate. An exemplary derivation of T cell "fitness" measured as T cell population doubling time (DT) during the manufacturing process is shown below.

$$\text{Doubling Time} = \frac{\ln(2) \times \text{duration}}{\ln\left(\frac{\text{total viable cells at harvest}}{\text{total viable cells at Day 3}}\right)}$$

Duration may be defined as total manufacturing timeframe MINUS three days (essentially the number of days for the product cells in culture post transduction and before harvest and cryopreservation). Recombinant IL-2 (after nonspecific stimulation with, for example, anti-CD3 antibodies) may be used to drive polyclonal T cell expansion towards achieving the target dose. The shorter the DT, the higher engineered T cell fitness. In vitro expansion rate may be calculated using the formula below.

Expansion rate=ln(2)/Doubling Time

In the instances described above, the expansion rate is provided in units of "rate/day" or "/day."

In some embodiments, in vivo expansion rate is measured by enumerating CAR cells/unit of blood volume. In some embodiments, the in vivo expansion rate is measured by the number of CAR gene copies/µg of host DNA. In some embodiments, the in vivo expansion rate is measured by of enumerating CAR cells/unit of blood volume.

As described herein, higher peak expansion of CAR T cells in the peripheral blood, generally occurring within 2 weeks of post-CAR T-cell infusion, may associate with both objective response and durable response, defined as ongoing response with a minimum follow-up of 1 year. Peak number of CAR T cells in the blood correlated with response. Cumulative CAR T-cell levels over the first 28 days, as measured in blood by area under the curve (AUC), may also associate with better objective and durable response to therapy. In some embodiments, the CAR T-cell levels are calculated by enumerating the number of CAR T-cells per unit of blood volume. In one embodiment, higher peak expansion of CAR T cells in the peripheral blood means peak expansion values falling within the higher quartiles. In some embodiments, in vivo expansion rate is measured by enumerating CAR cells/unit of blood volume. In some embodiments, the in vivo expansion rate is measured by the number of CAR gene copies/µg of host DNA.

As described herein, the intrinsic capability of T-cell expansion measured pretreatment, as measured by product doubling time, is a major attribute of product T-cell fitness. Relative to other product characteristics, DT was most strongly associated with the frequency of T-cell differentiation subsets in the final infusion bag. Specifically, DT was positively associated with the frequency of effector memory T (TEM) cells and negatively associated with the frequency of naïve-like T (TN) cells. In one embodiment (e.g., axicabtagene ciloleucel), the $T_N$ cells that are identified as CCR7+CD45RA+ cells are actually stem-like memory cells and not canonical naïve T cells. As described herein, baseline tumor burden is positively associated with the differentiation phenotype in the final infusion product. As described herein, product composition and clinical performance associate with the pretreatment immune status of the patient. Accordingly, in one embodiment, the disclosure provides a method of reducing post-treatment tumor burden with treatment with CAR T cells comprising administering an infusion product comprising increased frequency of naïve-like T (TN) cells in the infusion product relative to a reference value. In another embodiment, the disclosure provides a method to predict or estimate the differentiation phenotype of the final infusion product comprising measuring the baseline tumor burden in the patient to obtain a value and estimating or predicting the differentiation phenotype based on the value. In one embodiment, the measure further comprises preparing an effective dose of CAR T cells in the final product based on the value.

T Cell Phenotypes

As described herein, the T cell phenotypes in manufacturing starting material (apheresis) may be associated with T cell fitness (DT). Total % of Tn-like and Tcm cells (CCR7+ cells) is inversely related to DT. The % of Tem (CCR7− CD45RA−) cells is directly associated with DT. Accordingly, in some embodiments, the pre-treatment attribute is the % of Tn-like and Tcm cells. In some embodiments, the % of Tn-like and Tcm cells is determined by the percentage of CCR7+ cells. In some embodiments, the percentage of CCR7+ cells is measured by flow cytometry.

In some embodiments, the pre-treatment attribute is the % of Tem (CCR7−CD45RA−) cells. In some embodiments, the % of Tem cells is determined by the percentage of CCR7− CD45RA− cells. In some embodiments, the percentage of CCR7− CD45RA− cells is measured by flow cytometry.

As described herein, the greater the proportions of effector memory T cells in the apheresis product, within total CD3+ T cells or CD4 and CD8 subsets, the higher the product doubling time. As described herein, the more juvenile the T-cell phenotype in the starting material but better the product T-cell fitness. As described herein, CD27+CD28+ $T_N$ cells, which represent immunologically competent subset of $T_N$ cells that express costimulatory molecules, associate positively with product doubling time. As described herein, there is a direct association across all major phenotypic groups, including proportions of T-cell subsets defined by differentiation markers in CD3, CD4, and CD8 subpopulations, in the apheresis product relative to the final product phenotype. As described herein, the proportion of T cells with $CD25^{hi}$ CD4 expression, possibly representing regulatory T cells in the apheresis material, negatively correlates with the CD8 T-cell output in the product. As described herein, tumor burden after CAR T cell treatment is positively associated with the differentiation phenotype of the final product.

T1 Functionality

Engineered T cells may be characterized by their immune function characteristics. Methods of the present disclosure provide measuring levels of cytokine production ex vivo. In some embodiments, the cytokines are selected from the group consisting of IFNgamma, TNFa, IL-12, MIP1β, MIP1α, IL-2, IL-4, IL-5, and IL-13. In some embodiments, the T cell functionality is measured by levels of Th1 cytokines.

In some embodiments, the Th1 cytokines are selected from the group consisting of IFNgamma, TNFa, and IL-12. In some embodiments, T cell functionality is measured by levels of IFNgamma production. In some embodiments, excess T cell IFNgamma (pre-treatment attribute), and post-treatment T1 activity, are attributes that may be used to determine whether a patient will develop adverse events (e.g., neurotoxicity). In some embodiments, IFNgamma levels produced by engineered CAR T cells are measured by co-culture prior to administration of engineered CAR T cells.

Other Immune Cell Product Characteristics

In some embodiments, the immune cell product administered to the subject has several other product characteristics that are related to its efficacy. In some embodiments, the product characteristics are selected from: Total number of CAR T-cells per μL, Total Number of T-cells per μL, Transduction Rate, %, IFN-γ level, pg/mL, Viability, %, CD4/CD8 ratio; Naive (CCR7+CD45RA+) T cells; %, Central memory (CCR7+CD45RA−) T cells; %, $(T_N+T_{CM})/(T_{EM}+T_{EFF})$ ratio ($T_{CM}$, central memory T cell; $T_{EFF}$, effector T cell; $T_{EM}$, effector memory T cell; $T_N$, naive T cell).

Chimeric Antigen Receptors

Chimeric antigen receptors (CARs) are genetically engineered receptors. These engineered receptors may be inserted into and expressed by immune cells, including T cells and other lymphocytes in accordance with techniques known in the art. With a CAR, a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell. Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci. Transl. Med. 3:95 (2011); Porter et al., N. Engl. J. Med. 365:725-33 (2011), and Gross et al., Annu. Rev. Pharmacol. Toxicol. 56:59-83 (2016).

In some embodiments, a costimulatory domain which includes a truncated hinge domain ("THD") further comprises some or all of a member of the immunoglobulin family such as IgG1, IgG2, IgG3, IgG4, IgA, IgD, IgE, IgM, or fragment thereof.

In some embodiments, the THD is derived from a human complete hinge domain ("CHD"). In other embodiments, the THD is derived from a rodent, murine, or primate (e.g., non-human primate) CHD of a costimulatory protein. In some embodiments, the THD is derived from a chimeric CHD of a costimulatory protein.

The costimulatory domain for the CAR of the disclosure may further comprise a transmembrane domain and/or an intracellular signaling domain. The transmembrane domain may be fused to the extracellular domain of the CAR. The costimulatory domain may similarly be fused to the intracellular domain of the CAR. In some embodiments, the transmembrane domain that naturally is associated with one of the domains in a CAR is used. In some instances, the transmembrane domain is selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Transmembrane regions of particular use in this disclosure may be derived from (i.e., comprise) 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD3 zeta, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1; CD11a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

Optionally, short linkers may form linkages between any or some of the extracellular, transmembrane, and intracellular domains of the CAR. In some embodiments, the linker may be derived from repeats of glycine-glycine-glycine-glycine-serine (SEQ ID NO: 2) (G4S)n or GST-SGSGKPGSGEGSTKG (SEQ ID NO: 1). In some embodiments, the linker comprises 3-20 amino acids and an amino acid sequence at least 80%, 81%, 82%, 83%, 84%, 85%, 86%, 87%, 88%, 89%, 90%, 91%, 92%, 93%, 94%, 95%, 96%, 97%, 98%, 99% or 100% identical to GST-SGSGKPGSGEGSTKG (SEQ ID NO: 1).

The linkers described herein, may also be used as a peptide tag. The linker peptide sequence may be of any appropriate length to connect one or more proteins of interest and is preferably designed to be sufficiently flexible so as to allow the proper folding and/or function and/or activity of one or both of the peptides it connects. Thus, the linker peptide may have a length of no more than 10, no more than 11, no more than 12, no more than 13, no more than 14, no more than 15, no more than 16, no more than 17, no more than 18, no more than 19, or no more than 20 amino acids. In some embodiments, the linker peptide comprises a length of at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids. In some embodiments, the linker comprises at least 7 and no more than 20 amino acids, at least 7 and no more than 19 amino acids, at least 7 and no more than 18 amino acids, at least 7 and no more than 17 amino acids, at least 7 and no more than 16 amino acids, at least 7 and no more 15 amino acids, at least 7 and no more than 14 amino acids, at least 7 and no more than 13 amino acids, at least 7 and no more than 12 amino acids or at least 7 and no more than 11 amino acids. In certain embodiments, the linker comprises 15-17 amino acids, and in particular embodiments, comprises 16 amino acids. In some embodiments, the linker comprises 10-20 amino acids. In some embodiments, the linker comprises 14-19 amino acids. In some embodiments, the linker comprises 15-17 amino acids. In some embodiments, the linker comprises 15-16 amino acids. In some embodiments, the linker comprises 16 amino acids. In some embodiments, the linker comprises 3, 4, 5, 6, 7, 8, 9, 10, 11, 12, 13, 14, 15, 16, 17, 18, 19 or 20 amino acids.

In some embodiments, a spacer domain is used. In some embodiments, the spacer domain is derived from CD4, CD8a, CD8b, CD28, CD28T, 4-1BB, or other molecule described herein. In some embodiments, the spacer domains may include a chemically induced dimerizer to control expression upon addition of a small molecule. In some embodiments, a spacer is not used.

The intracellular (signaling) domain of the engineered T cells of the disclosure may provide signaling to an activating domain, which then activates at least one of the normal effector functions of the immune cell. Effector function of a T cell, for example, may be cytolytic activity or helper activity including the secretion of cytokines.

In certain embodiments, suitable intracellular signaling domain include (i.e., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), integrins, ITGA4, ITGA6, ITGAD, ITGAE, ITGAL, ITGAM, ITGAX, ITGB2, ITGB7, ITGB1, KIRDS2, LAT, ligand that specifically binds with CD83, LIGHT, LTBR, Ly9 (CD229), Ly108), lymphocyte function-associated antigen-1 (LFA-1; CD11a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

Antigen Binding Molecules

Suitable CARs may bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment ("scFv"). A scFv is a single chain antibody fragment having the variable regions of the heavy and light chains of an antibody linked together. See U.S. Pat. Nos. 7,741,465 and 6,319,494, as well as Eshhar et al., Cancer Immunol Immunotherapy (1997) 45: 131-136. A scFv retains the parent antibody's ability to interact specifically with target antigen. scFv's are useful in chimeric antigen receptors because they may be engineered to be expressed as part of a single chain along with the other CAR components. Id. See also Krause et al., J. Exp. Med., Volume 188, No. 4, 1998 (619-626); Finney et al., *Journal of Immunology*, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the disclosure, with specificity to more than one target of interest.

In some embodiments, the polynucleotide encodes a CAR comprising a (truncated) hinge domain and an antigen binding molecule that specifically binds to a target antigen. In some embodiments, the target antigen is a tumor antigen. In some embodiments, the antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CS-1, CSPG4, CTLA-4, DLL3, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, MN-CA IX, MUC-1, mut hsp70-2, mutated p53, mutated ras, neutrophil elastase, NKG2D, Nkp30, NY-ESO-1, p53, PAP, prostase, prostate specific antigen (PSA), prostate-carcinoma tumor antigen-1 (PCTA-1), prostate-specific antigen protein, STEAP1, STEAP2, PSMA, RAGE-1, ROR1, RU1, RU2 (AS), surface adhesion molecule, surviving and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface antigens.

The present disclosure is further illustrated by the following examples, which should not be construed as further limiting. The disclosures provided by this application may be used in a variety of methods in additional to, or as a combination of, the methods described above. The following is a compilation of exemplary methods that may be derived from the disclosures provided in this application.

Engineered Immune Cells and Uses

In one embodiment, the cells of the present disclosure may be obtained through T cells obtained from a subject. T cells may be obtained from, e.g., peripheral blood mononuclear cells, bone marrow, lymph node tissue, cord blood, thymus tissue, tissue from a site of infection, ascites, pleural effusion, spleen tissue, tumors, or differentiated in vitro. In addition, the T cells may be derived from one or more T cell lines available in the art. T cells may also be obtained from a unit of blood collected from a subject using any number of techniques known to the skilled artisan, such as FICOLL™ separation and/or apheresis. In some embodiments, the cells collected by apheresis are washed to remove the plasma fraction, and placed in an appropriate buffer or media for subsequent processing. In some embodiments, the cells are washed with PBS. As will be appreciated, a washing step may be used, such as by using a semi-automated flow through centrifuge, e.g., the Cobe™ 2991 cell processor, the Baxter CytoMate™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Pub. No. 2013/0287748, which is herein incorporated by references in its entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection may be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected may be used. For example, to enrich for CD4+ cells by negative selection, a monoclonal antibody cocktail typically includes antibodies to CD8, CD11b, CD14, CD16, CD20, and HLA-DR. In some embodiments, flow cytometry and cell sorting are used to isolate cell populations of interest for use in the present disclosure.

In some embodiments, PBMCs are used directly for genetic modification with the immune cells (such as CARs) using methods as described herein. In some embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, CD8+ cells are further sorted into naive, central memory, and effector cells by identifying cell surface antigens that are associated with each of these types of CD8+ cells. In some embodiments, the expression of phenotypic markers of central memory T cells includes expression of CCR7, CD3, CD28, CD45RO, CD62L, and CD127 and negative for granzyme B. In some embodiments, central memory T cells are CD8+, CD45RO+, and CD62L+ T cells. In some embodiments, effector T cells are negative for CCR7, CD28, CD62L, and CD127 and positive for granzyme B and perforin. In some embodiments, CD4+ T cells are further sorted into subpopulations. For example, CD4+ T helper cells may be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is the Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety. In some embodiments, the T cells are obtained from a donor subject. In some embodiments, the donor subject is human patient afflicted with a cancer or a tumor. In some embodiments, the donor subject is a human patient not afflicted with a cancer or a tumor.

In one embodiment, the disclosure provides a method of manufacturing an immunotherapy product with improved clinical efficacy and/or decreased toxicity. In some embodiments, the immunotherapy product comprises blood cells. In some embodiments, blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some embodiments, a washing step is accomplished a semi-automated "flow-through" centrifuge (for example, the Cobe 2991 cell processor, Baxter) according to the manufacturer's instructions. In some embodiments, a washing step is accomplished by tangential flow filtration (TFF) according to the manufacturer's instructions. In some embodiments, the cells are resuspended in a variety of biocompatible buffers after washing, such as, for example, Ca++Mg++free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient. In some embodiments, the methods include leukapheresis.

In some embodiments, at least a portion of the selection step includes incubation of cells with a selection reagent. The incubation with a selection reagent or reagents, e.g., as part of selection methods which may be performed using one or more selection reagents for selection of one or more different cell types based on the expression or presence in or on the cell of one or more specific molecules, such as surface markers, e.g., surface proteins, intracellular markers, or nucleic acid. In some embodiments, any known method using a selection reagent or reagents for separation based on such markers may be used. In some embodiments, the selection reagent or reagents result in a separation that is affinity- or immunoaffinity-based separation. For example, the selection in some embodiments includes incubation with a reagent or reagents for separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

In some embodiments of such processes, a volume of cells is mixed with an amount of a desired affinity-based selection reagent. The immunoaffinity-based selection may be carried out using any system or method that results in a favorable energetic interaction between the cells being separated and the molecule specifically binding to the marker on the cell, e.g., the antibody or other binding partner on the solid surface, e.g., particle. In some embodiments, methods are carried out using particles such as beads, e.g., magnetic beads, that are coated with a selection agent (e.g., antibody) specific to the marker of the cells. The particles (e.g., beads) may be incubated or mixed with cells in a container, such as a tube or bag, while shaking or mixing, with a constant cell density-to-particle (e.g., bead) ratio to aid in promoting energetically favored interactions. In other cases, the methods include selection of cells in which all or a portion of the selection is carried out in the internal cavity of a chamber, for example, under centrifugal rotation. In some embodiments, incubation of cells with selection reagents, such as immunoaffinity-based selection reagents, is performed in a chamber.

In some embodiments, by conducting such selection steps or portions thereof (e.g., incubation with antibody-coated particles, e.g., magnetic beads) in the cavity of a chamber, the user is able to control certain parameters, such as volume of various solutions, addition of solution during processing and timing thereof, which may provide advantages compared to other available methods. For example, the ability to decrease the liquid volume in the cavity during the incubation may increase the concentration of the particles (e.g., bead reagent) used in the selection, and thus the chemical potential of the solution, without affecting the total number of cells in the cavity. This in turn may enhance the pairwise interactions between the cells being processed and the particles used for selection. In some embodiments, carrying out the incubation step in the chamber, e.g., when associated with the systems, circuitry, and control as described herein, permits the user to effect agitation of the solution at desired time(s) during the incubation, which also may improve the interaction.

In some embodiments, at least a portion of the selection step is performed in a chamber, which includes incubation of cells with a selection reagent. In some embodiments of such processes, a volume of cells is mixed with an amount of a desired affinity-based selection reagent that is far less than is normally employed when performing similar selections in a tube or container for selection of the same number of cells and/or volume of cells according to manufacturer's instructions. In some embodiments, an amount of selection reagent or reagents that is/are no more than 5%, no more than 10%, no more than 15%, no more than 20%, no more than 25%, no more than 50%, no more than 60%, no more than 70% or no more than 80% of the amount of the same selection reagent(s) employed for selection of cells in a tube or container-based incubation for the same number of cells and/or the same volume of cells according to manufacturer's instructions is employed.

In some embodiments, for selection, e.g., immunoaffinity-based selection of the cells, the cells are incubated in the chamber in a composition that also contains the selection buffer with a selection reagent, such as a molecule that specifically binds to a surface marker on a cell that it desired to enrich and/or deplete, but not on other cells in the composition, such as an antibody, which optionally is coupled to a scaffold such as a polymer or surface, e.g., bead, e.g., magnetic bead, such as magnetic beads coupled to monoclonal antibodies specific for CD4 and CD8. In some embodiments, as described, the selection reagent is added to cells in the cavity of the chamber in an amount that is substantially less than (e.g., is no more than 5%, 10%, 20%, 30%, 40%, 50%, 60%, 70% or 80% of the amount) as compared to the amount of the selection reagent that is typically used or would be necessary to achieve about the same or similar efficiency of selection of the same number of cells or the same volume of cells when selection is performed in a tube with shaking or rotation. In some embodiments, the incubation is performed with the addition of a selection buffer to the cells and selection reagent to achieve a target volume with incubation of the reagent of, for example, 10 mL to 200 mL, such as at least or about at least 10 mL, 20 mL, 30 mL, 40 mL, 50 mL, 60 mL, 70 mL, 80 mL, 90 mL, 100 mL, 150 mL or 200 mL. In some embodiments, the selection buffer and selection reagent are pre-mixed before addition to the cells. In some embodiments, the selection buffer and selection reagent are separately added to the cells. In some embodiments, the selection incubation is carried out with periodic gentle mixing condition, which may aid in promoting energetically favored interactions and thereby permit the use of less overall selection reagent while achieving a high selection efficiency. In some embodiments, the total duration of the incubation with the selection reagent is from or from about 5 minutes to 6 hours, such as 30 minutes to 3 hours, for example, at least or about at least 30 minutes, 60 minutes, 120 minutes or 180 minutes.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g., at or about or at least 600 rpm, 1000 rpm, or 1500 rpm or 1700 rpm), such as at an RCF at the sample or wall of the chamber or other container of from or from about 80 g to 100 g (e.g., at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, such process is carried out within the entirely closed system to which the chamber is integral. In some embodiments, this process (and in some embodiments also one or more additional step, such as a previous wash step washing a sample containing the cells, such as an apheresis sample) is carried out in an automated fashion, such that the cells, reagent, and other components are drawn into and pushed out of the chamber at appropriate times and centrifugation effected, so as to complete the wash and binding step in a single closed system using an automated program.

In some embodiments, after the incubation and/or mixing of the cells and selection reagent and/or reagents, the incubated cells are subjected to a separation to select for cells based on the presence or absence of the particular reagent or reagents. In some embodiments, the separation is performed in the same closed system in which the incubation of cells with the selection reagent was performed. In some embodiments, after incubation with the selection reagents, incubated cells, including cells in which the selection reagent has bound are transferred into a system for immunoaffinity-based separation of the cells. In some embodiments, the system for immunoaffinity-based separation is or contains a magnetic separation column.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some embodiments includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner. Such separation steps may be based on positive selection, in which the cells having bound the reagents are retained for further use, and/or negative selection, in which the cells having not bound to the antibody or binding partner are retained. In some examples, both fractions are retained for further use.

In some embodiments, negative selection may be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step may deplete cells expressing multiple markers simultaneously, such as by incubating cells with a plurality of antibodies or binding partners, each specific for a marker targeted for negative selection. Likewise, multiple cell types may simultaneously be positively selected by incubating cells with a plurality of antibodies or binding partners expressed on the various cell types.

For example, in some embodiments, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+T cells, are isolated by positive or negative selection techniques. For example, CD3+, CD28+T cells may be positively selected using anti-CD3/anti-CD28 conjugated magnetic beads (e.g., DYNABEADS® M-450 CD3/CD28 T Cell Expander). In some embodiments, the population of cells is enriched for T cells with naïve phenotype (CD45RA+ CCR7+).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (markerhlgh) on the positively or negatively selected cells, respectively.

In particular embodiments, a biological sample, e.g., a sample of PBMCs or other white blood cells, are subjected to selection of CD4+ T cells, where both the negative and positive fractions are retained. In certain embodiments, CD8+ T cells are selected from the negative fraction. In some embodiments, a biological sample is subjected to selection of CD8+ T cells, where both the negative and positive fractions are retained. In certain embodiments, CD4+ T cells are selected from the negative fraction.

In some embodiments, T cells are separated from a PBMC sample by negative selection of markers expressed on non-T cells, such as B cells, monocytes, or other white blood cells, such as CD14. In some embodiments, a CD4+ or CD8+ selection step is used to separate CD4+ helper and CD8+ cytotoxic T cells. Such CD4+ and CD8+ populations may be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long term survival, expansion, and/or engraftment following administration, which in some embodiments is particularly robust in such sub-populations. In some embodiments, combining TcM-enriched CD8+ T cells and CD4+T cells further enhances efficacy. In some embodiments, enriching for T cells with naïve phenotype (CD45RA+ CCR7+) enhances efficacy. In embodiments, memory T cells are present in both CD62L+ and CD62L subsets of CD8+ peripheral blood lymphocytes. PBMC may be enriched for or depleted of CD62L CD8+ and/or CD62L+CD8+ fractions, such as using anti-CD8 and anti-CD62L antibodies.

In some embodiments, the enrichment for central memory T (TCM) cells is based on positive or high surface expression of CD45RO, CD62L, CCR7, CD28, CD3, and/or CD127; in some embodiments, it is based on negative selection for cells expressing or highly expressing CD45RA and/or granzyme B. In some embodiments, isolation of a CD8+ population enriched for TCM cells is carried out by depletion of cells expressing CD4, CD 14, CD45RA, and positive selection or enrichment for cells expressing CD62L. In one embodiment, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some embodiments are carried out simultaneously and in other embodiments are carried out sequentially, in either order. In some embodiments, the same CD4 expression-based selection step used in preparing the CD8+ cell population or subpopulation, also is used to generate the CD4+ cell population or subpopulation, such that both the positive and negative fractions from the CD4-based separation are retained and used in subsequent steps of the methods, optionally following one or more further positive or negative selection steps. In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+ T helper cells are sorted into naive, central memory, and effector cells by identifying cell populations that have cell surface antigens. CD4+ lymphocytes may be obtained by standard methods. In some embodiments, naive CD4+T lymphocytes are CD45RO, CD45RA+, CD62L+, CD4+ T cells. In some embodiments, central memory CD4+ cells are CD62L+ and CD45RO+. In some embodiments, effector CD4+ cells are CD62L and CD45RO. In some embodiments, T cells with naïve phenotype are CD45RA+ CCR7+.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques. In some embodiments, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample. In some embodiments, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some embodiments, a combination of positive and negative selection is performed during the same selection step, where the positive and negative fractions are retained and further processed or subject to further separation steps. In some embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies. In some embodiments, the magnetically responsive particles are left attached to the cells that are to be subsequently incubated, cultured and/or engineered; in some embodiments, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they may be eluted and recovered. In certain embodiments, the non-target cells are labelled and depleted from the heterogeneous population of cells.

In some embodiments, the isolation or separation is carried out using a system, device, or apparatus that carries out one or more of the isolation, cell preparation, separation, processing, incubation, culture, and/or formulation steps of the methods. In some embodiments, the system is used to carry out each of these steps in a closed or sterile environment, for example, to minimize error, user handling and/or contamination. In one example, the system is a system as described in International Patent Application, Publication Number WO2009/072003, or US 20110003380 A1. In some embodiments, the system or apparatus carries out one or more, e.g., ah, of the isolation, processing, engineering, and formulation steps in an integrated or self-contained system, and/or in an automated or programmable fashion. In some embodiments, the system or apparatus includes a computer and/or computer program in communication with the system or apparatus, which allows a user to program, control, assess the outcome of, and/or adjust various embodiments of the processing, isolation, engineering, and formulation steps. In some embodiments, the separation and/or other steps is carried out using CliniMACS system (Miltenyi Biotec), for example, for automated separation of cells on a clinical-scale level in a closed and sterile system. Components may include an integrated microcomputer, magnetic separation unit, peristaltic pump, and various pinch valves. The integrated computer in some embodiments controls ah components of the instrument and directs the system to perform repeated procedures in a standardized sequence. The magnetic separation unit in some embodiments includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some embodiments uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some embodiments is equipped with a cell processing unity that permits automated washing and fractionation of cells by centrifugation. The CliniMACS Prodigy system may also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system may also include an integrated cell cultivation chamber which accomplishes cell culture protocols such as, e.g., cell differentiation and expansion, antigen loading, and long-term cell culture. Input ports may allow for the sterile removal and replenishment of media and cells may be monitored using an integrated microscope.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376. In both cases, cells may be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some embodiments may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the isolation and/or selection results in one or more input compositions of enriched T cells, e.g., CD3+ T cells, CD4+ T cells, and/or CD8+ T cells. In some embodiments, two or more separate input composition are isolated, selected, enriched, or obtained from a single biological sample. In some embodiments, separate input compositions are isolated, selected, enriched, and/or obtained from separate biological samples collected, taken, and/or obtained from the same subject.

In certain embodiments, the one or more input compositions is or includes a composition of enriched T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD3+ T cells. In one embodiment, the input composition of enriched T cells consists essentially of CD3+ T cells.

In certain embodiments, the one or more input compositions is or includes a composition of enriched CD4+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD4+ T cells. In certain embodiments, the input composition of CD4+ T cells includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells. In some embodiments, the composition of enriched T cells consists essentially of CD4+ T cells.

In certain embodiments, the one or more compositions is or includes a composition of CD8+ T cells that is or includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In certain embodiments, the composition of CD8+ T cells contains less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free of or substantially free of CD4+ T cells. In some embodiments, the composition of enriched T cells consists essentially of CD8+ T cells.

In some embodiments, the cells are incubated and/or cultured prior to or in connection with genetic engineering. The incubation steps may include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions may include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of stimulating or activating an intracellular signaling domain of a TCR complex. In some embodiments, the agent turns on or initiates TCR/CD3 intracellular signaling cascade in a T cell. Such agents may include antibodies, such as those specific for a TCR, e.g., anti-CD3. In some embodiments, the stimulating conditions include one or more agent, e.g., ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/mL). In some embodiments, the stimulating agents include IL-2, IL-15 and/or IL-7. In some embodiments, the IL-2 concentration is at least about 10 units/mL. In some embodiments, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g., for a time sufficient to expand the numbers of T cells). In some embodiments, the non-dividing feeder cells may comprise gamma-irradiated PBMC feeder cells. In some embodiments, the PBMC are irradiated with gamma rays in the range of about 3000 to 3600 rads to prevent cell division. In some embodiments, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL may be irradiated with gamma rays in the range of about 6000 to 10,000 rads.

The LCL feeder cells in some embodiments is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naive or antigen specific T lymphocytes with antigen. for example, antigen-specific T cell lines or clones may be generated to cytomegalovirus antigens by isolating T cells from infected subjects and stimulating the cells in vitro with the same antigen.

In some embodiments, at least a portion of the incubation in the presence of one or more stimulating conditions or a stimulatory agents is carried out in the internal cavity of a centrifugal chamber, for example, under centrifugal rotation, such as described in International Publication Number WO2016/073602. In some embodiments, at least a portion of the incubation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some embodiments of such processes, a volume of cells is mixed with an amount of one or more stimulating conditions or agents that is far less than is normally employed when performing similar stimulations in a cell culture plate or other system.

In some embodiments, the stimulating agent is added to cells in the cavity of the chamber in an amount that is substantially less than (e.g., is no more than 5%, 10%, 20%, 30%, 40%, 50%, 60%, 70% or 80% of the amount) as compared to the amount of the stimulating agent that is typically used or would be necessary to achieve about the same or similar efficiency of selection of the same number of cells or the same volume of cells when selection is performed without mixing in a chamber, e.g., in a tube or bag with periodic shaking or rotation. In some embodiments, the incubation is performed with the addition of an incubation buffer to the cells and stimulating agent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL or 200 mL. In some embodiments, the incubation buffer and stimulating agent are pre-mixed before addition to the cells. In some embodiments, the incubation buffer and stimulating agent are separately added to the cells. In some embodiments, the stimulating incubation is carried out with periodic gentle mixing condition, which may aid in promoting energetically favored interactions and thereby permit the use of less overall stimulating agent while achieving stimulating and activation of cells.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g., at or about or at least 600 rpm, 1000 rpm, or 1500 rpm or 1700 rpm), such as at an RCF at the sample or wall of the chamber or other container of from or from about 80 g to 100 g (e.g., at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, the total duration of the incubation, e.g., with the stimulating agent, is between or between about 1 hour and 96 hours, 1 hour and 72 hours, 1 hour and 48 hours, 4 hours and 36 hours, 8 hours and 30 hours or 12 hours and 24 hours, such as at least or about at least 6 hours, 12 hours, 18 hours, 24 hours, 36 hours or 72 hours. In some embodiments, the further incubation is for a time between or about between 1 hour and 48 hours, 4 hours and 36 hours, 8 hours and 30 hours or 12 hours and 24 hours, inclusive.

In some embodiments, the stimulating conditions include incubating, culturing, and/or cultivating a composition of enriched T cells with and/or in the presence of one or more cytokines. In particular embodiments, the one or more cytokines are recombinant cytokines. In some embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the stimulation results in activation and/or proliferation of the cells, for example, prior to transduction.

In some embodiments, engineered cells, such as T cells, used in connection with the provided methods, uses, articles of manufacture or compositions are cells have been genetically engineered to express a recombinant receptor, e.g., a CAR or a TCR described herein. In some embodiments, the cells are engineered by introduction, delivery or transfer of nucleic acid sequences that encode the recombinant receptor and/or other molecules. In some embodiments, methods for producing engineered cells includes the introduction of a polynucleotide encoding a recombinant receptor (e.g., anti-CD19 CAR) into a cell, e.g., such as a stimulated or activated cell. In particular embodiments, the recombinant proteins are recombinant receptors, such as any described. Introduction of the nucleic acid molecules encoding the recombinant protein, such as recombinant receptor, in the cell may be carried out using any of a number of known vectors. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation. In some embodiments, the engineering produces one or more engineered compositions of enriched T cells.

In certain embodiments, the one or more compositions of stimulated T cells are or include two separate stimulated compositions of enriched T cells. In some embodiments, two separate compositions of enriched T cells, e.g., two separate compositions of enriched T cells that have been selected, isolated, and/or enriched from the same biological sample, are separately engineered. In certain embodiments, the two separate compositions include a composition of enriched CD4+ T cells. In some embodiments, the two separate compositions include a composition of enriched CD8+ T cells. In some embodiments, two separate compositions of enriched CD4+ T cells and enriched CD8+ T cells are genetically engineered separately. In some embodiments, the same composition is enriched for both CD4+ T cells and CD8+ T cells and these are genetically engineered together.

In some embodiments, a composition comprising engineered T cells comprises a pharmaceutically acceptable carrier, diluent, solubilizer, emulsifier, preservative and/or adjuvant. In some embodiments, the composition comprises an excipient. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some embodiments, the composition is selected for parenteral delivery, for inhalation, or for delivery through the digestive tract, such as orally. The preparation of such pharmaceutically acceptable compositions is within the ability of one skilled in the art. In some embodiments, buffers are used to maintain the composition at physiological pH or at a slightly lower pH, typically within a pH range of from about 5 to about 8. In some embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In some embodiments, the vehicle for parenteral injection is sterile distilled water in which composition described herein, with or without at least one additional therapeutic agent, is formulated as a sterile, isotonic solution, properly preserved. In some embodiments, the preparation involves the formulation of the desired molecule with polymeric compounds (such as polylactic acid or polyglycolic acid), beads or liposomes, that provide for the controlled or sustained release of the product, which are then be delivered via a depot injection. In some embodiments, implantable drug delivery devices are used to introduce the desired molecule.

In some embodiments, the methods of treating a cancer in a subject in need thereof comprise a T cell therapy. In some embodiments, the T cell therapy disclosed herein is engineered Autologous Cell Therapy (eACT™). According to this embodiment, the method may include collecting blood cells from the patient. The isolated blood cells (e.g., T cells) may then be engineered to express a CAR disclosed herein. In a particular embodiment, the CAR T cells are administered to the patient. In some embodiments, the CAR T cells treat a tumor or a cancer in the patient. In some embodiments the CAR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient. In certain embodiments, the T cell is a tumor-infiltrating lymphocyte (TIL), engineered autologous T cell (eACT™), an allogeneic T cell, a heterologous T cell, or any combination thereof.

In some embodiments, the engineered T cells are administered at a therapeutically effective amount. For example, a therapeutically effective amount of the engineered T cells may be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4 \times 10^7$ cells/kg, about $5 \times 10^7$ cells/kg, about $6 \times 10^7$ cells/kg, about $7 \times 10^7$ cells/kg, about $8 \times 10^7$ cells/kg, or about $9 \times 10^7$ cells/kg.

In some embodiments, the therapeutically effective amount of the engineered viable T cells is between about $1 \times 10^6$ and about $2 \times 10^6$ engineered viable T cells per kg body weight up to a maximum dose of about $1 \times 10^8$ engineered viable T cells. In some embodiments, the engineered T cells are anti-CD19 CART T cells. In some embodiments, the anti-CD19 CAR T cells are the axicabtagene ciloleucel product. In some embodiments, the anti-CD19 CART cells are the brexucabtagene autoleucel product, also known as KTE-X19.

Methods of Treatment

The methods disclosed herein may be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In some embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In some embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma (MCL), Marginal zone lymphoma (MZL), monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, Waldenstrom macroglobulinemia, or a combination thereof.

In some embodiments, the cancer is a myeloma. In some embodiments, the cancer is multiple myeloma. In some embodiments, the cancer is leukemia. In some embodiments, the cancer is acute myeloid leukemia.

In some embodiments, the cancer is Non-Hodgkin lymphoma. In some embodiments, the cancer is relapsed/refractory NHL. In some embodiments, the cancer is mantle cell lymphoma.

In some embodiments, the cancer is advanced-stage indolent non-Hodgkin lymphoma (iNHL), including follicular lymphoma (FL) and marginal zone lymphoma (MZL). In some embodiments, the patient has had relapsed/refractory disease after ≥2 prior lines of therapy, including an anti-CD20 monoclonal antibody with an alkylating agent. In some embodiments, the patient may have received a PI3K inhibitor. In some embodiments, the patient may (also) have received autologous stem cell transplantation. In some embodiments, the patient undergoes leukapheresis to obtain T cells for CAR T cell manufacturing, followed by conditioning chemotherapy with cyclophosphamide at 500 mg/m²/day and fludarabine at 30 mg/m²/day administered on days −5, −4, and −3; on day 0, the patient may receive a single intravenous infusion of CAR T cell therapy (e.g., axicabtagene ciloleucel) at a target dose of $2 \times 10^6$ CAR T cells/kg. In some embodiments, additional infusions may be given at a later period. In some embodiments, if the patient progresses after responding at the month 3 assessment after initial administration, the patient may receive retreatment with CAR T cell treatment (e.g., axicabtagene ciloleucel). In some embodiments, the patient may receive bridging therapy. Examples of bridging therapies include dexamethasone, Rituximab, Etoposide, Carboplatin, Ifosfamide, Bendamustine-rituximab, Bendamustine, Methylprednisolone, Mitoxantrone, cyclophosphamide, fludarabine, ibrutinib. In some embodiments, the patient experiences CRS. In some embodiments, CRS is managed using any one of the protocols described in this application, including the Examples. In some embodiments, CRS is managed with tocilizumab, corticosteroids and/or vasopressor.

In some embodiments, the cancer is relapsed/refractory indolent Non-Hodgkin Lymphoma and the method of treating a subject in need thereof comprises administering to the subject a therapeutically effective amount of CAR T cells as a retreatment, wherein the subject has previously received a first treatment with CAR T cells. In some embodiments, the first treatment with CAR T cells may have been administered as a first line therapy or a second line therapy, optionally wherein the lymphoma is R/R follicular lymphoma (FL) or marginal zone lymphoma (MZL) and optionally wherein the previous prior lines of therapy included anti-CD20 monoclonal antibody combined with an alkylating agent. In some embodiments, the conditioning therapy comprises fludarabine 30 mg/m² IV and cyclophosphamide 500 mg/m² IV on Days −5, −4, and −3. In some embodiments, the CAR T cell treatment comprises single IV infusion of $2 \times 10^6$ CAR T cells/kg on Day 0. In some embodiments, at least about $10^4$ cells, at least about $10^5$ cells, at least about $10^6$ cells, at least about $10^7$ cells, at least about $10^8$ cells, at least about $10^9$, or at least about $10^{10}$ CAR T cells are administered. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the T cells is about $2 \times 10^6$ cells/kg, about $3 \times 10^6$ cells/kg, about $4 \times 10^6$ cells/kg, about $5 \times 10^6$ cells/kg, about $6 \times 10^6$ cells/kg, about $7 \times 10^6$ cells/kg, about $8 \times 10^6$ cells/kg, about $9 \times 10^6$ cells/kg, about $1 \times 10^7$ cells/kg, about $2 \times 10^7$ cells/kg, about $3 \times 10^7$ cells/kg, about $4 \times 10^7$ cells/kg, about $5 \times 10^7$ cells/kg, about $6 \times 10^7$ cells/kg, about $7 \times 10^7$ cells/kg, about $8 \times 10^7$ cells/kg, or about $9 \times 10^7$ cells/kg In some embodiments, the CAR T cells are anti-CD19 CAR T cells. In some embodiments, the CAR T cells are axicabtagene ciloleucel CAR T cells. In some embodiments, the CAR T cells are brexucabtagene autoleucel/KTE-X19. In some embodiments, the retreatment eligibility criteria include response of a CR or PR at the month 3 disease assessment with subsequent progression; no evidence of CD19 loss in progression biopsy by local review; and/or no Grade 4 CRS or neurologic events, or life-threatening toxicities with the first treatment with CAR T cells. In some embodiments, the method of treatment is that followed by the CLINICAL TRIAL-2 clinical trial (NCT02601313). In some embodiments, the method of treatment is that followed by the CLINICAL TRIAL-5 clinical trial (NCT03105336). In some embodiments, the method of treatment is that followed by the CLINICAL TRIAL-1 (NCT02348216) clinical trial, which has been described in detail in Neelapu, S S et al. 2017, *N Engl J Med* 2017; 377(26):2531-44) and Locke, et al. *Lancet Oncol.* 2019; 20:31-42.

In some embodiments, the cancer is NHL and the CAR T cell treatment is administered as a first line therapy. In some embodiments, the cancer is LBCL. In some embodiments, the LBCL is high risk/high grade LBCL with MYC and BCL2 and/or BCL6 translocations or DLBCL with IPI score≥3 any time before enrollment. In some embodiments, the first line therapy comprises CAR T cell treatment in combination with an anti-CD20 monoclonal antibody and anthracycline-containing regimen. In some embodiments, the CAR T cell treatment is administered first. In some embodiments, the anti-CD20 monoclonal antibody/anthracycline-containing regimen is administered first. In some embodiments, the treatments are administered at least 2 weeks, at least 4 weeks, at least 6 weeks, at least 1 month, at least 2 months, at least 3 months, at least 4 months, at least 5 months, less than a year apart, etc. In some embodiments, the method further comprises bridging therapy administered after leukapheresis and completed prior to initiating conditioning chemotherapy. In some embodiments, additional inclusion criteria include age≥18 years and ECOG PS 0-1. In some embodiments, the conditioning therapy comprises fludarabine 30 mg/m$^2$ IV and cyclophosphamide 500 mg/m$^2$ IV on Days −5, −4, and −3. Other exemplary beneficial preconditioning treatment regimens are described in U.S. Provisional Patent Applications 62/262,143 and 62/167,750 and U.S. Pat. Nos. 9,855,298 and 10,322,146, which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient. Another embodiment comprises serum cyclophosphamide and fludarabine at days −4, −3, and −2 prior to T cell administration at a dose of 500 mg/m$^2$ of body surface area of cyclophosphamide per day and a dose of 30 mg/m$^2$ of body surface area per day of fludarabine during that period of time. Another embodiment comprises cyclophosphamide at day −2 and fludarabine at days −4, −3, and −2 prior to T cell administration, at a dose of 900 mg/m$^2$ of body surface area of cyclophosphamide and a dose of 25 mg/m$^2$ of body surface area per day of fludarabine during that period of time. In another embodiment, the conditioning comprises cyclophosphamide and fludarabine at days −5, −4 and −3 prior to T cell administration at a dose of 500 mg/m$^2$ of body surface area of cyclophosphamide per day and a dose of 30 mg/m$^2$ of body surface area of fludarabine per day during that period of time. Other preconditioning embodiments comprise 200-300 mg/m$^2$ of body surface area of cyclophosphamide per day and a dose of 20-50 mg/m$^2$ of body surface area per day of fludarabine for three days. CLINICAL TRIAL-1 (NCT02348216) clinical trial has been described in detail in the Examples and in Neelapu, S S et al. 2017, *N Engl J Med* 2017; 377(26):2531-44) and Locke, et al. *Lancet Oncol.* 2019; 20:31-42.

In some embodiments, the methods of treatment comprise the administration of the immune cells in combination with other therapeutic agents or treatments (e.g., radiation, debulking). In some embodiments, the additional therapeutic agents or treatments are included to manage adverse events. In some embodiments, the additional therapeutic agents or treatments are included to improve therapeutic efficacy of the cell treatment. In some examples, they achieve both. Examples of therapeutic agents that may be used together with (before, after, and/or concurrently with) the immune cells are provided below and elsewhere in the specification.

In some embodiments, the methods further comprise administering a chemotherapeutic. In some embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 and U.S. Pat. Nos. 9,855,298 and 10,322,146, which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient. Another conditioning embodiment comprises cyclophosphamide 500 mg/m$^2$/day and fludarabine 30 mg/m$^2$/day for 3 days at days −5, −4, and −3. Another embodiment comprises serum cyclophosphamide and fludarabine at days −4, −3, and −2 prior to T cell administration at a dose of 500 mg/m$^2$ of body surface area of cyclophosphamide per day and a dose of 30 mg/m$^2$ of body surface area per day of fludarabine during that period of time. Another embodiment comprises cyclophosphamide at day −2 and fludarabine at days −4, −3, and −2 prior to T cell administration, at a dose of 900 mg/m$^2$ of body surface area of cyclophosphamide and a dose of 25 mg/m$^2$ of body surface area per day of fludarabine during that period of time. In another embodiment, the conditioning comprises cyclophosphamide and fludarabine at days −5, −4 and −3 prior to T cell administration at a dose of 500 mg/m$^2$ of body surface area of cyclophosphamide per day and a dose of 30 mg/m$^2$ of body surface area of fludarabine per day during that period of time. Another embodiment comprises cyclophosphamide at 300 mg/m$^2$ daily for 3 days and fludarabine 30 mg/m$^2$ daily for 3 days. Another embodiment comprises 3 days of fludarabine (30 mg/m$^2$) and cyclophosphamide (300 mg/m$^2$) is given 2 to 7 days prior to T cell administration. Another embodiment comprises 3000 mg/m$^2$ cyclophosphamide once on day −7 to −2. Another embodiment comprises cyclophosphamide 300 mg/m$^2$ daily for 3 days and fludarabine 30 mg/m² daily for 3 days with the last day occurring on day −7 to −2.

In some embodiments, the antigen binding molecule, transduced (or otherwise engineered) cells (such as CARs), and the chemotherapeutic agent are administered each in an amount effective to treat the disease or condition in the subject.

In some embodiments, compositions comprising immune cells (e.g., CAR-expressing immune effector cells) disclosed herein may be administered in conjunction (before, after, and/or concurrently with immune cell administration) with any number of other chemotherapeutic agents and/or radiation. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylol melamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone, trilostane; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; Polysaccharide K (PSK); razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone, R-CHOP (CHOP plus Rituximab), and G-CHOP (CHOP plus obinutuzumab).

In some embodiments, the chemotherapeutic agent is administered at the same time or within one week after the administration of the engineered immune cell. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein (before, after, and/or concurrently with T cell administration). For example, potentially useful additional therapeutic agents include PD-1 inhibitors such as nivolumab (OPDIVO®), pembrolizumab (KEYTRUDA®), Cemiplimab (Libtayo), pidilizumab (CureTech), and atezolizumab (Roche), and PD-L1 inhibitors such as atezolizumab, durvalumab, and avelumab.

Additional therapeutic agents suitable for use in combination (before, after, and/or concurrently with T cell administration) with the compositions and methods disclosed herein include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib), inhibitors of GM-CSF, CSF1, GM-CSFR, or CSF1R, in addition to anti-thymocyte globulin, lenzilumab and mavrilimumab.

In one embodiment, the GM-CSF inhibitor is selected from lenzilumab; namilumab (AMG203); GSK3196165/MOR103/otilimab (GSK/MorphoSys); KB002 and KB003

(KaloBios); MT203 (Micromet and Nycomed); MORAb-022/gimsilumab (Morphotek); or a biosimilar of any one of the same; E21R; and a small molecule. In one embodiment, the CSF1 inhibitor is selected from RG7155, PD-0360324, MCS110/lacnotuzumab, or a biosimilar version of any one of the same; and a small molecule. In one embodiment, the GM-CSFR inhibitor and the CSF1R inhibitor is/are selected from Mavrilimumab (formerly CAM-3001; MedImmune, Inc.); cabiralizumab (Five Prime Therapeutics); LY3022855 (IMC-CS4)(Eli Lilly), Emactuzumab, also known as RG7155 or RO5509554; FPA008 (Five Prime/BMS); AMG820 (Amgen); ARRY-382 (Array Biopharma); MCS 110 (Novartis); PLX3397 (Plexxikon); ELB041/AFS98/TG3003 (ElsaLys Bio, Transgene), SNDX-6352 (Syndax); a biosimilar version of any one of the same; and a small molecule.

In some embodiments, the agent is administered by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal and, if desired for local treatment, intralesional administration. Parenteral infusions include intramuscular, intravenous, intraarterial, intraperitoneal, or subcutaneous administration.

In some embodiments, the treatment further comprises bridging therapy, which is therapy between conditioning and the compositions disclosed herein or therapy administered after leukapheresis and completed prior to initiating conditioning chemotherapy. In some embodiments, the bridging therapy comprises, CHOP, G-CHOP, R-CHOP (rituximab, cyclophosphamide, doxorubicin, vincristine, and prednisolone), corticosteroids, bendamustine, platinum compounds, anthracyclines, and/or phosphoinositide 3-kinase (PI3K) inhibitors. In some embodiments, the PI3K inhibitor is selected from duvelisib, idelalisib, venetoclax, pictilisib (GDC-0941), copanlisib, PX-866, buparlisib (BKM120), pilaralisib (XL-147), GNE-317, Alpelisib (BYL719), INK1117, GSK2636771, AZD8186, SAR260301, and Taselisib (GDC-0032). In some embodiments, the AKT inhibitor is perifosine, MK-2206. In one embodiment, the mTOR inhibitor is selected from everolimus, sirolimus, temsirolimus, ridaforolimus. In some embodiments, the dual PI3K/mTOR inhibitor is selected from BEZ235, XL765, and GDC-0980. In some embodiments, the PI3K inhibitor is selected from duvelisib, idelalisib, venetoclax, pictilisib (GDC-0941), copanlisib, PX-866, buparlisib (BKM120), pilaralisib (XL-147), GNE-317, Alpelisib (BYL719), INK1117, GSK2636771, AZD8186, SAR260301, and Taselisib (GDC-0032).

In some embodiments, the bridging therapy comprises acalabrutinib, brentuximab vedotin, copanlisib hydrochloride, nelarabine, belinostat, bendamustine hydrochloride, carmustine, bleomycin sulfate, bortezomib, zanubrutinib, carmustine, chlorambucil, copanlisib hydrochloride, denileukin diftitox, dexamethasone, doxorubicin hydrochloride, duvelisib, pralatrexate, obinutuzumab, ibritumomab tiuxetan, ibrutinib, idelalisib, recombinant interferon alfa-2b, romidepsin, lenalidomide, mechloretamine hydrochloride, methotrexate, mogamulizumab-kpc, prerixafor, nelarabine, obinutuzumab, denileukin diftitox, pembrolizumab, plerixafor, polatuzumab vedotin-piiq, mogamulizumab-kpc, prednisone, rituximab, hyaluronidase, romidepsin, bortezomib, venetoclax, vinblastine sulfate, vorinostat, zanubrutinib, CHOP, COPP, CVP, EPOCH, R-EPOCH, HYPER-CVAD, ICE, R-ICE, R-CHOP, R-CVP, and combinations of the same.

In some embodiments, the cell immunotherapy is administered in conjunction with debulking therapy, which is used with the aim of reducing tumor burden. In one embodiment, debulking therapy is to be administered after leukapheresis and prior to administration of conditioning chemotherapy or cell infusion. Examples of debulking therapy include the following:

| Type | Proposed Regimen[a] | Timing/Washout |
|---|---|---|
| R-CHOP | Rituximab 375 mg/m2 Day 1 Doxorubicin 50 mg/m2 Day 1 Prednisone 100 mg Day 1 through Day 5 Cyclophosphamide 750 mg/m2 Day 1 Vincristine 1.4 mg/m2 Day 1 | Should be administered after leukapheresis/enrollment and should be completed at least 14 days prior to the start of conditioning chemotherapy |
| R-ICE | Rituximab 375 mg/m2 Day 1 Ifosfamide 5 g/m2 24 h-CI Day 2 Carboplatin AUC5 Day 2 maximum dose 800 mg Etoposide 100 mg/m2/d Days 1 through Day 3 | |
| R-GEMOX | Rituximab 375 mg/m2 Day 1 Gemcitabine 1000 mg/m2 Day 2 Oxaliplatin 100 mg/m2 Day 2 | |
| R-GDP | Rituximab 375 mg/m2 Day 1 (or Day 8) Gemcitabine 1 g/m2 on Day 1 and Day 8 Dexamethasone 40 mg on Day 1 through Day 4 Cisplatin 75 mg/m2 on Day 1 (or carboplatin AUC5 on Day 1) | |

| Type | Proposed Regimen[a] | Timing/Washout |
|---|---|---|
| RADIOTHERAPY[b] | Per local standard up to 20 to 30 Gy | Should be administered after leukapheresis/enrollment and should be completed at least 5 days prior to the start of conditioning chemotherapy |

Abbreviations: AUC, area under the curve
[a]Other debulking treatment options may be used, to be discussed with the medical monitor. Supportive care with hydration, anti-emesis, mesna, growth factor support, and tumor lysis prophylaxis according to local standard may be used. More than 1 cycle allowed.
[b]At least 1 target lesion should remain outside of the radiation field to allow for tumor measurements In some embodiments, a composition comprising immune cells (e.g., engineered CAR T cells) are administered with an anti-inflammatory agent (before, after, and/or concurrently with immune cell administration). Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAID s include ibuprofen, naproxen, naproxen sodium, Cox-2 inhibitors, and sialylates. Exemplary analgesics include acetaminophen, oxycodone, tramadol of propoxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In some embodiments, the compositions described herein are administered in conjunction with a cytokine (before, after, or concurrently with T cell administration). Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO, Epogen®, Procrit®); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In some embodiments, the administration of the cells and the administration of the additional therapeutic agent are carried out on the same day, are carried out no more than 36 hours apart, no more than 24 hours apart, no more than 12 hours apart, no more than 6 hours apart, no more than 4 hours apart, no more than 2 hours apart, or no more than 1 hour apart or no more than 30 minutes apart. In some embodiments, the administration of the cells and the administration of the additional therapeutic agent are carried out between at or about 0 and at or about 48 hours, between at or about 0 and at or about 36 hours, between at or about 0 and at or about 24 hours, between at or about 0 and at or about 12 hours, between at or about 0 and at or about 6 hours, between at or about 0 and at or about 2 hours, between at or about 0 and at or about 1 hours, between at or about 0 and at or about 30 minutes, between at or about 30 minutes and at or about 48 hours, between at or about 30 minutes and at or about 36 hours, between at or about 30 minutes and at or about 24 hours, between at or about 30 minutes and at or about 12 hours, between at or about 30 minutes and at or about 6 hours, between at or about 30 minutes and at or about 4 hours, between at or about 30 minutes and at or about 2 hours, between at or about 30 minutes and at or about 1 hour, between at or about 1 hours and at or about 48 hours, between at or about 1 hour and at or about 36 hours, between at or about 1 hour and at or about 24 hours, between at or about 1 hour and at or about 12 hours, between at or about 1 hour and at or about 6 hours, between at or about 1 hour and at or about 4 hours, between at or about 1 hour and at or about 2 hours, between at or about 2 hours and at or about 48 hours, between at or about 2 hours and at or about 36 hours, between at or about 2 hours and at or about 24 hours, between at or about 2 hours and at or about 12 hours, between at or about 2 hours and at or about 6 hours, between at or about 2 hours and at or about 4 hours, between at or about 4 hours and at or about 48 hours, between at or about 4 hours and at or about 36 hours, between at or about 4 hours and at or about 24 hours, between at or about 4 hours and at or about 12 hours, between at or about 4 hours and at or about 6 hours, between at or about 6 hours and at or about 48 hours, between at or about 6 hours and at or about 36 hours, between at or about 6 hours and at or about 24 hours, between at or about 6 hours and at or about 12 hours, between at or about 12 hours and at or about 48 hours, between at or about 12 hours and at or about 36 hours, between at or about 12 hours and at or about 24 hours, between at or about 24 hours and at or about 48 hours, between at or about 24 hours and at or about 36 hours or between at or about 36 hours and at or about 48 hours. In some embodiments, the cells and the additional therapeutic agent are administered at the same time.

In some embodiments, the agent is administered in a dosage amount of from or from about 30 mg to 5000 mg, such as 50 mg to 1000 mg, 50 mg to 500 mg, 50 mg to 200 mg, 50 mg to 100 mg, 100 mg to 1000 mg, 100 mg to 500 mg, 100 mg to 200 mg, 200 mg to 1000 mg, 200 mg to 500 mg or 500 mg to 1000 mg. In some embodiments, the agent is administered in a dosage amount from 0.5 mg/kg to 100 mg/kg, 1 mg/kg to 50 mg/kg, 1 mg kg to 25 mg/kg, 1 mg/kg to 10 mg/kg, 1 mg/kg to 5 mg/kg, 5 mg/kg to 100 mg/kg, 5 mg/kg to 50 mg/kg, 5 mg/kg to 25 mg/kg, 5 mg/kg to 10 mg/kg, 10 mg/kg to 100 mg/kg, 10 mg/kg to 50 mg/kg, 10 mg/kg to 25 mg/kg, 25 mg/kg to 100 mg/kg, 25 mg/kg to 50 mg/kg to 50 mg/kg to 100 mg/kg. In some embodiments, the agent is administered in a dosage amount from 1 mg/kg to 10 mg/kg, 2 mg kg/to 8 mg/kg, 2 mg/kg to 6 mg/kg, 2 mg/kg to 4 mg/kg or 6 mg/kg to 8 mg/kg, each In some aspects, the agent is administered in a dosage amount of at least 1 mg/kg, 2 mg/kg, 4 mg/kg, 6 mg/kg, 8 mg/kg, 10 mg/kg or more.

Measuring Response and Efficacy

In some embodiments, methods described herein may provide a clinical benefit to a subject. In some embodiments, at least 1%, 2%, 3%, 4%, 5%, 6%, 7%, 8%, 9%, 10%, 15%, 20%, 25%, 30%, 35%, 40%, 50%, 55%, 60%, 65%, 70%, 75%, 80%, 85%, 90% or 95% of patients achieve a clinical benefit. In some embodiments, approximately 1%, 2%, 3%, 4%, 5%, 6%, 7%, 8%, 9%, 10%, 15%, 20%, 25%, 30%, 35%, 40%, 45%, 0%, 55%, 60%, 65%, 70%, 75%, 80%, 85%, 90% or 95% and any unenumerated % in between of patients achieve a clinical benefit. In some embodiments, the response rate is 1%, 2%, 3%, 4%, 5%, 6%, 7%, 8%, 9%, 9.5%, 10.5%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 25 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81, 82, 83, 84, 85, 86, 87, 88, 89, 90, 91, 92, 93, 94, 95, 96, 97, 98, 99, or 100% or some other unenumerated percentage and range in between 1% and 100%. In some embodiments, the response rate is between 0%-10%, 10%-20%, 20%-30%, 30%-40%, 40%-50%, 50%-60%, 60%-70%, 70%-80%, 80%-90%, or 90%-100%. In some embodiments, the response rate is between 0%-1%, 1%-1.5%, 1.5%-2%, 2%-3%, 3%-4%, 4%-5%, 5%-6%, 6%-7%, 7%-8%, 8%-9%, 9%-10%, 10%-15%, 15%-20%, 20-25%, 25%-30%, 35-40%, and so one and so forth, through 95%-100%.

Clinical benefit may be objective response or durable clinical response defined as ongoing response at a median follow up time of 1 year. In some embodiments, response, levels of CAR T cells in blood, or immune related factors is determined by follow up at about 1 day, about 2 days, about 3 days, about 4 days, about 5 days, about 6 days, or about 7 days after administration of engineered CAR T cells. In some embodiments, response, levels of CAR T cells in blood, or immune related factors is determined by follow up at about 1 week, about 2 weeks, about 3 weeks, or about 4 weeks after administration of engineered CAR T cells. In some embodiments, response, levels of CAR T cells in blood and/or immune related factors are determined by follow up at about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months after administration of a engineered CAR T cells. In some embodiments, response, levels of CAR T cells in blood and/or immune related factors are determined by follow up at about 1 year, about 1.5 years, about 2 years, about 2.5 years, about 3 years, about 4 years, or about 5 years after administration of engineered CAR T cells.

Monitoring

In some embodiments, administration of chimeric receptor T cell immunotherapy occurs at a certified healthcare facility.

In some embodiments, the methods disclosed herein comprise monitoring patients at least daily for 7 days at the certified healthcare facility following infusion for signs and symptoms of CRS and neurologic toxicities and other adverse reactions to CAR T cell treatment. In some embodiments, the symptom of neurologic toxicity is selected from encephalopathy, headache, tremor, dizziness, aphasia, delirium, insomnia, and anxiety. In some embodiments, the symptom of adverse reaction is selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia. In some embodiments, patients are instructed to remain within proximity of the certified healthcare facility for at least 4 weeks following infusion.

Clinical Outcomes

In some embodiments, the clinical outcome is complete response. In some embodiments, the clinical outcome is durable response. In some embodiments, the clinical outcome is complete response. In some embodiments, the clinical outcome is no response. In some embodiments, the clinical outcome is partial response. In some embodiments, the clinical outcome is objective response. In some embodiments, the clinical outcome is survival. In some embodiments, the clinical outcome is relapse.

In some embodiments, objective response (OR) is determined per the revised IWG Response Criteria for Malignant Lymphoma (Cheson, 2007) and determined by IWG Response Criteria for Malignant Lymphoma (Cheson et al. Journal of Clinical Oncology 32, no. 27 (September 2014) 3059-3067). Duration of Response (DOR) is defined only for subjects who experience an objective response and is the time from the first objective response to disease progression per (Cheson et al, 2014) or disease-related death, whichever comes first. The Progression-Free Survival (PFS) by investigator assessment per Lugano Response Classification Criteria is evaluated.

Prevention or Management of Severe Adverse Reactions

In some embodiments, the present disclosure provides methods of preventing the development or reducing the severity of adverse reactions based on the levels of one or more attributes. In some embodiments, the cell therapy is administered in with one or more agents that prevents, delays the onset of, reduces the symptoms of, treats the adverse events, which include cytokine release syndromes and neurologic toxicity. In one embodiment, the agent has been described above. In other embodiments, the agent is described below. In some embodiments, the agent is administered by one of the methods and doses described elsewhere in the specification, before, after, or concurrently with the administration of the cells. In one embodiment, the agent(s) are administered to a subject that may be predisposed to the disease but has not yet been diagnosed with the disease.

In this respect, the disclosed method may comprise administering a "prophylactically effective amount" of tocilizumab, of a corticosteroid therapy, and/or of an anti-seizure medicine for toxicity prophylaxis. In some embodiments, the method comprises administering inhibitors of GM-CSF, CSF1, GM-CSFR, or CSF1R, lenzilumab, mavrilimumab, cytokines, and/or anti-inflammatory agents. The pharmacologic and/or physiologic effect may be prophylactic, i.e., the effect completely or partially prevents a disease or symptom thereof. A "prophylactically effective amount" may refer to an amount effective, at dosages and for periods of time necessary, to achieve a desired prophylactic result (e.g., prevention of onset of adverse reactions).

In some embodiments, the method comprises management of adverse reactions in any subject. In some embodiments, the adverse reaction is selected from the group consisting of cytokine release syndrome (CRS), a neurologic toxicity, a hypersensitivity reaction, a serious infection, a cytopenia and hypogammaglobulinemia.

In some embodiments, the signs and symptoms of adverse reactions are selected from the group consisting of fever, hypotension, tachycardia, hypoxia, and chills, include cardiac arrhythmias (including atrial fibrillation and ventricular tachycardia), cardiac arrest, cardiac failure, renal insufficiency, capillary leak syndrome, hypotension, hypoxia, organ toxicity, hemophagocytic lymphohistiocytosis/macrophage activation syndrome (HLH/MAS), seizure, encephalopathy, headache, tremor, dizziness, aphasia, delirium, insomnia anxiety, anaphylaxis, febrile neutropenia, thrombocytopenia, neutropenia, and anemia.

In some embodiments, the patient has been identified and selected based on one or more of the biomarkers described in this application. In some embodiments, the patient has been identified and selected simply by the clinical presentation (e.g., presence and grade of toxicity symptom).

Cytokine Release Syndrome (CRS)

In some embodiments, the method comprises preventing or reducing the severity of CRS in a chimeric receptor treatment. In some embodiments, the engineered Immune cells (e.g., CAR T cells) are deactivated after administration to the patient.

In some embodiments, the method comprises identifying CRS based on clinical presentation. In some embodiments, the method comprises evaluating for and treating other causes of fever, hypoxia, and hypotension. Patients who experience ≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered.

In some embodiments, the method comprises monitoring patients at least daily for 7 days at the certified healthcare facility following infusion for signs and symptoms of CRS. In some embodiments, the method comprises monitoring patients for signs or symptoms of CRS for 4 weeks after infusion. In some embodiments, the method comprises counseling patients to seek immediate medical attention should signs or symptoms of CRS occur at any time. In some embodiments, the method comprises instituting treatment with supportive care, tocilizumab or tocilizumab and corticosteroids as indicated at the first sign of CRS.

Neurologic Toxicity (NT)

In some embodiments, the method comprises monitoring patients for signs and symptoms of neurologic toxicities. In some embodiments, the method comprises ruling out other causes of neurologic symptoms. Patients who experience ≥Grade 2 neurologic toxicities should be monitored with continuous cardiac telemetry and pulse oximetry. Provide intensive care supportive therapy for severe or life-threatening neurologic toxicities. In some embodiments, the symptom of neurologic toxicity is selected from encephalopathy, headache, tremor, dizziness, aphasia, delirium, insomnia, and anxiety.

Management of Adverse Events

In some embodiments, the cell treatment is administered before, during/concurrently, and/or after the administration of one or more agents (e.g., steroids) or treatments (e.g., debulking) that treat and or prevent (are prophylactic) one or more symptoms of adverse events. A "prophylactically effective amount" refers to an amount effective, at dosages and for periods of time necessary, to achieve the desired prophylactic result. In one embodiment, a prophylactically effective amount is used in subjects prior to or at an earlier stage of disease. In one embodiment, the prophylactically effective amount will be less than the therapeutically effective amount. In some embodiments, the patient is selected for management of adverse events based on the expression of one of more of the markers described herein in this specification. In one embodiment, the adverse event treatment or prophylaxis is administered to any patient that will receive, is receiving, or has received cell therapy.

In some embodiments, the method of managing adverse events comprises monitoring patients at least daily for 7 days at the certified healthcare facility following infusion for signs and symptoms of neurologic toxicities. In some embodiments, the method comprises monitoring patients for signs or symptoms of neurologic toxicities and/or CRS for 4 weeks after infusion.

In some embodiments, the disclosure provides two methods of managing adverse events in subjects receiving CAR T cell treatment with steroids and anti-IL6/anti-IL-6R antibody/ies. In one embodiment, the methods are described in FIG. 46. In one embodiment, the disclosure provides that early steroid intervention in Cohort 4 is associated with lower rates of severe CRS and neurologic events than what was observed in Cohorts 1+2. In one embodiment, the disclosure provides that earlier use of steroids in Cohort 4 was associated with a median cumulative cortisone-equivalent dose approximately 15% of that in Cohorts 1+2, suggesting that earlier steroid use may allow reduction of overall steroid exposure. Accordingly, in one embodiment, the disclosure provides a method of adverse event management whereby corticosteroid therapy is initiated for management of all cases of grade 1 CRS if there was no improvement after 3 days and for all grade≥1 neurologic events. In one embodiment, tocilizumab is initiated for all cases of grade 1 CRS if there is no improvement after 3 days and for all grade≥2 neurologic events. In one embodiment, the disclosure provides a method of reducing overall steroid exposure in patients receiving adverse event management after CAR T cell administration, the method comprising initiation of corticosteroid therapy for management of all cases of grade 1 CRS if there was no improvement after 3 days and for all grade≥1 neurologic events and/or initiation of tocilizumab for all cases of grade 1 CRS if there is no improvement after 3 days and for all grade≥2 neurologic events. In one embodiment, the corticosteroid and tocilizumab are administering in a regimen selected from those exemplified in Table 12. In one embodiment, the disclosure provides that earlier steroid use is not associated with increased risk for severe infection, decreased CAR T-cell expansion, or decreased tumor response.

In one embodiment, the disclosure supports the safety of levetiracetam prophylaxis in CAR T cell cancer treatment. In one embodiment, the cancer is NHL. In one embodiment, the cancer is R/R LBCL and the patients receive axicabtagene ciloleucel. Accordingly, in one embodiment, the disclosure provides a method of managing adverse events in patients treated with Immune cells (e.g., CAR T cells) comprising administering to the patient a prophylactic dosage of an anti-seizure medication. In some embodiments, the patients receive levetiracetam (for example, 750 mg orally or intravenous twice daily) starting on day 0 of the CAR T cell treatment (after conditioning) and also at the onset of grade≥2 neurologic toxicities, if neurologic events occur after the discontinuation of prophylactic levetiracetam. In one embodiment, if a patient does not experience any grade≥2 neurologic toxicities, levetiracetam is tapered and discontinued as clinically indicated. In one embodiment, levetiracetam prophylaxis is combined with any other adverse event management protocol.

In one embodiment, the disclosure provides that CAR T-cell levels in the patients subject to the adverse management protocol of Cohort 4 were comparable to those of Cohorts 1+2. In one embodiment, the disclosure provides that the numerical levels of inflammatory cytokines associated with CAR-related inflammatory events (e.g., IFNγ, IL-2 and GM-CSF) are lower in Cohort 4 than in Cohorts 1+2. Accordingly, the disclosure provides a method of reducing CAR T cell treatment-related inflammatory events without impact on CAR T cell levels comprising administering to the patient the adverse event management protocol of Cohort 4. The disclosure also provides a method of reducing cytokine production by immune cells after CAR T cell therapy comprising administering to the patient the adverse event management protocol of Cohort 4. In one embodiment, this effect is obtained without affecting CAR T-cell expansion and response rates. In one embodiment, the patient has R/R LBCL. In one embodiment, the CAR T cell treatment is anti-CD19 CAR T cell treatment. In one embodiment, the CAR T cell treatment comprises axicabtagene ciloleucel.

In one embodiment, the disclosure provides that early or prophylactic use of tocilizumab following axicabtagene ciloleucel for adverse event management decreased grade≥3 cytokine release syndrome but increased grade≥3 neurologic events. Accordingly, the disclosure provides a method for adverse event management in CAR T-cell therapy as described in FIG. 56. In one embodiment, patients receive levetiracetam (750 mg oral or intravenous twice daily) starting on day 0. At the onset of grade≥2 neurologic events, levetiracetam dose is increased to 1000 mg twice daily. If a patient did not experience any grade≥2 neurologic event, levetiracetam is tapered and discontinued as clinically indicated. Patients also receive tocilizumab (8 mg/kg IV over 1 hour [not to exceed 800 mg]) on day 2. Further tocilizumab (±corticosteroids) may be recommended at the onset of grade 2 CRS in patients with comorbidities or older age, or otherwise in case of grade≥3 CRS. For patients experiencing grade≥2 neurologic events, tocilizumab is initiated, and corticosteroids are added for patients with comorbidities or older age, or if there is any occurrence of a grade≥3 neurologic event with worsening symptoms despite tocilizumab use.

In one embodiment, the disclosure provides that prophylactic steroid use appears to reduce the rate of severe CRS and NEs to a similar extent as early steroid use following axicabtagene ciloleucel administration. Accordingly, the disclosure provides a method for adverse event management in CAR T-cell therapy wherein patients receive dexamethasone 10 mg PO on Days 0 (prior to axicabtagene ciloleucel infusion), 1, and 2. Steroids are also administered starting at Grade 1 NE, and for Grade 1 CRS when no improvement is observed after 3 days of supportive care. Tocilizumab is also administered for Grade≥1 CRS if no improvement is observed after 24 hours of supportive care.

In one embodiment, the disclosure provides that adverse event management of CAR T-cell therapy with an antibody that neutralizes and/or depletes GM-CSF prevents or reduces treatment-related CRS and/or NEs in treated patients. In one embodiment, the antibody is lenzilumab.

In some embodiments, the adverse events are managed by the administration of an agent/agents that is/are an antagonist or inhibitor of IL-6 or the IL-6 receptor (IL-6R). In some embodiments, the agent is an antibody that neutralizes IL-6 activity, such as an antibody or antigen-binding fragment that binds to IL-6 or IL-6R. For example, in some embodiments, the agent is or comprises tocilizumab (atlizumab) or sarilumab, anti-IL-6R antibodies. In some embodiments, the agent is an anti-IL-6R antibody described in U.S. Pat. No. 8,562,991. In some cases, the agent that targets IL-6 is an anti-TL-6 antibody, such as siltuximab, elsilimomab, ALD518/BMS-945429, sirukumab (CNTO 136), CPSI-2634, ARGX 109, FE301, FM101, or olokizumab (CDP6038), and combinations thereof. In some embodiments, the agent may neutralize IL-6 activity by inhibiting the ligand-receptor interactions. In some embodiments, the IL-6/IL-6R antagonist or inhibitor is an IL-6 mutein, such as one described in U.S. Pat. No. 5,591,827. In some embodiments, the agent that is an antagonist or inhibitor of IL-6/IL-6R is a small molecule, a protein or peptide, or a nucleic acid.

In some embodiments, other agents that may be used to manage adverse reactions and their symptoms include an antagonist or inhibitor of a cytokine receptor or cytokine. In some embodiments, the cytokine or receptor is IL-10, TL-6, TL-6 receptor, IFNγ, IFNGR, IL-2, IL-2R/CD25, MCP-1, CCR2, CCR4, MIP13, CCR5, TNFalpha, TNFR1, such as TL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1P receptor (e.g., CCR5), TNF alpha receptor (e.g., TNFR1), IL-1 receptor (IL1-Ra/IL-1RP), or IL-10 receptor (IL-10R), IL-1, and IL-1Ralpha/IL-1beta. In some embodiments, the agent comprises siltuximab, sarilumab, olokizumab (CDP6038), elsilimomab, ALD518/BMS-945429, sirukumab (CNTO 136), CPSI-2634, ARGX 109, FE301, or FM101. In some embodiments, the agent, is an antagonist or inhibitor of a cytokine, such as transforming growth factor beta (TGF-beta), interleukin 6 (TL-6), interleukin 10 (IL-10), IL-2, MIP13 (CCL4), TNF alpha, IL-1, interferon gamma (IFN-gamma), or monocyte chemoattractant protein-I (MCP-1). In some embodiments, the is one that targets (e.g., inhibits or is an antagonist of) a cytokine receptor, such as TL-6 receptor (IL-6R), IL-2 receptor (IL-2R/CD25), MCP-1 (CCL2) receptor (CCR2 or CCR4), a TGF-beta receptor (TGF-beta I, II, or III), IFN-gamma receptor (IFNGR), MIP1P receptor (e.g., CCR5), TNF alpha receptor (e.g., TNFR1), IL-1 receptor (IL1-Ra/IL-1RP), or IL-10 receptor (IL-10R) and combinations thereof. In some embodiments, the agent is administered by one of the methods and doses described elsewhere in the specification, before, after, or concurrently with the administration of the cells.

In some embodiments, the agent is administered in a dosage amount of from or from about 1 mg/kg to 10 mg/kg, 2 mg/kg to 8 mg/kg, 2 mg/kg to 6 mg/kg, 2 mg/kg to 4 mg/kg or 6 mg/kg to 8 mg/kg, each inclusive, or the agent is administered in a dosage amount of at least or at least about or about 2 mg/kg, 4 mg/kg, 6 mg/kg or 8 mg/kg. In some embodiments, is administered in a dosage amount from about 1 mg/kg to 12 mg/kg, such as at or about 10 mg/kg. In some embodiments, the agent is administered by intravenous infusion. In one embodiment, the agent is tocilizumab. In some embodiments, the (agent(s), e.g., specifically tocilizumab) is/are administered by one of the methods and doses described elsewhere in the specification, before, after, or concurrently with the administration of the cells.

In some embodiments, the method comprises identifying CRS based on clinical presentation. In some embodiments, the method comprises evaluating for and treating other causes of fever, hypoxia, and hypotension. If CRS is observed or suspected, it may be managed according to the recommendations in protocol A, which may also be used in combination with the other treatments of this disclosure, including Neutralization or Reduction of the CSF/CSFR1 Axis. Patients who experience ≥Grade 2 CRS (e.g., hypotension, not responsive to fluids, or hypoxia requiring supplemental oxygenation) should be monitored with continuous cardiac telemetry and pulse oximetry. In some embodiments, for patients experiencing severe CRS, consider performing an echocardiogram to assess cardiac function. For severe or life-threatening CRS, intensive care supportive therapy may be considered. In some embodiments, a biosimilar or equivalent of tocilizumab may be used instead of tocilizumab in the methods disclosed herein. In other embodiments, another anti-IL6R may be used instead of tocilizumab.

In some embodiments, adverse events are managed according to the following protocol (protocol A):

| CRS Grade (a) | Tocilizumab | Corticosteroids |
| --- | --- | --- |
| Grade 1<br>Symptoms require symptomatic treatment only (e.g., fever, nausea, fatigue, headache, myalgia, malaise). | N/A | N/A |
| Grade 2<br>Symptoms require and respond to moderate intervention.<br>Oxygen requirement less than 40% FiO$_2$ or hypotension responsive to fluids or low-dose of one vasopressor or Grade 2 organ toxicity (b). | Administer tocilizumab (c) 8 mg/kg IV over 1 hour (not to exceed 800 mg).<br>Repeat tocilizumab every 8 hours as needed if not responsive to IV fluids or increasing supplemental oxygen.<br>Limit to a maximum of 3 doses in a 24-hour period; maximum total of 4 doses if no clinical improvement in the signs and symptoms of CRS. | Manage per Grade 3 if no improvement within 24 hours after starting tocilizumab. |
| Grade 3<br>Symptoms require and respond to aggressive intervention.<br>Oxygen requirement greater than or equal to 40% FiO$_2$ or hypotension requiring high-dose or multiple vasopressors or Grade 3 organ toxicity or Grade 4 transaminitis | Per Grade 2 | Administer methylprednisolone 1 mg/kg IV twice daily or equivalent dexamethasone (e.g., 10 mg IV every 6 hours).<br>Continue corticosteroids use until the event is Grade 1 or less, then taper over 3 days.<br>If not improving, manage as Grade 4. |
| Grade 4<br>Life-threatening symptoms.<br>Requirements for ventilator support, continuous veno-venous hemodialysis (CVVHD) or<br>Grade 4 organ toxicity (excluding transaminitis). | Per Grade 2 | Administer methylprednisolone 1000 mg IV per day for 3 days; if improves, then manage as above.<br>Consider alternate immunosuppressants if no improvement or if condition worsens. |

(a) Lee DW et al., (2014). Current concepts in the diagnosis and management of cytokine release syndrome. Blood. 2014 Jul. 10; 124(2): 188-195.
(b) Refer to Table 2 for management of neurologic toxicity.
(c) Refer to ACEMTRA ® (tocilizumab) Prescribing Informationfor details, https://www.gene.com/download/pdf/actemra_prescribing.pdf (last accessed Oct. 18, 2017). Initial U.S. approval is indicated to be in 2010.

Neurologic Toxicity

In some embodiments, the method comprises monitoring patients for signs and symptoms of neurologic toxicities. In some embodiments, the method comprises ruling out other causes of neurologic symptoms. Patients who experience ≥Grade 2 neurologic toxicities should be monitored with continuous cardiac telemetry and pulse oximetry. Provide intensive care supportive therapy for severe or life-threatening neurologic toxicities. Consider non-sedating, anti-seizure medicines (e.g., levetiracetam) for seizure prophylaxis for any ≥Grade 2 neurologic toxicities. The following treatments may be used in combination with the other treatments of this disclosure, including Neutralization or Reduction of the CSF/CSFR1 Axis.

In some embodiments, adverse events are managed according to the following protocol (protocol B):

| Grading Assessment | Concurrent CRS | No concurrent CRS |
|---|---|---|
| Grade 2 | Administer tocilizumab per table above (protocol A) for management of Grade 2 CRS. If no improvement within 24 hours after starting tocilizumab, administer dexamethasone 10 mg IV every 6 hours if not already taking other steroids. Continue dexamethasone use until the event is Grade 1 or less, then taper over 3 days. | Administer dexamethasone 10 mg IV every 6 hours. Continue dexamethasone use until the event is Grade 1 or less, then taper over 3 days. |
| | Consider non-sedating, anti-seizure medicines (e.g., levetiracetam) for seizure prophylaxis. | |
| Grade 3 | Administer tocilizumab per (protocol A) for management of Grade 2 CRS. In addition, administer dexamethasone 10 mg IV with the first dose of tocilizumab and repeat dose every 6 hours. Continue dexamethasone use until the event is Grade 1 or less, then taper over 3 days. | Administer dexamethasone 10 mg IV every 6 hours. Continue dexamethasone use until the event is Grade 1 or less, then taper over 3 days. |
| | Consider non-sedating, anti-seizure medicines (e.g., levetiracetam) for seizure prophylaxis. | |
| Grade 4 | Administer tocilizumab per (protocol A) for management of Grade 2 CRS. Administer methylprednisolone 1000 mg IV per day with first dose of tocilizumab and continue methylprednisolone 1000 mg IV per day for 2 more days; if improves, then manage as above. | Administer methylprednisolone 1000 mg IV per day for 3 days; if improves, then manage as above. |
| | Consider non-sedating, anti-seizure medicines (e.g., levetiracetam) for seizure prophylaxis. | |

Additional Safety Management Strategies with Corticosteroids

Administration of corticosteroids and/or tocilizumab at Grade 1 may be considered prophylactic. Supportive care may be provided in all protocols at all CRS and NE severity grades.

In one embodiment of a protocol for management of adverse events related to CRS, tocilizumab and/or corticosteroids are administered as follows: Grade 1 CRS: no tocilizumab; no corticosteroids; Grade 2 CRS: tocilizumab (only in case of comorbidities or older age); and/or corticosteroids (only in case of comorbidities or older age); Grade 3 CRS: tocilizumab; and/or corticosteroids; Grade 4 CRS: tocilizumab; and/or corticosteroids. In another embodiment of a protocol for management of adverse events related to CRS, tocilizumab and/or corticosteroids are administered as follows: Grade 1 CRS: tocilizumab (if no improvement after 3 days); and/or corticosteroids (if no improvement after 3 days); Grade 2 CRS: tocilizumab; and/or corticosteroids; Grade 3 CRS: tocilizumab; and/or corticosteroids; Grade 4 CRS: tocilizumab; and/or corticosteroids, high dose.

In one embodiment of a protocol for management of adverse events related to NE, tocilizumab and/or corticosteroids are administered as follows: Grade 1 NE: no tocilizumab; no corticosteroids; Grade 2 NE: no tocilizumab; no corticosteroids; Grade 3 NE: tocilizumab; and/or corticosteroids (only if no improvement to tocilizumab, standard dose); Grade 4 NE: tocilizumab; and/or corticosteroids.

In another embodiment of a protocol for management of adverse events related to NE, tocilizumab and/or corticosteroids are administered as follows: Grade 1 NE: no tocilizumab; and/or corticosteroids; Grade 2 NE: tocilizumab; and/or corticosteroids; Grade 3 NE: tocilizumab; and/or corticosteroids, high dose; Grade 4 NE: tocilizumab; and/or corticosteroids, high dose.

In one embodiment, corticosteroid treatment is initiated at CRS grade≥2 and tocilizumab is initiated at CRS grade≥2. In one embodiment, corticosteroid treatment is initiated at CRS grade≥1 and tocilizumab is initiated at CRS grade≥1. In one embodiment, corticosteroid treatment is initiated at NE grade≥3 and tocilizumab is initiated at CRS grade≥3. In one embodiment, corticosteroid treatment is initiated at CRS grade≥1 and tocilizumab is initiated at CRS grade≥2. In some embodiments, prophylactic use of tocilizumab administered on Day 2 may decrease the rates of Grade≥3 CRS.

In one embodiment, adverse events may be managed by a method comprising protocol C:

| CRS Grade | Tocilizumab Dose[a] | Corticosteroid Dose[a] |
|---|---|---|
| 1 | 8 mg/kg over 1 hour[b] if no improvement after 24 hours of supportive care; repeat every 4-6 hours as needed | Dexamethasone 10 mg x 1 if no improvement after 3 days |
| 2 | 8 mg/kg over 1 hour[b]; repeat every 4-6 hours as needed | Dexamethasone 10 mg x1 |
| 3 | Per Grade 2 | Methylprednisolone 1 mg/kg IV twice daily or equivalent dexamethasone dose |

| | | -continued |
|---|---|---|
| 4 | Per Grade 2 | Methylprednisolone 1000 mg/d IV for 3 days |

| NE Grade | Tocilizumab Dose | Corticosteroid Dose |
|---|---|---|
| 1 | N/A | Dexamethasone 10 mg x1 |
| 2 | Only in the case of concurrent CRS; 8 mg/kg over 1 hour; repeat every 4-6 hours as needed | Dexamethasone 10 mg 4x/day |
| 3 | Per Grade 2 | Methylprednisolone 1 g once daily |
| 4 | Per Grade 2 | Methylprednisolone 1 g twice daily |

[a]Therapy to be tapered on improvement of symptoms at investigator's discretion;
[b]Not to exceed 800 mg; AE, adverse event; CRS, cytokine release syndrome; IV, intravenous; N/A, not applicable; NE, neurologic event Any corticosteroid may be appropriate for this use. In one embodiment, the corticosteroid is dexamethasone. In some embodiments, the corticosteroid is methylprednisolone. In some embodiments, the two are administered in combination. In some embodiments, glucocorticoids include synthetic and non-synthetic glucocorticoids. Exemplary glucocorticoids include, but are not limited to: alclomethasones, algestones, beclomethasones (e.g., beclomethasone dipropionate), betamethasones (e.g., betamethasone 17 valerate, betamethasone sodium acetate, betamethasone sodium phosphate, betamethasone valerate), budesonides, clobetasols (e.g., clobetasol propionate), clobetasones, clocortolones (e.g., clocortolone pivalate), cloprednols, corticosterones, cortisones and hydrocortisones (e.g., hydrocortisone acetate), cortivazols, deflazacorts, desonides, desoximethasones, dexamethasones (e.g., dexamethasone 21-phosphate, dexamethasone acetate, dexamethasone sodium phosphate), diflorasones (e.g., diflorasone diacetate), diflucortolones, difluprednates, enoxolones, fluazacorts, flucloronides, fludrocortisones (e.g., fludrocortisone acetate), flumethasones (e.g., flumethasone pivalate), flunisolides, fluocinolones (e.g., fluocinolone acetonide), fluocinonides, fluocortins, fluocortolones, fluorometholones (e.g., fluorometholone acetate), fluperolones (e.g., fluperolone acetate), fluprednidenes, fluprednisolones, flurandrenolides, fluticasones (e.g., fluticasone propionate), formocortals, halcinonides, halobetasols, halometasones, halopredones, hydrocortamates, hydrocortisones (e.g., hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylpredni solones (methylprednisolone aceponate, methylprednisolone acetate, methylprednisolone hemisuccinate, methylprednisolone sodium succinate), mometasones (e.g., mometasone furoate), paramethasones (e.g., paramethasone acetate), prednicarbates, prednisolones (e.g., prednisolone 25-diethylaminoacetate, prednisolone sodium phosphate, prednisolone 21-hemisuccinate, prednisolone acetate; prednisolone farnesylate, prednisolone hemisuccinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g., triamcinolone acetonide, triamcinolone benetonide, triamcinolone hexacetonide, triamcinolone acetonide 21 palmitate, triamcinolone diacetate). These glucocorticoids and the salts thereof are discussed in detail, for example, in Remington's Pharmaceutical Sciences, A. Osol, ed., Mack Pub. Co., Easton, Pa. (16th ed. 1980) and Remington: The Science and Practice of Pharmacy, 22nd Edition, Lippincott Williams & Wilkins, Philadelphia, Pa. (2013) and any other editions, which are hereby incorporated by reference. In some embodiments, the glucocorticoid is selected from among cortisones, dexamethasones, hydrocortisones, methylprednisolones, prednisolones and prednisones. In an embodiment, the glucocorticoid is dexamethasone. In other embodiments, the steroid is a mineralcorticoid. Any other steroid may be used in the methods provided herein.

The one or more corticosteroids may be administered at any dose and frequency of administration, which may be adjusted to the severity/grade of the adverse event (e.g., CRS and NE). Tables 1 and 2 provide examples of dosage regimens for management of CRS and NE, respectively. In another embodiment, corticosteroid administration comprises oral or IV dexamethasone 10 mg, 1-4 times per day. Another embodiment, sometimes referred to as "high-dose" corticosteroids, comprises administration of IV methylprednisone 1 g per day alone, or in combination with dexamethasone. In some embodiments, the one or more corticosteroids are administered at doses of 1-2 mg/kg per day.

The corticosteroid may be administered in any amount that is effective to ameliorate one or more symptoms associated with the adverse events, such as with the CRS or neurotoxicity. The corticosteroid, e.g., glucocorticoid, may be administered, for example, at an amount between at or about 0.1 and 100 mg, per dose, 0.1 to 80 mg, 0.1 to 60 mg, 0.1 to 40 mg, 0.1 to 30 mg, 0.1 to 20 mg, 0.1 to 15 mg, 0.1 to 10 mg, 0.1 to 5 mg, 0.2 to 40 mg, 0.2 to 30 mg, 0.2 to 20 mg, 0.2 to 15 mg, 0.2 to 10 mg, 0.2 to 5 mg, 0.4 to 40 mg, 0.4 to 30 mg, 0.4 to 20 mg, 0.4 to 15 mg, 0.4 to 10 mg, 0.4 to 5 mg, 0.4 to 4 mg, 1 to 20 mg, 1 to 15 mg or 1 to 10 mg, to a 70 kg adult human subject. Typically, the corticosteroid, such as a glucocorticoid is administered at an amount between at or about 0.4 and 20 mg, for example, at or about 0.4 mg, 0.5 mg, 0.6 mg, 0.7 mg, 0.75 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg per dose, to an average adult human subject.

In some embodiments, the corticosteroid may be administered, for example, at a dosage of at or about 0.001 mg/kg (of the subject), 0.002 mg/kg, 0.003 mg/kg, 0.004 mg/kg, 0.005 mg/kg, 0.006 mg/kg, 0.007 mg/kg, 0.008 mg/kg, 0.009 mg/kg, 0.01 mg/kg, 0.015 mg/kg, 0.02 mg/kg, 0.025 mg/kg, 0.03 mg/kg, 0.035 mg/kg, 0.04 mg/kg, 0.045 mg/kg, 0.05 mg/kg, 0.055 mg/kg, 0.06 mg/kg, 0.065 mg/kg, 0.07 mg/kg, 0.075 mg/kg, 0.08 mg/kg, 0.085 mg/kg, 0.09 mg/kg, 0.095 mg/kg, 0.1 mg/kg, 0.15 mg/kg, 0.2 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1 mg/kg, 1.05 mg/kg, 1.1 mg/kg, 1.15 mg/kg, 1.20 mg/kg, 1.25 mg/kg, 1.3 mg/kg, 1.35 mg/kg or 1.4 mg/kg, to an average adult human subject, typically weighing about 70 kg to 75 kg.

Generally, the dose of corticosteroid administered is dependent upon the specific corticosteroid, as a difference in potency exists between different corticosteroids. It is typically understood that drugs vary in potency, and that doses may therefore vary, in order to obtain equivalent effects. Equivalence in terms of potency for various glucocorticoids and routes of administration. is well known. Information relating to equivalent steroid dosing (in a non-chronotherapeutic manner) may be found in the British National Formulary (BNF) 37, March 1999.

In some embodiments, the adverse events are managed by the following protocol: patients receive levetiracetam (750 mg oral or intravenous twice daily) starting on day 0 of administration of T cell therapy; at the onset of grade≥2 neurologic events, levetiracetam dose is increased to 1000 mg twice daily; if a patient did not experience any grade≥2 neurologic event, levetiracetam is tapered and discontinued as clinically indicated; patients also receive tocilizumab (8 mg/kg IV over 1 hour [not to exceed 800 mg]) on day 2; further tocilizumab (±corticosteroids) may be recommended at the onset of grade 2 CRS in patients with comorbidities or older age, or otherwise in case of grade≥3 CRS; for patients experiencing grade≥2 neurologic events, tocilizumab is initiated, and corticosteroids are added for patients with comorbidities or older age, or if there is any occurrence of a grade≥3 neurologic event with worsening symptoms despite tocilizumab use. In some embodiments, levetiracetam is administered for prophylaxis and at the onset of grade≥2 neurologic toxicities, if neurologic events occur after the discontinuation of prophylactic levetiracetam and/or levetiracetam is tapered and discontinued if the patient does not experience any grade≥2 neurologic toxicities.

In some embodiments, the adverse events are managed by the following protocol: patients receive dexamethasone 10 mg PO on Days 0 (prior to T cell therapy infusion), 1, and 2; steroids are also administered starting at Grade 1 NE, and for Grade 1 CRS when no improvement is observed after 3 days of supportive care; tocilizumab is also administered for Grade≥1 CRS if no improvement is observed after 24 hours of supportive care.

Secondary Malignancies

In some embodiments, patients treated with Immune cells (e.g., CAR T cells) (e.g., CD19-directed) or other genetically modified autologous T cell immunotherapy may develop secondary malignancies. In certain embodiments, patients treated with CAR T cells (e.g., CD19-directed) or other genetically modified allogeneic T cell immunotherapy may develop secondary malignancies. In some embodiments, the method comprises monitoring life-long for secondary malignancies.

EXAMPLES

Example 1

This example provides results from an analysis of clinical trial CLINICAL TRIAL-2. The study design for the CLINICAL TRIAL-2 trial is summarized in FIG. 1. Presented here is a report on the safety and efficacy outcomes and the pharmacokinetic profile among patients in CLINICAL TRIAL-2 with and without progression of disease within 24 months of diagnosis (POD24). Progression of disease within 24 months after initial diagnosis (POD24) is an indicator of poor outcomes for patients with mantle cell lymphoma (MCL). (Visco C, et al. *Br J Haematol.* 2019; 185:940-944). In a retrospective analysis of patients with MCL, the median overall survival (OS) from time of progression was 12 months for those with POD24, compared with not reached for those without POD24. KTE-X19, an autologous anti-CD19 chimeric antigen receptor (CAR) T-cell therapy, is approved in the United States and European Union for the treatment of relapsed/refractory (R/R) MCL. (TECARTUS® (brexucabtagene autoleucel) Prescribing information. Kite Pharma, Inc; 2021; TECARTUS® (autologous anti-CD19-transduced CD3+ cells) Summary of product characteristics. Kite Pharma EU B.V.; 2021). The pivotal Phase 2 CLINICAL TRIAL-2 study evaluated KTE-X19 in patients with MCL who were R/R to 1-5 prior therapies, including a Bruton tyrosine kinase inhibitor (BTKi). (Wang M, et al. *N Engl J Med.* 2020; 382:1331-1342). After a median follow-up of 17.5 months in CLINICAL TRIAL-2 (N=60), the objective response rate (ORR) was 92%, with a complete response (CR) rate of 67%. (Wang M, et al. *Blood.* 2020; 136(Suppl 1):20-22). 48% of all patients and 70% of patients in CR were in ongoing response at data cutoff. Cytokine release syndrome (CRS) and neurologic events (NE) were mostly reversible (N=68 treated patients). 15% of the patients showed Grade≥3 CRS whereas 31% had Grade≥3 NE. Two patients showed Grade 5 adverse events (AEs), only one of which was KTE-X19-related. No new safety signals were observed with longer follow-up. (Wang M, et al. *N Engl J Med.* 2020; 382:1331-1342; Wang M, et al. *Blood.* 2020; 136(Suppl 1):20-22).

Eligible patients were aged≥18 years with pathologically confirmed Mantle Cell Lymphoma (MCL) with documentation of either cyclin D1 overexpression or presence of t(11; 14), and were relapsed/refractory to 1-5 prior regimens for MCL. Prior therapy having included anthracycline or bendamustine-containing chemotherapy, an anti-CD20 monoclonal antibody, and ibrutinib or acalabrutinib. All patients received prior BTKi. Although patients must have had prior BTKi therapy, it was not required as the last line of therapy before study entry, and patients were not required to be refractory to BTKi therapy. Eligible patients had an absolute lymphocyte count≥100/µL Patients who underwent autologous SCT within 6 weeks of CD19 CAR-T infusion or had previous CD19-targeted therapy or allogeneic SCT were excluded. All patients underwent leukapheresis to obtain cells for CD19 CAR-T cell treatment manufacturing. Patients received optional bridging therapy, which included dexamethasone (20-40 mg or equivalent), ibrutinib (560 mg by mouth (PO) daily), or acalabrutinib (100 mg PO twice daily). The manufacturing process of KTE-X19 was modified relative to that of axicabtagene ciloleucel to remove circulating lymphoma cells through positive enrichment for CD4$^+$/CD8$^+$ cells. This product is referred to herein as "the CAR T cells." Conditioning chemotherapy with fludarabine (30 mg/m$^2$/day) and cyclophosphamide (500 mg/m$^2$/day) was administered on days −5, −4, and −3 prior to a single intravenous infusion of 2×10$^6$ CAR T cells/kg of CD19 CAR-T cells on day 0.

In this Example, safety outcomes, pharmacological profile, and product attributes are reported for all 68 patients treated with KTE-X19. Efficacy outcomes are reported in the 60 treated patients with ≥1 year of follow-up (median 17.5 months). Data are presented with the data cutoff date of Dec. 31, 2019.

The patients' baseline characteristics are summarized in Table 1. High-risk disease characteristics were common in patients with and without POD24. Patients with POD24 had higher tumor burden and lactate dehydrogenase (LDH) levels, and more had blastoid type MCL suggesting these patients may be less fit than those without POD24. Patients with POD24 were more likely to have high-risk disease characteristics (high tumor burden, high LDH levels, and blastoid MCL) than those without POD24.

TABLE 1

Baseline characteristics by POD24 status.

| | With POD24 (n = 33) | Without POD24 (n = 35) |
|---|---|---|
| Median age (range), years | 65 (38-75) | 66 (50-79) |
| ≥65 years, n (%) | 18 (55) | 21 (60) |
| Male, n (%) | 29 (88) | 28 (80) |
| MCL morphology, n (%) | | |
| Classical | 16 (48) | 24 (69) |
| Pleomorphic | 2 (6) | 2 (6) |
| Blastoid | 11 (33) | 6 (17) |
| Intermediate-/high-risk MIPI, n (%) | 16 (48) | 22 (63) |
| Median tumor burden[a] (range), mm$^2$ | 2255 (260-14,390) | 1380 (293-16,878) |
| Extranodal disease, n (%) | 17 (52) | 21 (60) |
| LDH ≥ 1.5 × ULN, n (%) | 8 (24) | 3 (9) |
| Ki-67 proliferation index, n (%) | n = 23 | n = 26 |
| ≥30% | 19 (83) | 21 (81) |
| ≥50% | 17 (74) | 17 (65) |
| TP53 mutated, n/n (%) | 3/20 (15) | 3/16 (19) |
| Median no. prior therapies (range) | 3 (2-5) | 3 (1-5) |
| ≥3 prior therapies, n (%) | 29 (88) | 26 (74) |
| Prior BTKi, n (%) | 33 (100) | 35 (100) |
| Ibrutinib | 28 (85) | 30 (86) |
| Acalabrutinib | 7 (21) | 9 (26) |
| Both | 2 (6) | 4 (11) |
| Prior anthracycline, n (%) | 22 (67) | 27 (77) |
| Prior cytarabine, n (%) | 21 (64) | 18 (51) |
| Prior bendamustine, n (%) | 19 (58) | 18 (51) |
| Prior auto-SCT, n (%) | 12 (36) | 17 (49) |
| Bone marrow involvement, n (%) | 13 (39) | 24 (69) |

Figure 2:
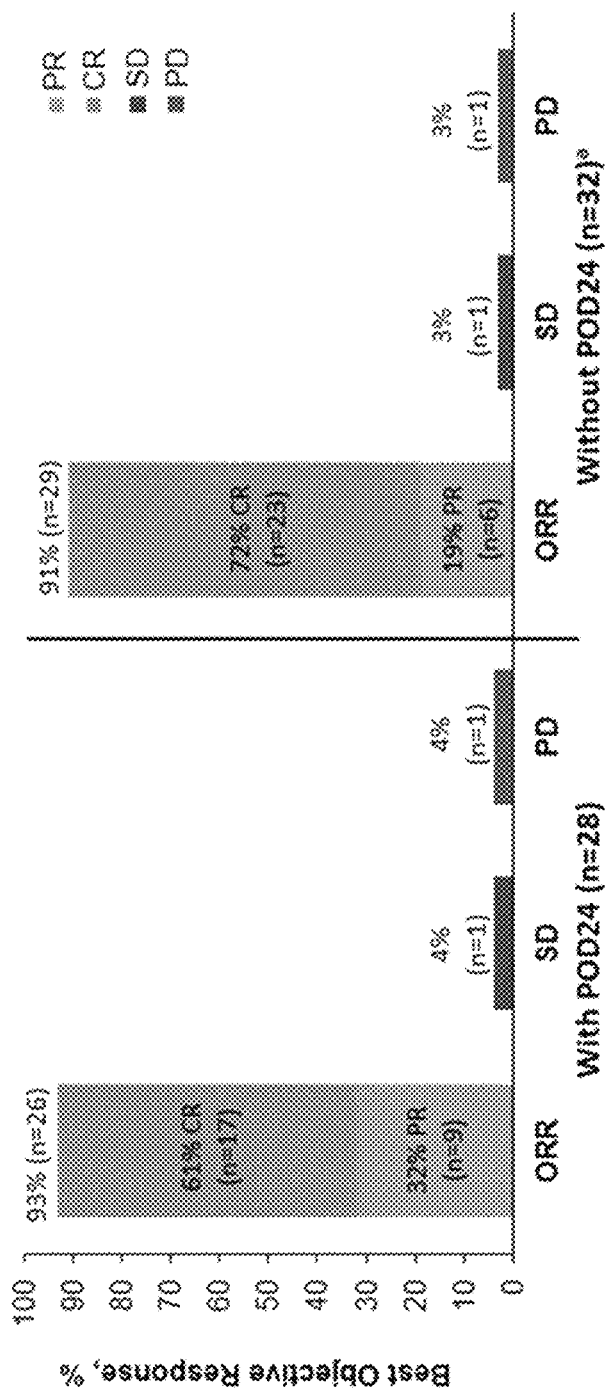
FIG. 2. ORR by IRRC Assessment in Patients With and Without MCL POD24. Assessed by an IRRC according to the Lugano Classification.[7] [a]One patient was not evaluable. CR, complete response; IRRC, Independent Radiology Review Committee; ORR, objective response rate; PD, progressive disease; with POD24, progression of disease<24 months after initial diagnosis; without POD24, progression of disease≥24 months after initial diagnosis; PR, partial response; SD, stable disease.

The overall response rate (ORR; CR and partial response) was assessed by an independent radiology review committee per the Lugano classification. Cheson B D et al., *Journal of clinical oncology* 2014; 32:3059-68. The ORR was similar among patients with and without POD24, with a slightly higher CR rate in patients without POD24 (FIG. 2). After a median of 17.5 months of follow-up, KTE-X19 provided a high CR rate in patients with and without POD24. Minimal residual disease (MRD; 10$^{-5}$ sensitivity) was assessed by next-generation sequencing, as previously reported. Wang M, et al. *New Engl J Med.* 2020; 382:1331-1342. MRD was assessed in patients with available samples at week 4. Similar rates of MRD-negativity were also observed among patients with (75%; n=9/12) and without (79%; n=15/19) POD24.

Figure 3A:
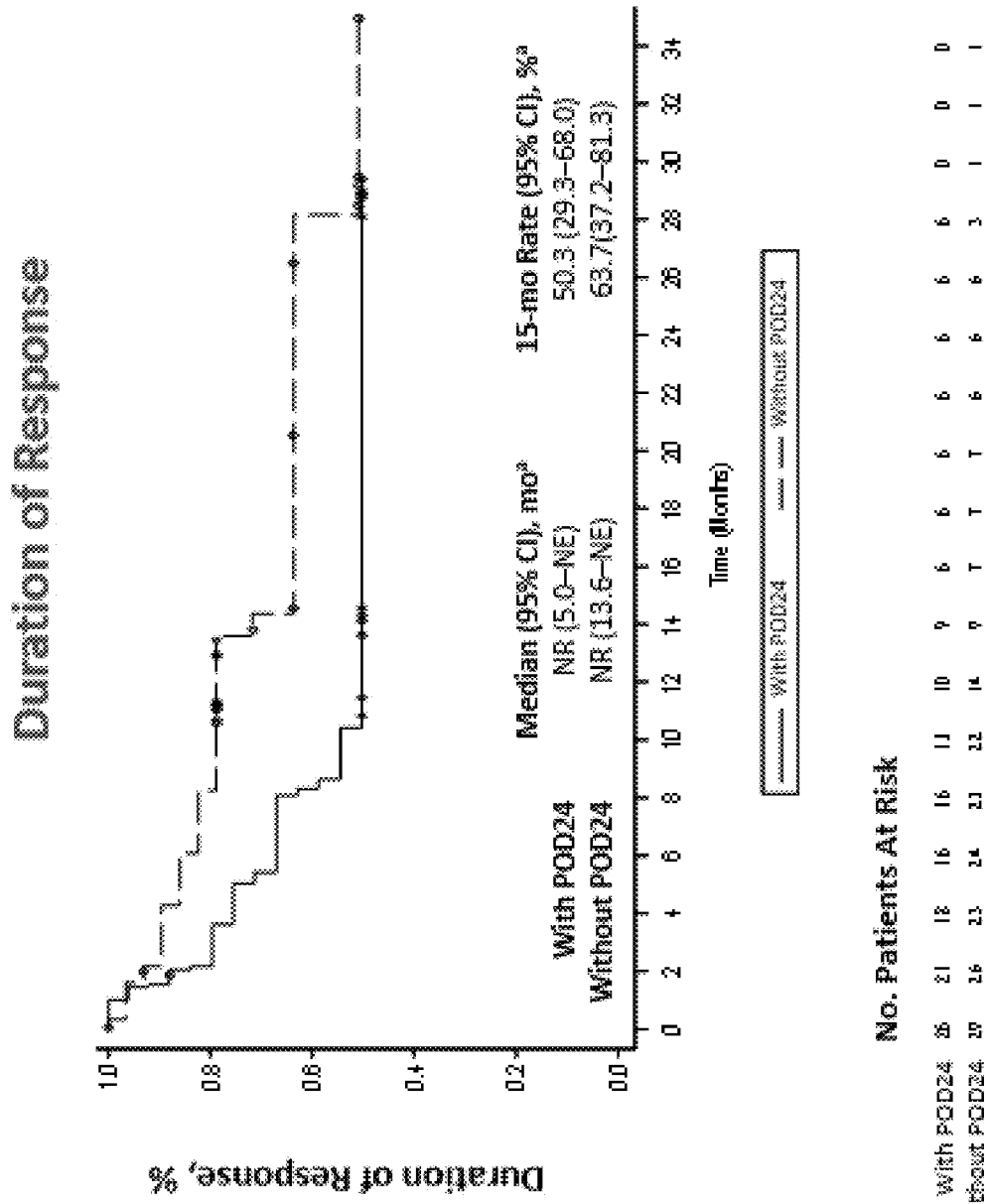
FIGS. 3A, 3B, and 3C. Duration of Response (DR) (3A), Progression-Free Survival (PFS) (3B), and Overall Survival (OS) (3C) by MCL POD24 Status. [a]Of responding patients. DOR, duration of response; NE, not estimable; OS, overall survival; PFS, progression-free survival; with POD24, progression of disease<24 months after initial diagnosis; without POD24, progression of disease≥24 months after initial diagnosis.
Figure 3B:
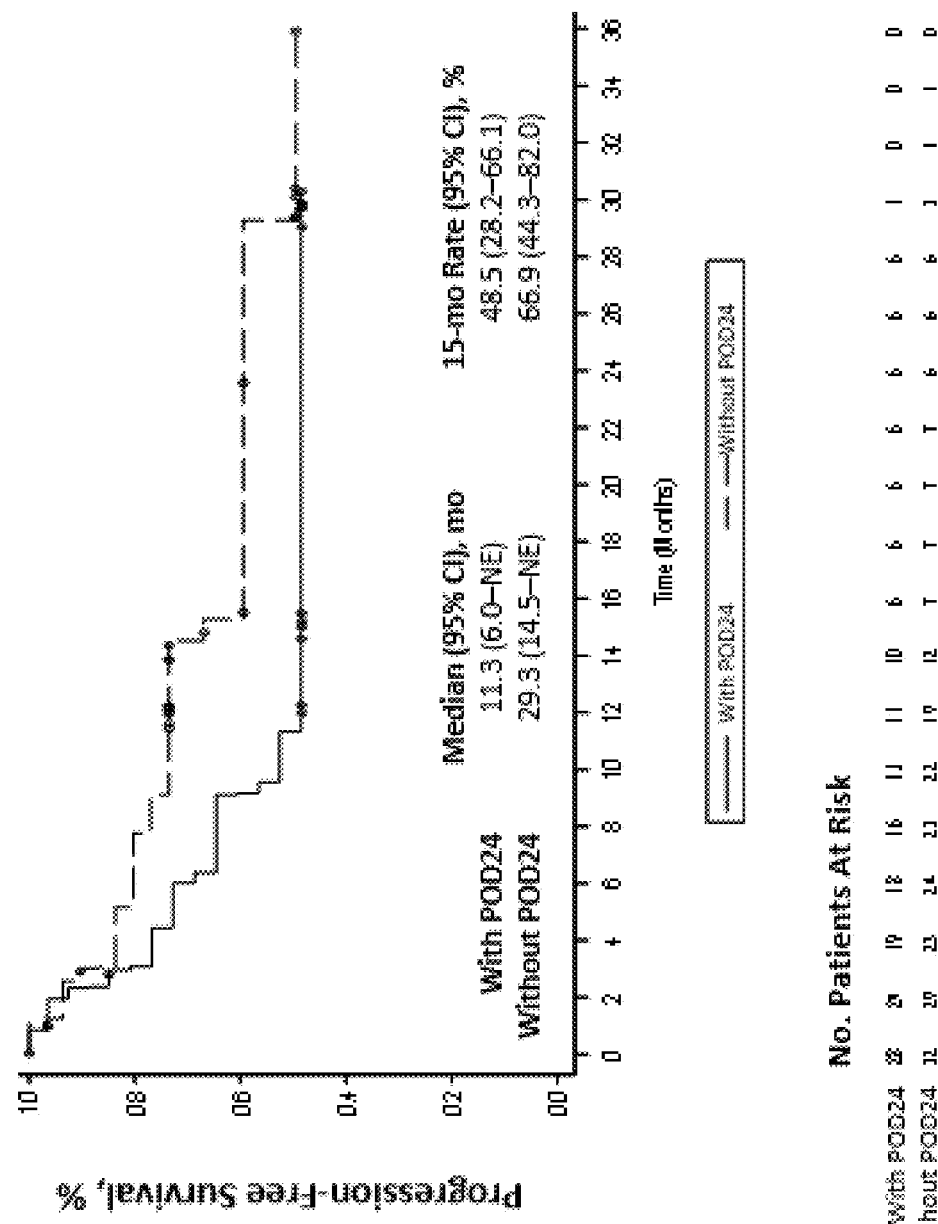
Figure 3C:
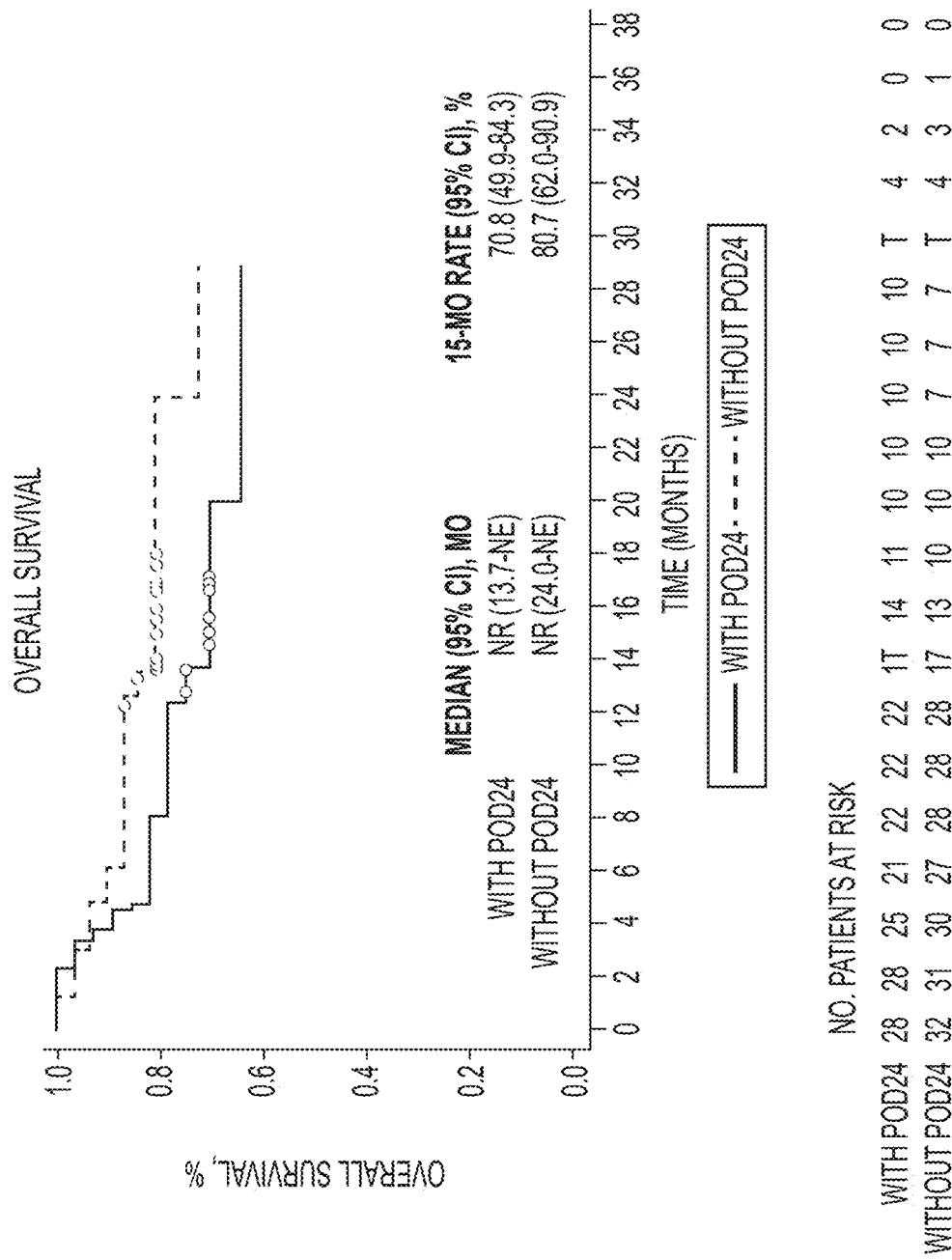

Secondary endpoints related to efficacy included duration of response (DOR), progression-free survival (PFS), and overall survival (OS). (FIG. 3). Median progression-free survival (PFS) was 11.3 months (95% CI, 6.0—NE) in patients with POD24. Median PFS appeared to be shorter among patients with POD24, compared with those without POD24. Medians for duration of response (DOR) and OS were not reached in either group (FIG. 3).

Safety profiles of patients with and without POD24 were generally similar. Incidences of Grade≥3 adverse events were generally similar in patients with and without POD24 (Table 2). Incidence of thrombocytopenia and neutropenia appeared higher in patients with POD24 than those without POD24. Incidences of infection appeared higher among patients without POD24 than those with POD24. There were no cases of Grade 5 cytokine release syndrome, KTE-X19-related secondary malignancies, or replication-competent retrovirus in either group.

TABLE 2

Summary of adverse events in patients with and without POD24.

| AE[a] | With POD24 (n = 33) | Without POD24 (n = 35) |
|---|---|---|
| Any AE, n (%) | 33 (100) | 35 (100) |
| Any Grade ≥3 | 32 (97) | 35 (100) |
| Grade ≥3 neutropenia | 30 (91) | 28 (80) |
| Grade ≥3 thrombocytopenia | 20 (61) | 16 (46) |
| Grade ≥3 anemia | 18 (55) | 18 (51) |
| Grade ≥3 infection | 8 (24) | 15 (43) |
| CRS, n (%) | 31 (94) | 31 (89) |
| Grade ≥3 | 3 (9) | 7 (20) |
| Median time to onset, days | 3 | 2 |
| Median duration, days | 8 | 12 |
| Any neurologic event, n (%) | 23 (70) | 20 (57) |
| Grade ≥3 | 9 (27) | 12 (34) |
| Median time to onset, days | 7 | 7 |
| Median duration, days | 10 | 15 |

[a]CRS was graded per Lee DW, et al. Blood. 2014; 124: 188-195. Symptoms of CRS and all other AEs were graded per National Cancer Institute's Common Terminology Criteria for Adverse Events version 4.03. AE, adverse event; CRS, cytokine release syndrome; with POD24, progression of disease <24 months after initial diagnosis; without POD24, progression of disease ≥24 months after initial diagnosis.

Figure 4:
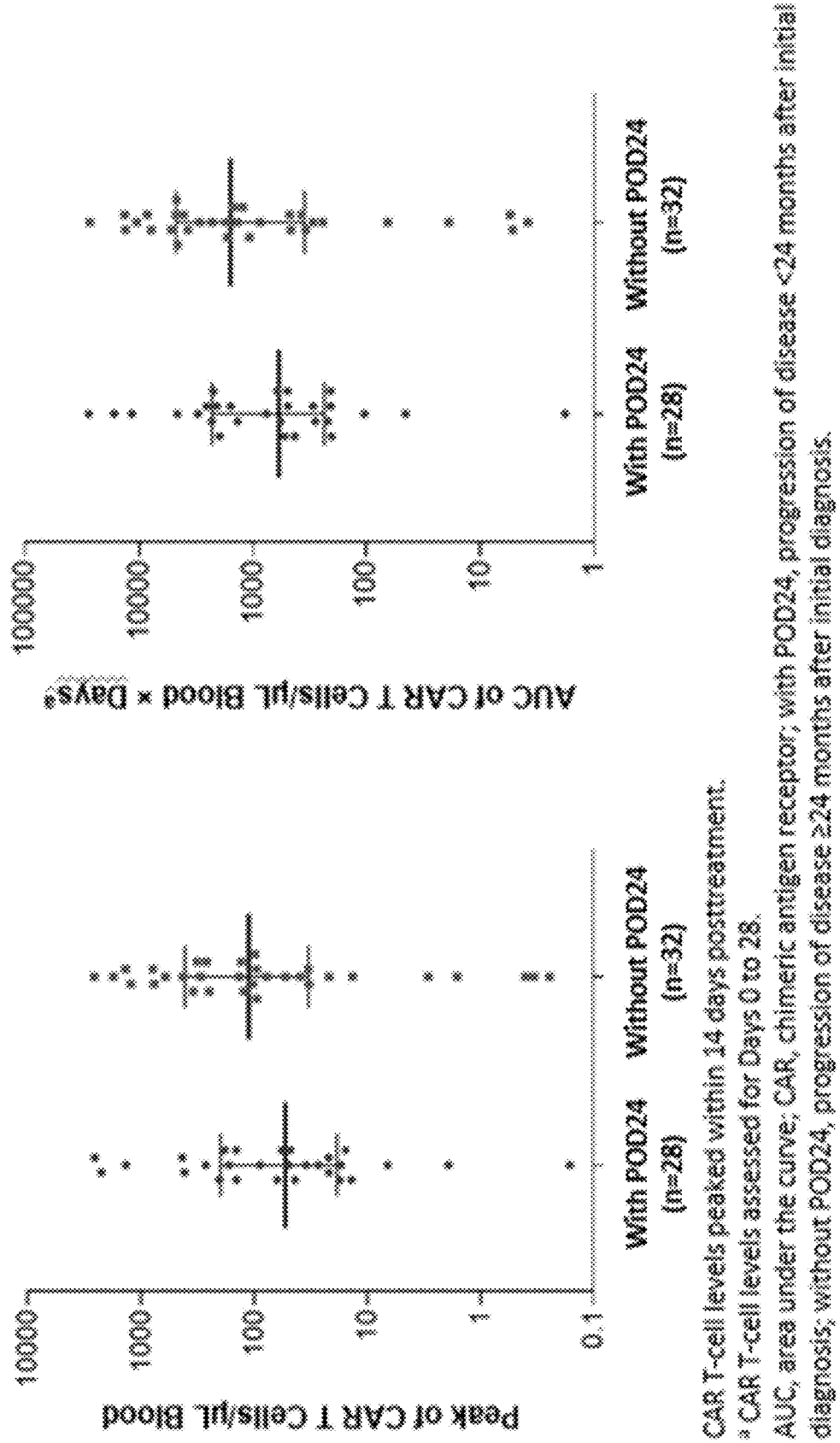
FIG. 4. CAR T-cell expansion in patients with and without MCL POD24.

Product attributes and CAR T-cell levels in blood were analyzed using previously described methods. Locke F L, et al. *Mol Ther.* 2017; 25:285-295. KTE-X19 product characteristics were similar among patients with and without POD24 (Table 3). Patients with POD24 appeared to have lower CAR T-cell expansion than those without POD24. In patients with POD24, median peak CAR T-cell levels and median area under the curve (AUC) were 53.4 cells/μL (range, 0.2-2566) and 583.4 cells/μL×days (range, 1.8-27, 743.6; FIG. 4). Patients without POD24 had median peak CAR T-cell levels and median AUC of 112.4 cells/μL (range, 0.2-2589) and 1588.3 cells/μL×days (range, 3.8-27,238.7).

TABLE 3

KTE-X19 product characteristics by POD24 status.

| Median characteristic (range) | With POD24 (n = 33) | Without POD24 (n = 35) |
|---|---|---|
| Transduction rate, % | 59.0 (34.0-82.4) | 57.2 (32.0-77.1) |
| CD4/CD8 ratio | 0.7 (0.04-3.7) | 0.7 (0.3-2.7) |

TABLE 3-continued

KTE-X19 product characteristics by POD24 status.

| Median characteristic (range) | With POD24 (n = 33) | Without POD24 (n = 35) |
|---|---|---|
| CCR7 + CD45RA + T cells, % | 26.4 (0.3-80.7) | 20.3 (3.2-78.1) |
| CCR7+ T cells, % | 41.3 (2.6-88.5) | 37.1 (16.0-88.8) |
| CCR7− effector + effector memory T cells, % | 58.9 (11.4-97.4) | 62.9 (11.1-84.1) |
| (CCR7+ T cells)/(CCR7− effector + effector memory T cells) ratio | 0.7 (0.03-7.8) | 0.6 (0.2-8.0) |
| IFN-γ by coculture, pg/mL | 6291.0 (492.0-1.8 × $10^4$) | 7120.0 (424.0-2.0 × $10^4$) |

Figure 5:
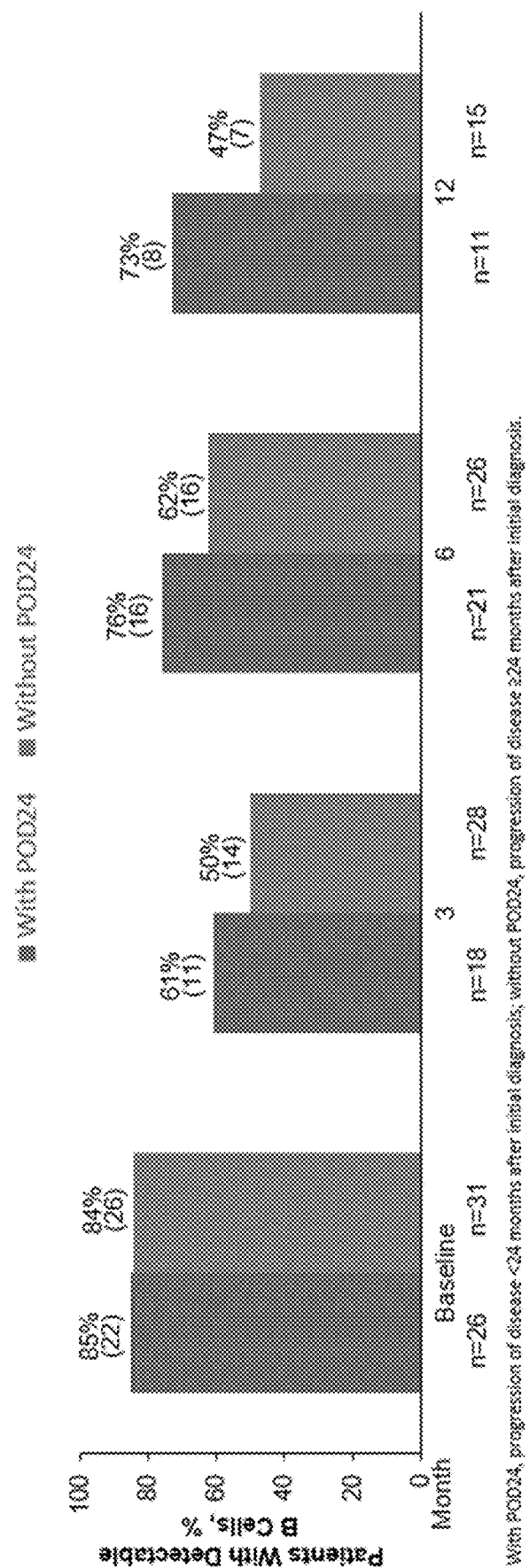
FIG. 5. Detectable B Cells Over Time Among Patients With and Without MCL POD24.

Among efficacy-evaluable patients with available data, B cells were detectable by 12 months in 8/11 (73%) patients with POD24 and 7/15 patients (47%) without POD24 (FIG. 5). Earlier intervention with CD19-directed CAR T-cell therapy may benefit patients with MCL with known high-risk factors, such as POD24. (Visco C, et al. Br J Haematol. 2019; 185:940-944).

Example 2

Figure 6:
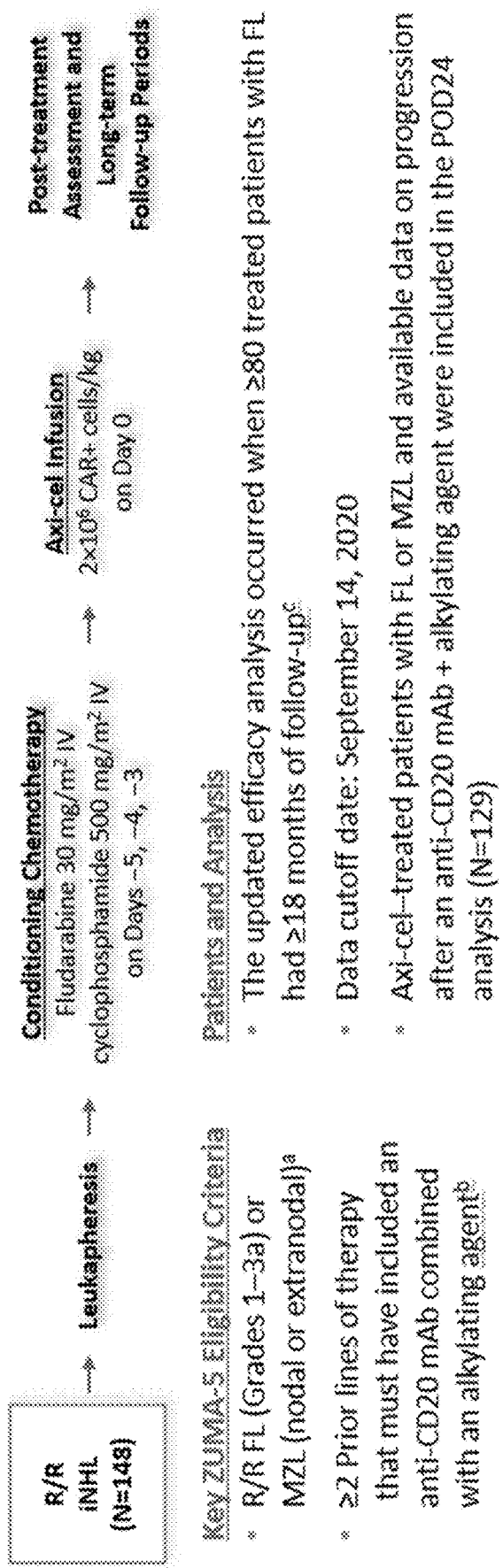
FIG. 6. Design of CLINICAL TRIAL-5 Clinical Trial. [a]Patients with stable disease (without relapse)>1 year from completion of last therapy were not eligible. [b]Single agent anti-CD20 antibody did not count as line of therapy for eligibility. [c]Efficacy-evaluable patients included ≥80 treated patients with FL who had ≥18 months of follow-up after axi-cel infusion and treated patients with MZL who had ≥4 weeks of follow-up after axi-cel infusion as of the data cutoff date. Axi-cel, axicabtagene ciloleucel; CAR, chimeric antigen receptor; FL, follicular lymphoma; iNHL, indolent non-Hodgkin lymphoma; IV, intravenous; mAb, monoclonal antibody; MZL, marginal zone lymphoma; POD24, progression of disease<24 months from initiating the first anti-CD20-containing chemoimmunotherapy; R/R, relapsed/refractory.

This example provides results from an analysis of clinical trial CLINICAL TRIAL-5, a Phase 2, multicenter, single-arm study of axicabtagene ciloleucel in patients with Relapsed/Refractory (R/R) Indolent Non-Hodgkin Lymphoma (R/R iNHL; NCT03105336). The study design for the CLINICAL TRIAL-5 trial is summarized in FIG. 6. Axicabtagene ciloleucel (axi-cel) is an autologous anti-CD19 chimeric antigen receptor (CAR) T-cell therapy approved in the United States (US) for the treatment of adults with relapsed/refractory (R/R) FL after ≥2 lines of systemic therapy, and in the US and European Union for adults with R/R large B-cell lymphoma (LBCL) after ≥2 lines of systemic therapy. (YESCARTA® (axicabtagene ciloleucel) Prescribing information. Kite Pharma, Inc; 2021; YESCARTA® (axicabtagene ciloleucel) [Summary of Product Characteristics]. Amsterdam, The Netherlands: Kite Pharma EU B.V.; 2018).

Progression within 24 months from initiating the first anti-CD20-containing chemoimmunotherapy (POD24) is a risk factor for poor survival in patients with indolent non-Hodgkin lymphoma (iNHL). (Casulo C and Barr P. Blood. 2019; 133(14):1540-154; Casulo C, et al. J Clin Oncol. 2015; 33(23): 2516-2522). Approximately 20% of patients with follicular lymphoma (FL) have POD24. In an observational analysis from the National LymphoCare Study, patients with FL who progressed early had a lower 5-year overall survival (OS) rate (50%) than those without early progression (90%). This is a report on the safety and efficacy outcomes and pharmacokinetic/pharmacodynamic profiles with longer follow-up among patients in CLINICAL TRIAL-5 with and without POD24.

Adults with follicular lymphoma (FL) (Grades 1-3a) or marginal zone lymphoma (MZL; nodal or extranodal) had R/R disease after ≥2 lines of therapy (including an anti-CD20 mAb plus an alkylating agent), and ECOG 0-1. Patients underwent leukapheresis followed by conditioning therapy (intravenous fludarabine (30 mg/m² body-surface area) and cyclophosphamide (500 mg/m² body-surface area) on days −5, −4, and −3) and a single infusion of axicabtagene ciloleucel at 2×10⁶ CAR T cells/kg on day 0. The primary endpoint was objective response rate (ORR) (Complete response (CR)+partial response (PR)) by central review (per Lugano classification; Cheson B D, et al. J Clin Oncol. 2014; 32(27):3059-3068. doi:10.1200/JCO.2013.54.8800). Secondary endpoints included complete response (CR) rate (per Lugano classification; Cheson, et al. J Clin Oncol. 2014), duration of response (DOR)(DOR is defined only for subjects who experience an objective response and is the time from the first objective response to disease progression per (Cheson et al, 2014) or disease-related death, whichever comes first), progression-free survival (PFS)(PFS is defined as the time from the axicabtagene ciloleucel infusion date to the date of disease progression per (Cheson et al, 2014) or death from any cause)), overall survival (OS)(OS is defined as the time from axicabtagene ciloleucel infusion to the date of death), incidence of adverse events (AEs), and levels of CAR T cells in blood and cytokines in serum. The primary efficacy analysis occurred when ≥80 treated patients with FL had ≥12-months follow-up. With a 17.5-month median follow-up in the primary analysis (Jacobson et al. ASH 2020. #700), 92% of patients responded (76% complete response [CR] rate). Patients with FL had lower rates of Grade≥3 neurologic events (NEs; 15%) than patients with MZL (41%). In the primary analysis, overall response rates (ORR) after a 17.5-month median follow-up were similarly high among patients with and without POD24 (93% vs 92%).

The updated efficacy analysis occurred when ≥80 treated patients with FL had ≥18 months of follow-up. Efficacy-evaluable patients included ≥80 treated patients with FL who had ≥18 months of follow-up after axicabtagene ciloleucel infusion and treated patients with MZL who had ≥4 weeks of follow-up after axicabtagene ciloleucel infusion as of the data cutoff date (Sep. 14, 2020). Axicabtagene ciloleucel-treated patients with FL or MZL and available data on progression after an anti-CD20 mAb+alkylating agent were included in the POD24 analysis (N=129).

Baseline characteristics were generally similar among patients with and without POD24 (Table 4). Among evaluable patients with FL, median tumor burden by sum of product diameters (SPD) was numerically similar in those with and without POD24 (2303 mm² vs 2839 mm²). Among evaluable patients with MZL, median SPD appeared higher among those with POD24 than without POD24 (2028 mm² vs 954 mm²).

TABLE 4

Baseline disease characteristics.

| Characteristic | With POD24 (n = 81) | Without POD24 (n = 48) |
|---|---|---|
| Disease type, n (%) | | |
| FL | 68 (84) | 40 (83) |
| MZL | 13 (16) | 8 (17) |
| Median age (range), years | 60 (34-78) | 62 (42-79) |

TABLE 4-continued

Baseline disease characteristics.

Figure 8A:
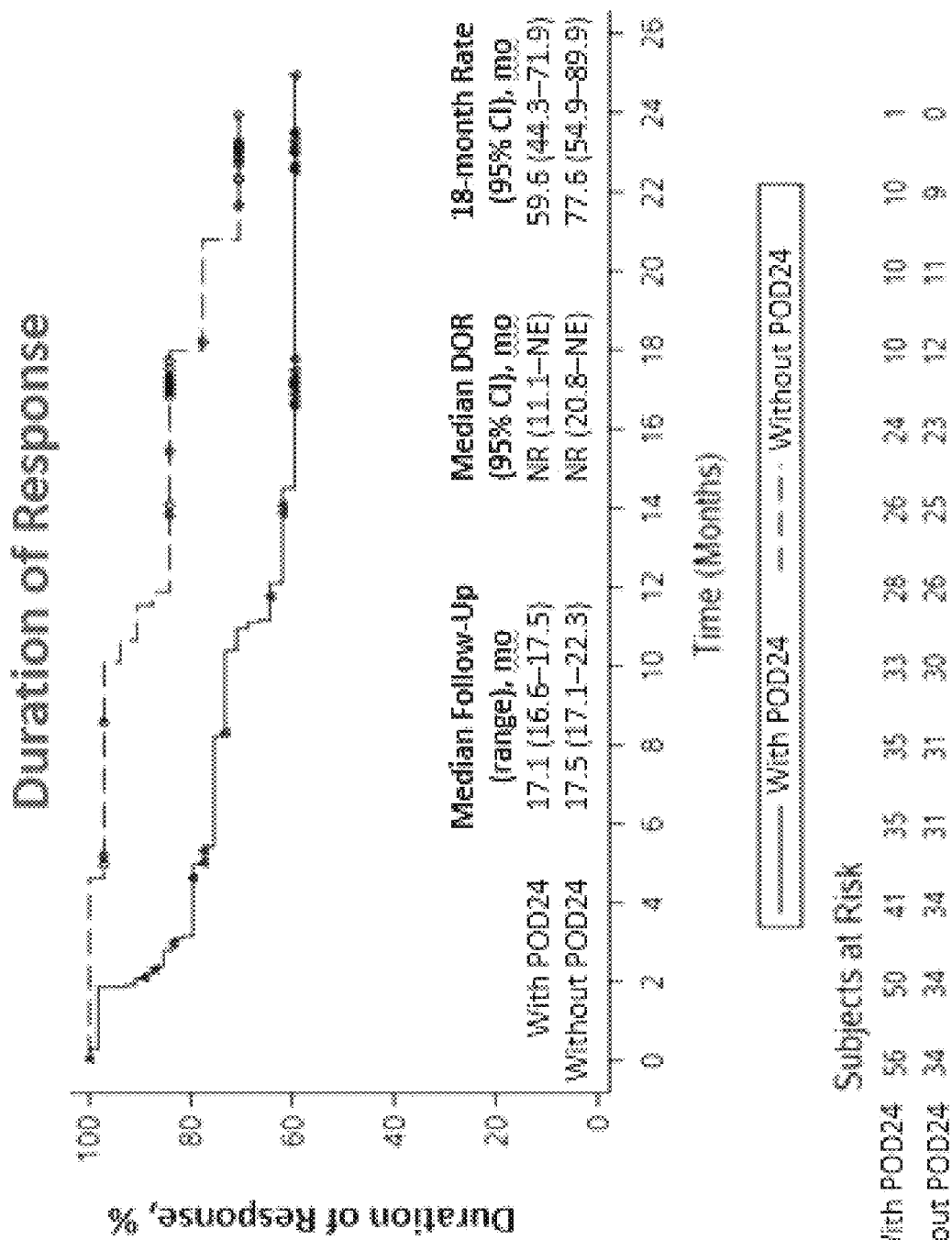
FIGS. 8A, 8B, and 8C. DOR (8A), PFS (8B), and OS (8C) by iNHL POD24 Status. DOR, duration of response; FL, follicular lymphoma; mo, month; MZL, marginal zone lymphoma; NE, not estimable; NR, not reached; OS, overall survival; PFS, progression-free survival; POD24, progression of disease<24 months from initiating the first anti-CD20-containing chemoimmunotherapy.
Figure 8B:
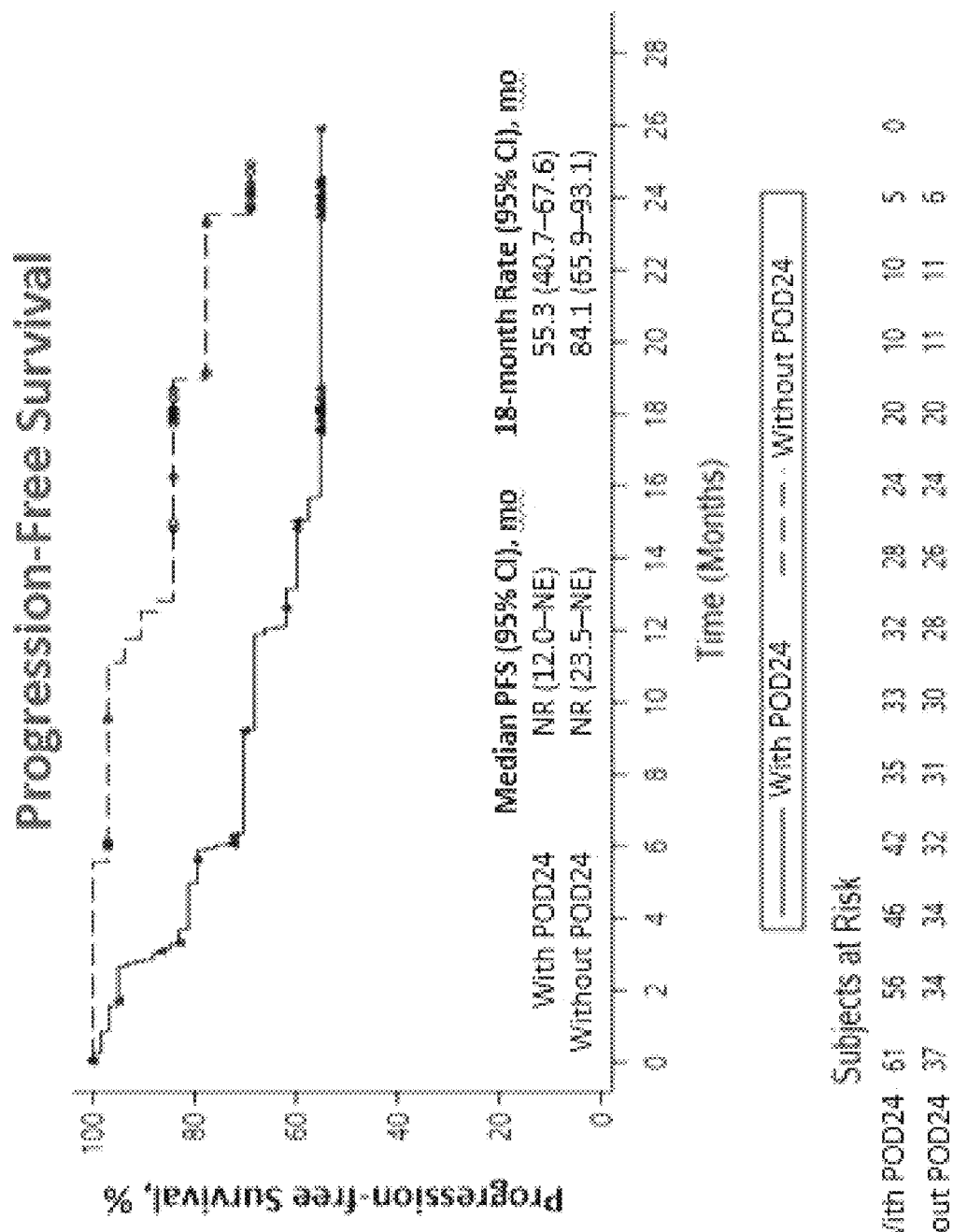
Figure 8C:
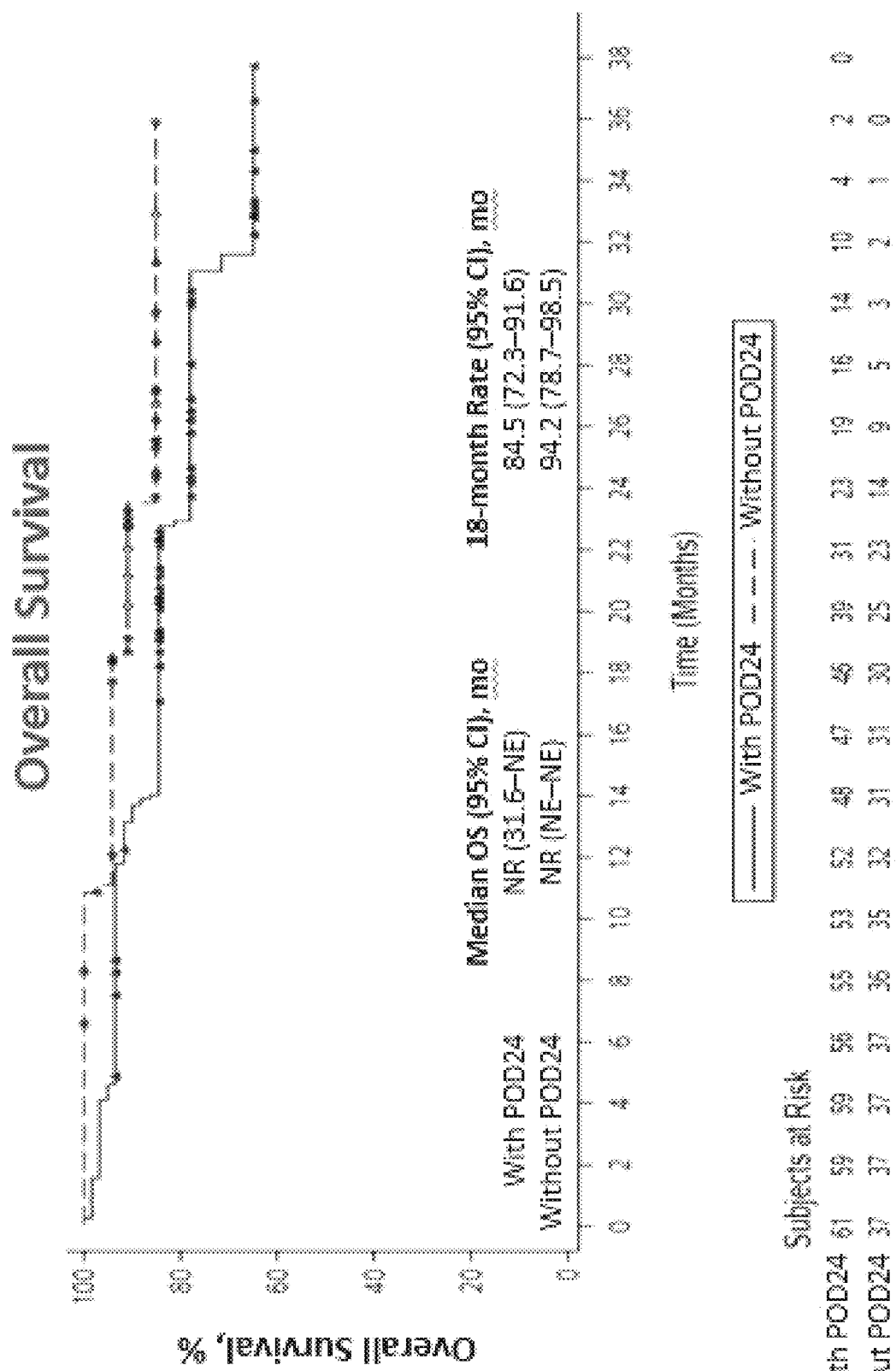

| Characteristic | With POD24 (n = 81) | Without POD24 (n = 48) |
|---|---|---|
| Disease type, n (%) | | |
| ≥65 years, n (%) | 26 (32) | 18 (38) |
| Male, n (%) | 42 (52) | 32 (67) |
| Stage III-IV disease, n (%) | 67 (83) | 45 (94) |
| ≥3 FLIPI, n/n (%) | 30/68 (44) | 17/40 (43) |
| High tumor bulk (GELF criteria), n (%)[a] | 41 (51) | 21 (44) |
| Median no. of prior therapies (range) | 3 (1-10)[b] | 3.5 (2-8) |
| ≥3, n (%) | 49 (60) | 36 (75) | estimated median duration of response (DOR) was not reached for patients with and without POD24, after a median follow-up of 17.1 months and 17.5 months, respectively (FIG. 8A, 8B, 8C; Table 5). Responses were ongoing in 52% of efficacy-evaluable patients with POD24 and 70% of those without POD24 at data cutoff. The 18-month DOR rates in patients with and without POD24 were 60% and 78%, respectively. Median progression-free survival (PFS) and median OS were not reached in patients with and without POD24 (FIG. 8B, 8C; Table 5). The 18-month PFS rates in patients with and without POD24 were 55% and 84%, respectively. The 18-month OS rates were 85% and 94%, respectively.

TABLE 5

Efficacy outcomes among patients with FL and MZL by POD24 status.

| | Follicular Lymphoma | | Marginal Zone Lymphoma | |
|---|---|---|---|---|
| Parameter | With POD24 (n = 49) | Without POD24 (n = 29) | With POD24 (n = 12) | Without POD24 (n = 8) |
| ORR, n (%) | 46 (94) | 28 (97) | 10 (83) | 6 (75) |
| CR | 38 (78) | 26 (90) | 7 (58) | 6 (75) |
| PR | 8 (16) | 2 (7) | 3 (25) | 0 (0) |
| Median DOR (95% CI), months | NR (14.5-NE) | NR (20.8-NE) | 11.1 (1.9-NE) | NR (10.6-NE) |
| 18-mo rate (95% CI), % | 63.9 (47.2-76.6) | 78.2 (53.3-90.8) | NE (NE-NE) | 75.0 (12.8-96.1) |
| Median PFS (95% CI), months | NR (13.1-NE) | NR (23.5-NE) | 9.2 (2.8-NE) | NR (11.8-NE) |
| 18-mo rate (95% CI), % | 59.8 (43.7-72.6) | 85.3 (65.4-94.2) | 30.7 (5.1-62.6) | 75.0 (12.8-96.1) |
| Median OS (95% CI), months | NR (31.6-NE) | NR (NE-NE) | NR (13.7-NE) | NR (18.7-NE) |
| 18-mo rate (95% CI), % | 85.7 (72.4-92.9) | 93.1 (75.1-98.2) | 76.4 (30.9-94.0) | 100.0 (NE-NE) |

CR, complete response; DOR, duration of response; FL, follicular lymphoma; mo, month; MZL, marginal zone lymphoma; ND, not done/undefined; NE, not estimable; NR, not reached; OS, overall survival; PFS, progression-free survival; POD24, progression of disease <24 months from initiating the first anti-CD20-containing chemoimmunotherapy; PR, partial response.

TABLE 4-continued

Baseline disease characteristics.

| Characteristic | With POD24 (n = 81) | Without POD24 (n = 48) |
|---|---|---|
| Disease type, n (%) | | |
| Prior PI3Ki therapy, n (%) | 22 (27) | 17 (35) |
| Prior lenalidomide, n (%) | 25 (31) | 19 (40) |
| Prior autologous SCT, n (%) | 16 (20) | 11 (23) |
| Refractory disease, n (%)[c] | 62 (77) | 30 (63) |

[a]Disease burden, as defined by GELF criteria: involvement of ≥3 nodal sites (≥3 cm diameter each); any nodal or extranodal tumor mass with ≥7 cm diameter; B symptoms; splenomegaly; pleural effusions or peritoneal ascites; cytopenias; or leukemia.
[b]Enrollment of 3 patients with FL who had 1 prior line of therapy occurred in CLINICAL TRIAL-5 before a protocol amendment requiring ≥2 prior lines of therapy.
[c]Patients with iNHL who progressed within 6 months of completion of the most recent prior treatment. FL, follicular lymphoma; FLIPI, Follicular Lymphoma International Prognostic Index; GELF, Groupe d'Etude des Lymphomes Folliculaires; MZL, marginal zone lymphoma; PI3Ki, phosphoinositide 3-kinase inhibitor; POD24, progression of disease <24 months from initiating the first anti-CD20-containing chemoimmunotherapy; SCT, stem cell transplantation.

Figure 7:
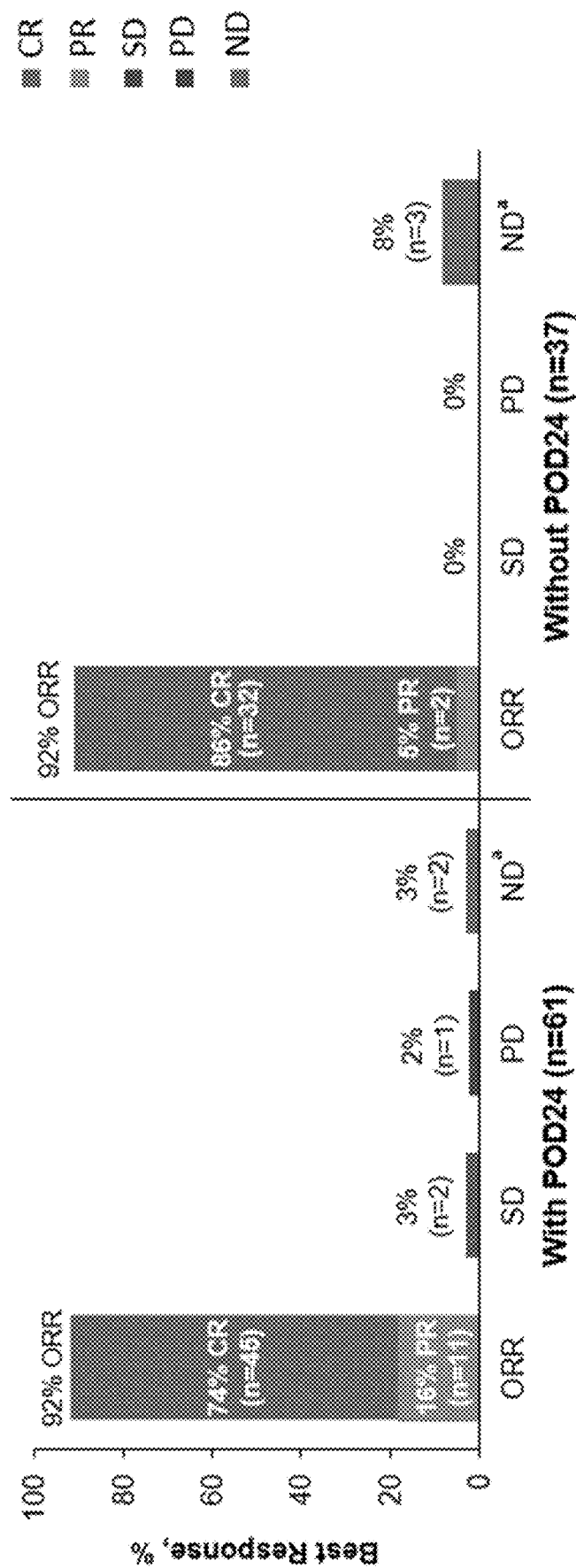
FIG. 7. ORR by IRRC Assessment in Patients With and Without iNHL POD24. Assessed by an IRRC according to the Lugano Classification. (Cheson B D, et al. *J Clin Oncol.* 2014; 32:3059-68). [a] Among the 5 patients reported as ND, 4 (1 FL without POD24; 3 MZL) had no disease at baseline and postbaseline per IRRC but were considered with disease by the investigator; 1 patient with FL and POD24 died before the first disease assessment. CR, complete response; FL, follicular lymphoma; IRRC, Independent Radiology Review Committee; MZL, marginal zone lymphoma; ND, not done/undefined; ORR, overall response rate; iNHL POD24, progression of disease<24 months from initiating the first anti-CD20-containing chemoimmunotherapy; PD, progressive disease; PR, partial response; SD, stable disease.

Secondary endpoints related to efficacy included duration of response (DOR), progression-free survival (PFS), and overall survival (OS). The overall response rate (ORR; CR and partial response) was assessed by an independent radiology review committee per the Lugano classification. Cheson B D et al., *Journal of clinical oncology* 2014; 32:3059-68. The ORR was similar among efficacy-evaluable patients with and without POD24 (FIG. 7; Table 5). The Incidences of Grade≥3 adverse events were generally similar in patients with and without POD24 (Table 6). Grade 5 events occurred in 3 patients with POD24, including 1 event in the context of cytokine release syndrome (CRS); no Grade 5 events occurred in patients without POD24. Grade 4 CRS occurred in 1 patient with POD24. Grade 4 neurologic events occurred in 2 patients with POD24. In patients without POD24, no Grade 4 CRS or neurologic events occurred.

CAR T cell levels in blood, cytokine levels in serum, and product attributes, and their associations with clinical outcomes, were analyzed by using previously described methods. Locke F L, et al. *Mol Ther.* 2017; 25:285-295.

Figure 9A:
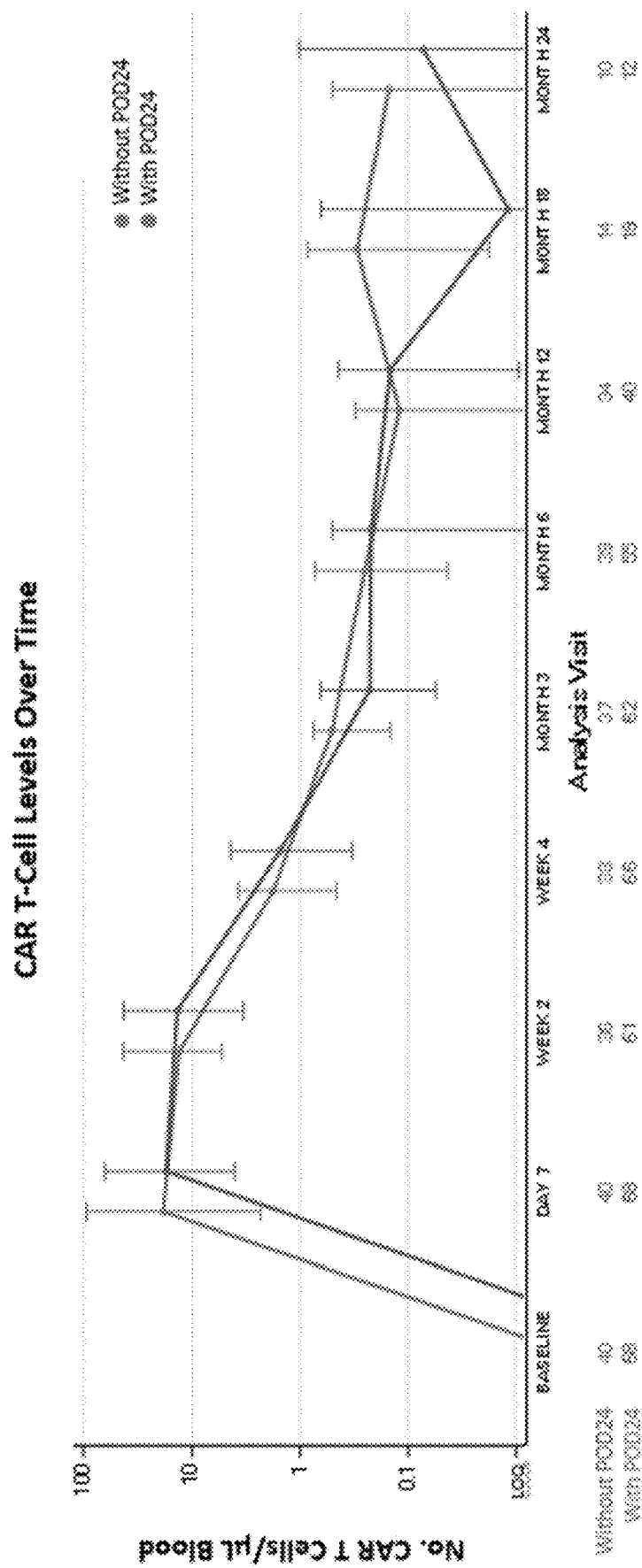
FIGS. 9A, 9B, and 9C. CAR T-Cell Expansion (9A and 9B) and Pretreatment Serum Analytes in Patients (9C) With FL by iNHL POD24 Status. P values were calculated using the Wilcoxon rank sum test.[a] Data were not available for 2 patients with FL before retreatment. $AUC_{0-28}$, area under the curve between Day 0 and Day 28; CAR, chimeric antigen receptor; CCL, chemokine (C-C motif) ligand; FL, follicular lymphoma; LOQ, limit of quantification; MDC, macrophage-derived chemokine; POD24, progression of disease<24 months from initiating the first anti-CD20-containing chemoimmunotherapy; TARC; thymus- and activation-regulated chemokine.
Figure 9B:
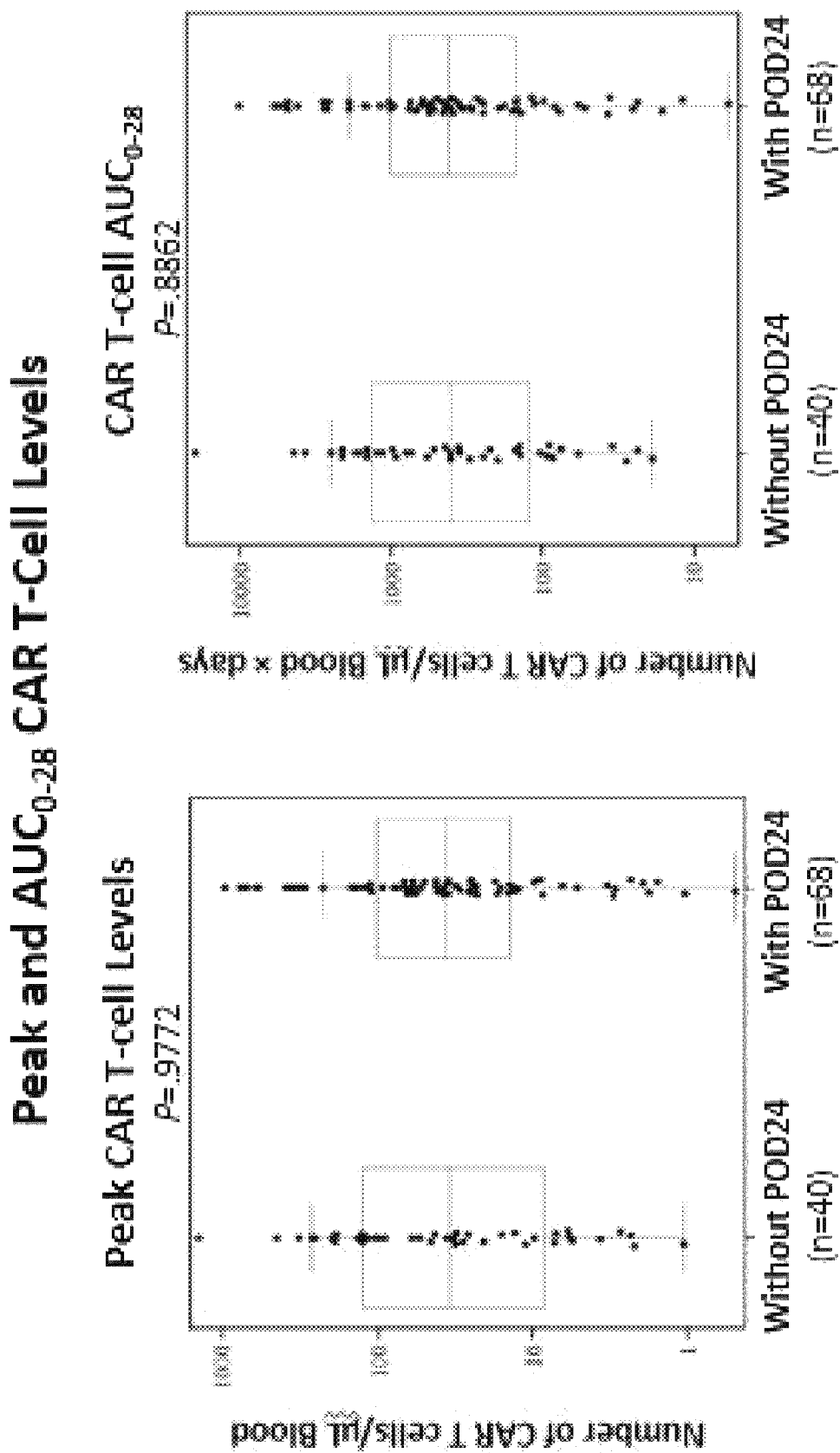
Figure 9C:
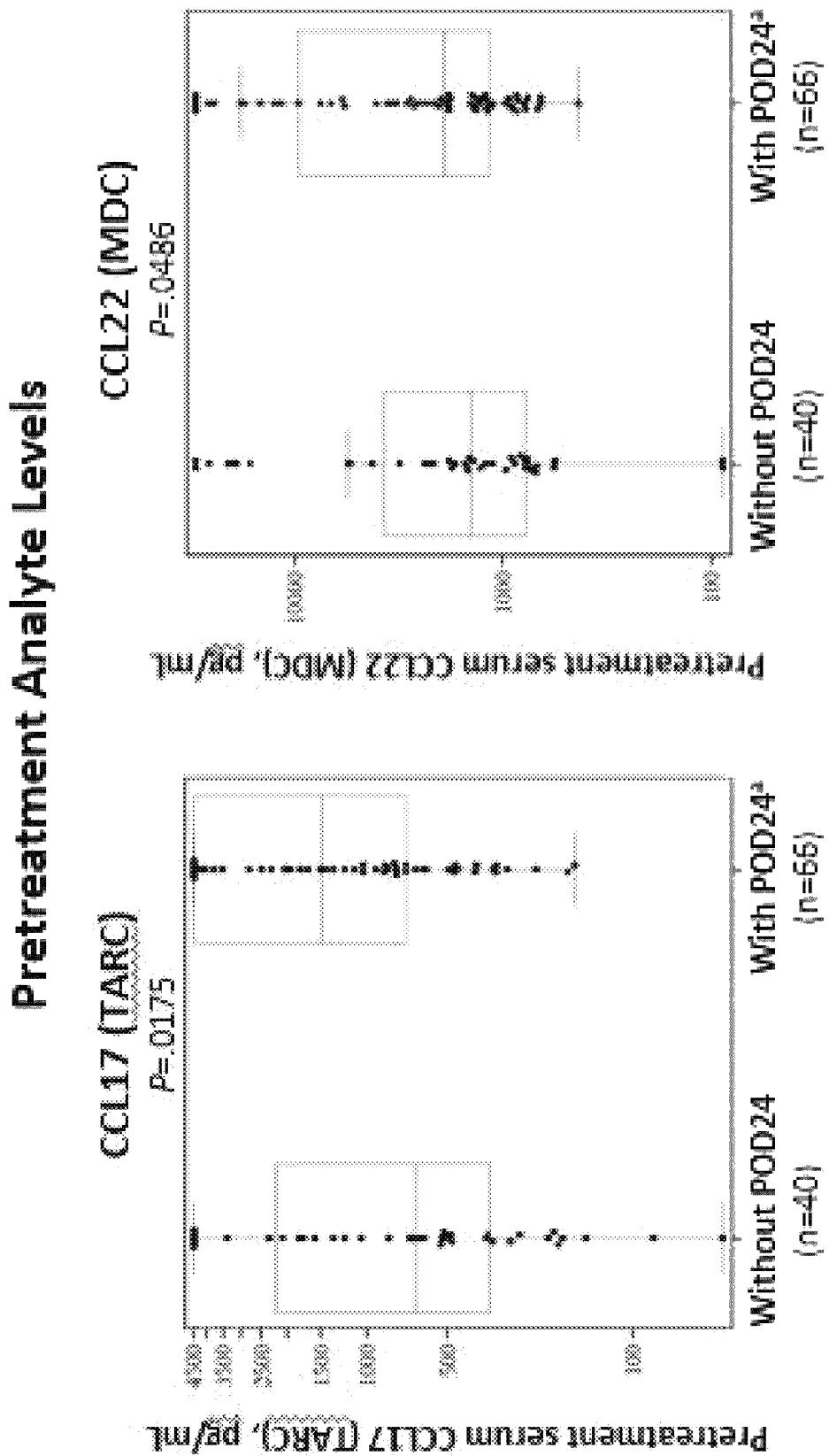

In efficacy-evaluable patients with FL, median peak CAR T-cell levels were similar in patients with and without POD24 (36.9 cells/µL and 34.5 cells/µL, respectively; FIG. 9A). Median AUCs were also similar among patients with and without POD24 (422.5 cells/µL×days and 407.6 cells/µL×days, respectively. (FIG. 9B). Pretreatment levels of CCL17 (TARC) and CCL22 (MDC) were higher in patients with POD24 than without POD24. Peak levels of biomarkers associated with axicabtagene ciloleucel toxicity appeared generally similar in all treated patients with and without POD24 (Table 7). Pharmacokinetic/pharmacodynamic findings between groups were similar in patients with MZL.

TABLE 7

Peak cytokine levels in patients with FL by POD24 status.

| Peak Cytokine Levels (Range) | With POD24 (n = 68) | Without POD24 (n = 40) | P value |
|---|---|---|---|
| IL-6, pg/mL | 15.0 (1.6$^a$-976.0$^b$) | 13.0 (1.6$^a$-976.0$^b$) | .7574 |
| IL-2, pg/mL | 3.2 (0.9$^a$-90.6) | 2.7 (0.9$^a$-63.7) | .6181 |
| IFN-γ, pg/mL | 122.8 (7.5$^a$-1876.0$^b$) | 67.8 (7.5$^a$-1545.1) | .0789 |
| Granzyme B, pg/mL | 7.8 (1.0$^a$-1062.7) | 8.2 (1.0$^a$-449.4)$^c$ | .9447 |
| CXCL10, pg/mL | 1001.9 (264.4-2000.0$^b$) | 1093.2 (165.9-2000.0$^b$) | .5385 |
| IL-10, pg/mL | 10.7 (0.7$^a$-331.5) | 7.4 (0.7$^a$-66.5) | .2255 |
| TNF-α, pg/mL | 4.6 (1.6-62.7) | 4.1 (0.7$^a$-11.0) | .1644 |
| IL-1RA, pg/mL | 1202.0 (221.0-9000.0$^b$) | 982.5 (239.0-9000.0$^b$) | .2983 |
| GM-CSF, pg/mL | 1.9$^a$ (1.9$^a$-23.2) | 1.9$^a$ (1.9$^a$-34.1) | .7177 |
| CCL2 (MCP-1), pg/mL | 790.1 (249.3-1500.0$^b$) | 829.2 (249.4-1500.0$^b$) | .9975 |
| IL-15, pg/mL | 33.8 (9.3-93.3) | 34.5 (12.0-104.3) | .5908 |
| Ferritin, ng/mL | 720.2 (86.4-5237.8) | 658.9 (91.3-3459.9) | .4900 |
| SAA, pg/mL | 1.5 × 10$^8$ (1.5 × 10$^6$-1.4 × 10$^{9b}$) | 1.7 × 10$^8$ (4.9 × 10$^6$-1.4 × 10$^{9b}$) | .9695 |
| CRP, mg/L | 68.3 (3.9-496.0$^b$) | 71.2 (2.9-377.8) | .8164 |

P values were calculated using the Wilcoxon rank sum test.
$^a$Lower limit of quantification in assay used.
$^b$Upper limit of quantification in assay used.
$^c$Data were not available for 2 patients with FL at peak. CCL, chemokine (C-C motif) ligand; CRP, C-reactive protein; CXCL, C-X-C motif chemokine ligand; FL, follicular lymphoma; GM-CSF, granulocyte-macrophage colony-stimulating factor; IFN, interferon; IL, interleukin; MCP-1, monocyte chemoattractant protein 1; POD24, progression of disease <24 months from initiating the first anti-CD20-containing chemoimmunotherapy; RA, receptor agonist; SAA, serum amyloid A; TNF, tumor necrosis factor.

Of the 14 patients (13 FL; 1 MZL) in broader CLINICAL TRIAL-5 population with available data at relapse after axicabtagene ciloleucel, 100% had detectable CD19. Detectable CD19 was confirmed in all evaluable biopsies from patients with and without POD24. Axicabtagene ciloleucel product attributes were generally similar among patients with and without POD24 (Table 8).

TABLE 8

Axicabtagene ciloleucel product characteristics in patients with FL by POD24 status.

| Characteristic (range) | With POD24 (n = 68) | Without POD24 (n = 40) |
|---|---|---|
| No. CCR7 + CD45RA + T cells, 10$^6$ | 38.5 (6.4-268.6)$^a$ | 46.6 (1.1-296.6)$^a$ |
| CD4/CD8 ratio | 0.7 (0.1-31.3)$^a$ | 0.8 (0.1-13.1)$^a$ |
| Transduction rate, % | 60.5 (18.0-86.0) | 60.5 (26.0-77.0) |
| IFN-γ in coculture, pg/mL | 5511.0 (753.0-1.9 × 10$^4$) | 6315.0 (1267.0-1.8 × 10$^4$) |

$^a$Based on available data: with POD24, n = 57; without POD24, n = 36 (CCR7 + CD45RA+ cells) and n = 35 (CD4/CD8 ratio). Axi-cel, axicabtagene ciloleucel; FL, follicular lymphoma; IFN, interferon; POD24, progression of disease <24 months from initiating the first anti-CD20-containing chemoimmunotherapy.

Axicabtagene ciloleucel showed a high rate of durable responses in patients with POD24 iNHL. Although medians for PFS were not reached in either group, estimated PFS rates at 18 months appeared lower in patients with POD24 than those without POD24. Among patients with FL, higher pretreatment levels of analytes previously associated with relapse (CC17 [TARC] and CCL22 [MDC] (Plaks V, et al. AACR 2021. #CT036)) were observed in patients with POD24 than without POD24, potentially contributing to differences in the 18-month PFS rate. Safety profiles were similarly manageable in patients with and without POD24. Among patients with FL, post-treatment pharmacokinetic and pharmacodynamic profiles appeared largely comparable in patients with and without POD24. Axicabtagene ciloleucel may be a promising option for patients with POD24 iNHL, a population with particularly high-risk disease.

Example 3

This example characterized two anti-CD19 CAR T therapies, KTE-X19 and axicabtagene ciloleucel. The manufacturing process of KTE-X19 was modified relative to that of axicabtagene ciloleucel to remove circulating lymphoma cells through positive enrichment for CD4$^+$/CD8$^+$ cells. Cells were labeled with fluorescently-conjugated antibodies to CD3 (pan T cell marker), CD14, CD19 (B cell marker), CD45 (pan-leukocyte marker), and CD56 (activation and NK marker) and assessed by flow cytometry. Cell viability was assessed using negative staining of a viability dye (SYTOX near-IR). The lower limit of quantification (LLOQ) of the assay was 0.2% and for NK cells and monocytes was 5%. The percentage of NK cells was determined (NK cells were CD45$^+$, CD14$^-$, CD3$^-$, and CD56$^+$; T cells were CD45$^+$, CD14$^-$, and CD3$^-$). The median percentages of NK cells from 23 lots of axicabtagene ciloleucel and 97 lots of KTE-X19 were 1.9% (range 0.8%-3.2%) and 0.1% (range 0.0%-2.8%), respectively. The median percentage of CD3$^-$ cellular impurities from the same lots of axicabtagene ciloleucel and KTE-X19 were 2.4% (range 0.9%-4.6%) and 0.5% (range 0.3%-3.9%), respectively. The results of KTE-X19 (brexucabtagene autoleucel, TECARTUS) and axicabtagene ciloleucel (YESCARTA) in cell viability were ≥72% and ≥80%, respectively; in anti-CD19 CAR expression were ≥24% and ≥15%, respectively; in IFN-γ production were ≥190 pg/mL and ≥520 pg/mL, respectively; and in percentage of CD3$^+$ cells were ≥90% and ≥85%, respectively. Brexucabtagene autoleucel is predominantly composed of CD3+ T cells (99.3%±0.8%), which can be further delineated into the CD4+ (37.9%±16.5%) and CD8+ (59.3%±16.5%) subsets. The presence of circulating lymphoma cells may have a role in manufacturing failures and also exhaustion of anti-CD19 CAR T cells during ex vivo manufacturing.

Example 4

This Example refers to the 3-year results for CLINICAL TRIAL-4 (NCT02625480), a phase 1/2 multicenter study evaluating the safety and efficacy of KTE-X19, an autologous anti-CD19 chimeric antigen receptor (CAR) T-cell therapy (described above), in pediatric/adolescent patients with relapsed/refractory (R/R) B-cell acute lymphoblastic leukemia (B-ALL; median follow-up for all treated patients: 36.1 months). Two formulations were explored in phase 1 for patients receiving the lower dose of $1\times10^6$ chimeric antigen receptor (CAR) T cells/kg, one with a total volume of 40 mL and the other with a volume of 68 mL. The 40 mL formulation was intended to maintain cell density and cell viability during the freezing/thawing process. For patients weighing>100 kg, a maximum flat dose of $2\times10^8$ or $1\times10^8$ anti-CD19 CAR T cells was administered. The primary endpoint was the incidence of dose-limiting toxicities (DLTs). Of 31 enrolled patients, KTE-X19 was administered to 24 (median age 13.5 years, range 3-20) and median follow-up was 36.1 months. No DLTs were observed. All treated patients had grade≥3 adverse events, commonly hypotension (50%) and anemia (42%). Rates of grade 3 cytokine release syndrome were 33%, 75%, 27%, and 22% in the all-treated, $2\times10^6$, $1\times10^6$ (68 mL formulation), and $1\times10^6$ (40 mL formulation) CAR T cells/kg groups; 21%, 25%, 27%, and 11% of patients experienced grade≥3 neurologic events, respectively. The overall complete remission (CR) rates (CR and CR with incomplete hematologic recovery) were 67%, 75%, 64%, and 67% in the all-treated, $2\times10^6$, $1\times10^6$ (68 mL), and $1\times10^6$ (40 mL) CAR T cells/kg groups, respectively. Overall MRD-negativity rates were 100% among responders. In the $1\times10^6$ (40 mL) group (recommended phase 2 dose), median duration of remission and overall survival were not reached. Pediatric/adolescent patients with R/R B-ALL achieved high MRD-negative remission rates with a manageable safety profile after a single dose of KTE-X19. Phase 2 is ongoing at the $1\times10^6$ CAR T cells/kg (40 mL) dose.

In the phase 1 portion of CLINICAL TRIAL-4, eligible patients were ≤21 years of age with ≥6 kg body weight and R/R B-ALL only, defined as refractory to first-line therapy, R/R after ≥2 lines of systemic therapy, or R/R after alloSCT if the patient was ≥100 days from alloSCT at the time of enrollment and off immunosuppressive medications for ≥4 weeks prior to enrollment. Prior treatment with blinatumomab was allowed. Dose-limiting toxicities (DLTs) were defined as follows: Grade 4 hematologic toxicity lasting more than 30 days (except lymphopenia) if not attributable to underlying disease; all KTE-X19-related grade 3 non-hematologic toxicities lasting >7 days; and all KTE-X19-related grade 4 non-hematologic toxicities regardless of duration with the exceptions noted in Table 9. Specified bridging chemotherapy was permitted after leukapheresis and completed at least 7 days or 5 half-lives, whichever was shorter, prior to initiating conditioning chemotherapy consisting of intravenous (IV) fludarabine 25 mg/m²/day on days −4, −3, and −2, and a single dose of IV cyclophosphamide 900 mg/m² on day −2. A single IV infusion of KTE-X19 was administered on day 0 at a target dose of $2\times10^6$ or $1\times10^6$ CART cells/kg. Hospitalization post-infusion was required for a minimum of 7 days. All patients completing the month 3 visit were followed in the long-term follow-up period for survival and disease status every 3 months through month 18, every 6 months from months 24 to 60, then once annually for up to 15 years. Patients could be removed from the study if they withdrew consent for further follow-up, were lost to follow-up, or died. Allogeneic stem cell transplant (alloSCT) was not required per the protocol but was allowed per investigator discretion.

Additional Phase 1 Inclusion Criteria

Morphological disease with >5% bone marrow blasts:
1. Lansky or Karnofsky performance status≥80% at screening
2. Patients with Philadelphia chromosome-positive disease were also eligible if they were intolerant to tyrosine kinase inhibitor therapy or if they had R/R disease despite treatment with at least two different tyrosine kinase inhibitors (TKI)
3. In patients previously treated with blinatumomab, leukemic blasts with CD19 expression≥90% was required
4. Absolute neutrophil count (ANC)≥500/μL unless in the opinion of the primary investigator cytopenia is due to underlying leukemia and is potentially reversible with leukemia therapy
5. Platelet count≥50,000/μL unless, in the opinion of the principal investigator, cytopenia is due to underlying leukemia and is potentially reversible with leukemia therapy
6. Absolute lymphocyte count≥100/μL
7. Adequate renal, hepatic, pulmonary and cardiac function were defined as:
   a. Creatinine clearance (as estimated by Cockcroft Gault or Schwartz)≥60 cc/min
   b. Serum alanine aminotransferase and aspartate aminotransferase≤5× upper limit of normal (ULN)
   c. Total bilirubin≤1.5×ULN, except in patients with Gilbert's syndrome
   d. Left ventricular shortening fraction≥30% or left ventricular ejection fraction≥50%, no evidence of pericardial effusion as determined by an echocardiogram, and no clinically significant arrhythmias
   e. No clinically significant pleural effusion
   f. Baseline oxygen saturation≥92% on room air
8. Females of childbearing potential (defined as having first menses) must have a negative serum or urine pregnancy test Additional Phase 1 Exclusion Criteria
1. Burkitt leukemia/lymphoma according to World Health Organization classification or chronic myelogenous leukemia lymphoid blast crisis
2. History of malignancy other than nonmelanoma skin cancer or carcinoma in situ unless disease-free for ≥3 years
3. History of severe hypersensitivity reaction to aminoglycosides or any of the agents used in this study
4. History or presence of any central nervous system (CNS) disorder, such as a seizure disorder, cerebrovascular ischemia/hemorrhage, dementia, cerebellar disease, any autoimmune disease with CNS involvement, posterior reversible encephalopathy syndrome, or cerebral edema
   a. Detectable cerebrospinal blast cells in a sample of cerebrospinal fluid with <5 white blood cells per mm3 with neurological changes (CNS-2), or detectable cerebrospinal blast cells in a sample of cerebrospinal fluid with ≥5 white blood cells per mm3 with or without neurological changes (CNS-3) were also excluded
5. History of concomitant genetic syndrome associated with bone marrow failure such as Fanconi anemia, Kostmann syndrome, or Shwachman-Diamond syndrome
6. History of myocardial infarction, cardiac angioplasty or stenting, unstable angina, or other clinically significant cardiac disease within 12 months of enrollment
7. History of symptomatic deep vein thrombosis or pulmonary embolism within 6 months of enrollment
8. Primary immunodeficiency
9. Known infection with HIV, hepatitis B or hepatitis C virus. A history of hepatitis B or hepatitis C is permitted if the viral load is undetectable per quantitative polymerase chain reaction (PCR) and/or nucleic acid testing
10. Presence of fungal, bacterial, viral, or other infection that is uncontrolled or requiring IV antimicrobials for management. Simple urinary tract infections and uncomplicated bacterial pharyngitis are permitted if responding to active treatment and after consultation with the Kite Medical Monitor
11. Prior medication
   a. Salvage systemic therapy (including chemotherapy, TKIs for Ph+ ALL, and blinatumomab) within 1 week or 5 half-lives (whichever is shorter) prior to enrollment
   b. Prior CD19 directed therapy other than blinatumomab
   c. History of Common Terminology Criteria for Adverse Events Grade 4 neurologic event or grade 4 CRS (per Lee et al 2014) with prior CD19-directed therapy
   d. Alemtuzumab within 6 months prior to enrollment, clofarabine or cladribine within 3 months prior to enrollment, or PEG-asparaginase within 3 weeks prior to enrollment
   e. Donor lymphocyte infusion within 28 days prior to enrollment
   f. Any drug used for graft-versus-host disease (GVHD) within 4 weeks prior to enrollment (eg, calcineurin inhibitors, methotrexate, mycophenolate, rapamycin, thalidomide) or immunosuppressive antibody such within 4 weeks prior to enrollment (eg, anti-CD20, anti-tumor necrosis factor, anti-interleukin 6 or anti-interleukin 6 receptor)
   g. At least 3 half-lives must have elapsed from any prior systemic inhibitory/stimulatory immune checkpoint molecule therapy prior to enrollment (eg, ipilimumab, nivolumab, pembrolizumab, atezolizumab, OX40 agonists, 4-1BB agonists)
   h. Corticosteroid therapy at a pharmacologic dose (≥0.7 mg/kg/day of hydrocortisone or equivalent doses of corticosteroids) and other immunosuppressive drugs must be avoided for 7 days prior to enrollment
12. Presence of any indwelling line or drain (eg, percutaneous nephrostomy tube, indwelling Foley catheter, biliary drain, or pleural/peritoneal/pericardial catheter). Ommaya reservoirs and dedicated central venous access catheters such as a Port-a-Cath or Hickman catheter are permitted
13. Acute GVHD grade II-IV by Glucksberg criteria or severity B-D by International Bone Marrow Transplant Registry index; acute or chronic GVHD requiring systemic treatment within 4 weeks prior to enrollment
14. Live vaccines≤4 weeks prior to enrollment
15. Females of childbearing potential who are pregnant or breastfeeding because of the potentially dangerous effects of the preparative chemotherapy on the fetus or infant
16. Patients of both genders of childbearing potential who are not willing to practice birth control from the time of consent through 6 months after the completion of KTE-X19
17. In the investigator's judgment, the subject is unlikely to complete all protocol-required study visits or procedures, including follow-up visits, or comply with the study requirements for participation
18. History of autoimmune disease (eg, Crohns, rheumatoid arthritis, systemic lupus) resulting in end organ injury or requiring systemic immunosuppression/systemic disease modifying agents within the last 2 years.

The study design and treatment were as follows: the phase 1 objective was to evaluate safety of KTE-X19 and determine the recommended phase 2 dose (RP2D) of KTE-X19 based on the incidence of dose-limiting toxicities (DLT) and the overall safety profile. DLT were defined as: Grade 4 hematologic toxicity lasting more than 30 days (except lymphopenia) if not attributable to underlying disease; all KTE-X19-related grade 3 non-hematologic toxicities lasting >7 days; and all KTE-X19-related grade 4 non-hematologic toxicities regardless of duration with the exceptions noted in Table 9. Specified bridging chemotherapy was permitted after leukapheresis and completed at least 7 days or 5 half-lives, whichever was shorter, prior to initiating conditioning chemotherapy consisting of intravenous (IV) fludarabine 25 mg/m$^2$/day on days −4, −3, and −2, and a single dose of IV cyclophosphamide 900 mg/m2 on day −2. A single IV infusion of KTE-X19 was administered on day 0 at a target dose of 2×10$^6$ or 1×10$^6$ CAR T cells/kg. Hospitalization post-infusion was required for a minimum of 7 days. All patients completing the month 3 visit were followed in the long-term follow-up period for survival and disease status every 3 months through month 18, every 6 months from months 24 to 60, then once annually for up to 15 years. Patients could be removed from the study if they withdrew consent for further follow-up, were lost to follow-up, or died. Allogeneic stem cell transplant (alloSCT) was not required per the protocol but was allowed per investigator discretion.

TABLE 9

Criteria for dose-limiting toxicities

DLTs were defined as the following KTE-X19-related events with onset within the first 28 days following KTE-X19 infusion:
Grade 4 hematologic toxicity lasting more than 30 days (except lymphopenia) if not attributable tunderlying disease
All KTE-X19-related grade 3 non-hematologic toxicities lasting for >7 days and all KTE-X19-related grade 4 non-hematologic toxicities regardless of duration are considered DLTs, with the exception of the following:

TABLE 9-continued

Criteria for dose-limiting toxicities

Aphasia/dysphasia or confusion/cognitive disturbance which resolves to at least grade 1 or baseline within 2 weeks and to at least baseline within 4 weeks
Fever grade 3 or 4
Immediate hypersensitivity reactions occurring within 2 hours of KTE-X19 infusion (related tKTE-X19 infusion) that are reversible to a grade 2 or less within 24 hours of KTE-X19 infusion with standard therapy
Renal toxicity which requires dialysis for ≤7 days
Intubation for airway protection if ≤7 days
TLS including associated manifestations attributable to TLS (eg, electrolyte abnormalities, renal function, hyperuricemia)
Grade 3 transaminase, alkaline phosphatase, bilirubin or other liver function test elevation, provided there is resolution to ≤ grade 2 within 14 days
Grade 4 transient serum hepatic enzyme abnormalities provided there is resolution to ≤ grade 3 within 72 hours
Hypogammaglobulinemia grade 3 or 4
Grade 3 nausea and/or anorexia
Adverse events attributed tCRS will be mapped tthe overall CRS grading assessment for the determination of DLT
All occurrences of grade 3 CRS of duration >7 days and all occurrences of grade 4 CRS are considered DLTs, other than occurrences of CRS due to the exceptions listed above CRS, cytokine release syndrome; DLT, dose-limiting toxicity; TLS, tumor lysis syndrome.

DLTs were evaluated in the first 3 patients treated at the starting dose of $2 \times 10^6$ CAR T cells/kg. One additional patient was enrolled to receive $2 \times 10^6$ CAR T cells/kg. A Safety Review Team evaluated safety data after these patients were followed for 28 days post-infusion, and subsequent patients received $1 \times 10^6$ CAR T cells/kg to evaluate the potential to mitigate the risk of CRS and NE for improvement in the risk:benefit ratio. (Shah B D et al., J Clin Oncol 37:abstr 7006, 2019; Shah B D et al., Blood In Press, 2021.) To further optimize the risk:benefit ratio, the dosing formulation was modified from 68 mL to 40 mL for patients in a second cohort at the $1 \times 10^6$ CART cells/kg. Given the expected patient weight in this pediatric study population, the 40 mL formulation was intended to provide a higher cell density than the 68 mL formulation in order to mitigate the potential risk of a lower final product volume. Patients underwent leukapheresis to obtain cells for CAR T-cell manufacturing, followed by subsequent conditioning chemotherapy; fresh leukapheresis material was used for CAR T-cell manufacturing. Specified bridging chemotherapy was permitted between leukapheresis and conditioning chemotherapy (Table 10).

TABLE 10

Bridging chemotherapy
Predefined Bridging Chemotherapy Regimens*

| | |
|---|---|
| Vincristine† | 1.5 mg/m² (maximum dose 2 mg) IV weekly × 4 doses with dexamethasone 6 mg/m² daily × 5 days |
| Attenuated VAD | Vincristine 1.5 mg/m² (maximum dose 2 mg) IV weekly × 4 doses with dexamethasone 6 mg/m² daily × 5 days, and doxorubicin 50 mg/m² IV × 1 dose (first week only) |
| Mercaptopurine (6-MP) | 50 mg/m²/dose PO once daily (administer at bedtime on an empty stomach to improve absorption) |
| Attenuated FLAG‡ | Fludarabine 25 mg/m² IV daily followed by cytarabine 2 g/m² IV daily for a total of 2 to 5 days per investigator discretion; G-CSF 5 µg/kg SC or IV starts on the day after completion of chemotherapy and continuing until ANC recovery to >1000/µL × 2 consecutive days, or until the day before the start of conditioning chemotherapy, whichever comes first |
| Hydroxyurea | Doses titrated between 15 and 50 mg/kg/day (rounded to the nearest 500- mg capsule and given as a single daily oral dose on a continuous basis) |
| Cyclophosphamide and etoposide | Cyclophosphamide 440 mg/m² IV daily on Days 1-5 and etoposide 100 mg/m² daily on Days 1-5 |

*Use of a TKI in combination with any of the above regimens is allowed for patients with Ph+ ALL and Ph-like ALL;
†For patients who cannot tolerate vincristine, another alkaloid may be used.
‡Concurrent treatment with intrathecal methotrexate should be avoided during the administration of FLAG chemotherapy. ALL, acute lymphoblastic leukemia; ANC, absolute neutrophile count; FLAG, fludarabine, high-dose cytarabine, and G-CSF; G-CSF, granulocyte colony-stimulating factor; IV, intravenous; Ph, Philadelphia chromosome; PO, oral; SC, subcutaneous; TKI, tyrosine kinase inhibitor; VAD, vincristine, doxorubicin, and dexamethasone.

KTE-X19 was administered on day 0 at the respective target dose of $2 \times 10^6$ or $1 \times 10^6$ CAR T cells/kg (68 mL or 40 mL formulation). Hospitalization post-infusion was required for a minimum of 7 days, followed by response assessments at prespecified timepoints. All patients completing the month 3 visit were followed in the long-term follow-up period for survival and disease status every 3 months through month 18, every 6 months from months 24 to 60, then once annually for up to 15 years. Patients could be removed from the study if they withdrew consent for further follow-up, were lost to follow-up, or died. Allogeneic stem cell transplant (alloSCT) was not required per the protocol but was allowed per investigator discretion.

Patients receiving 1×10⁶ CAR T cells/kg (40 mL) were treated under revised toxicity management guidelines: tocilizumab was only administered for neurologic events (NEs) if in the context of cytokine release syndrome (CRS), and steroids were initiated for grade 2 NEs, whereas they were initiated for grade 3 NEs in the original toxicity management guidelines for the 1×10⁶ CAR T cells/kg (68 mL) cohort (Table 11).

TABLE 11

Original and revised neurotoxicity management guidelines.

| NE Grade | Original Management Guidelines | Revised Management Guidelines |
|---|---|---|
| Grade 1 | Supportive Care and Evaluation<br>Supportive care<br>Neurological examination and additional work-up as clinically indicated<br>Tocilizumab<br>N/A<br>Corticosteroids<br>N/A | Supportive Care and Evaluation<br>Supportive care<br>Closely monitor neurologic status<br>Consider prophylactic levetiracetam*<br>Tocilizumab<br>N/A<br>Corticosteroids<br>Dexamethasone 10 mg IV × 1<br>If not improving after 2 days, repeat dexamethasone |
| Grade 2 | Supportive Care and Evaluation<br>Neurological examination, brain MRI, and evaluation of CSF; consider EEG as clinically indicated<br>Consider prophylactic antiepileptic<br><br>Tocilizumab<br>Consider tocilizumab 8 mg/kg IV over 1 hour (not to exceed 800 mg) for patients with comorbid conditions (eg, grade ≥2 CRS)<br><br><br><br><br><br>Corticosteroids<br>N/A | Supportive Care and Evaluation<br>Continuous cardiac telemetry and pulse oximetry as indicated<br>Closely monitor neurologic status with serial neuro exams to include fundoscopy and Glasgow Coma Score. Consider neurology consult<br>Perform brain imaging (eg, MRI), EEG, and lumbar puncture (with opening pressure) if no contraindications<br>Tocilizumab<br>For patients with concurrent CRS, administer tocilizumab 8 mg/kg IV over 1 hour (not to exceed 800 mg); repeat every 8 hours as needed if not responsive to IV fluids or increasing supplemental oxygen, for a maximum of 3 doses in 24 hours; maximum total of 4 doses if no clinical improvement in the signs and symptoms of CRS<br>Corticosteroids<br>Dexamethasone 10 mg IV 4 times a day<br>If improving, continue corticosteroids until the event is grade 1 or less, then quickly taper as clinically appropriate<br>If not improving, manage as appropriate grade below; consider contacting Medical Monitor |
| Grade 3 | Supportive Care and Evaluation<br>Per grade 2<br>Monitor with continuous cardiac telemetry and pulse oximetry<br>Tocilizumab<br>Consider tocilizumab 8 mg/kg IV over 1 hour (not to exceed 800 mg); repeat every 4-6 hours if symptoms have not stabilized or improved<br>Corticosteroids<br>Consider corticosteroids (eg, dexamethasone 10 mg IV every 6 hours or methylprednisolone 1 mg/kg BID) for worsening symptoms despite tocilizumab | Supportive Care and Evaluation<br>Manage in monitored care or ICU<br><br><br>Tocilizumab<br>Per grade 2<br><br><br><br><br>Corticosteroids<br>Methylprednisolone 1000 mg IV once daily<br><br>If improving, continue corticosteroids until the event is grade 1 or less, then quickly taper as clinically appropriate<br>If not improving, manage as appropriate grade below; consider contacting Medical Monitor |

TABLE 11-continued

Original and revised neurotoxicity management guidelines.

| NE Grade | Original Management Guidelines | Revised Management Guidelines |
|---|---|---|
| Grade 4 | Supportive Care and Evaluation Per grade 2 Monitor with continuous cardiac telemetry and pulse oximetry Tocilizumab Administer tocilizumab per grade 3 if not previously administered Corticosteroids Administer corticosteroids (eg, methylprednisolone 1 g/d × 3 days, followed by 250 mg BID × 2 days, then 125 mg BID × 2 days, then 60 mg BID × 2 days) | Supportive Care and Evaluation Per grade 3 Mechanical ventilation may be required Tocilizumab Per grade 2 Corticosteroids Methylprednisolone 1000 mg IV twice a day Continue corticosteroids until the event is grade 1 or less, then quickly taper as clinically appropriate If not improving, consider 1 g of methylprednisolone 3 times a day or alternative therapy†; contact Medical Monitor |

*Prophylactic levetiracetam applies to all grades.
†Initiation of alternative therapy should be discussed with the Medical Monitor and includes (but is not limited to) anakinra, siltuximab, ruxolitinib, cyclophosphamide, intravenous immunoglobulin, and antithymocyte globulin. BID, twice daily; CRS, cytokine release syndrome; CSF, cerebrospinal fluid; EEG, electroencephalogram; ICU, intensive care unit; IV, intravenous; MRI, magnetic resonance imaging Outcomes and Assessments The phase 1 primary endpoint was the incidence of DLTs in the DLT-evaluable set, which included the first 3 patients treated with KTE-X19 at the $2\times10^6$ CAR T cells/kg dose. Secondary endpoints included safety, overall CR rate (CR+ CRi), duration of remission (DOR), MRD-negativity rate, alloSCT rate, OS, and relapse-free survival (RFS). Adverse events, including individual symptoms of cytokine release syndrome (CRS) and neurologic events (NEs), were graded according to the NCI Common Terminology Criteria for adverse events (AEs) version 4.03. CRS was graded according to modified criteria of Lee at al., Blood. 2014; 124(2): 188-195. Overall response was determined by investigator after bone marrow and peripheral blood assessments, as detailed in the table below. (Cheson B D et al., J Clin Oncol. 2007; 25(5):579-586.) Bone marrow evaluations and response assessments were conducted at day 28 and months 2 and 3. In patients who received bridging chemotherapy, an additional bone marrow aspirate was required between the end of bridging chemotherapy and day −4 (+/−2 days). For patients with extramedullary disease, response was assessed per the response criteria for extramedullary and CNS disease in the revised International Working Group criteria for malignant lymphoma as detailed in the table below. (Cheson B D et al., J Clin Oncol. 2007; 25(5):579-586.) Minimal residual disease (MRD) was tested by flow cytometry (Neogenomics) with a sensitivity of 0.01% using the following markers: CD3, CD9, CD10, CD13/CD33, CD19, CD20, CD34, CD38, CD45, CD58, and CD71. (Gupta S et al., Leukemia. 2018; 32(6):1370-1379; Borowitz M J et al., Blood. 2015; 126(8):964-971; Bruggemann M et al., Hematology Am Soc Hematol Educ Program. 2017; 2017(1):13-21.) MRD-negative is defined as MRD<$10^4$ per the standard assessment. A portion of the bone marrow aspirate taken at day 28 and months 2 and 3 was analyzed for MRD. Translational analyses were performed on product, blood, and tumor samples to evaluate the pharmacokinetic and pharmacodynamic profile of KTE-X19 in pediatric R/R B-ALL as exploratory endpoints. Pharmacokinetic and pharmacodynamic assessments and associations with clinical outcomes were previously described. (Locke F L et al., Mol Ther. 2017; 25(1):285-295.) The overall disease response was as described in Table 12.

TABLE 12

Overall disease response classification.

| Response | BM | Peripheral Blood* | | CNS EMD | | Non-CNS EMD§ |
|---|---|---|---|---|---|---|
| CR | ≤5%† and | ANC ≥1000 and Plt ≥100,000 | and | CNS-1# | and | CR |
| CRi | | ANC ≥1000 and Plt <100,000 OR ANC <1000 and Plt ≥100,000 | | | | |
| CRh | | ANC ≥500 and Plt ≥50,000 but not CR | | | | |
| Blast-free hypoplastic or aplastic BM | | Any values not meeting criteria for CR, CRi, or CRh | | | | |
| PR | | All criteria for CR, CRi, CRh, or blast-free hypoplastic or aplastic bone marrow are met | | | and | PR |

TABLE 12-continued

Overall disease response classification.

| Response | BM | Peripheral Blood* | | CNS EMD | | Non-CNS EMD§ |
|---|---|---|---|---|---|---|
| Relapse | >5%‡ | or | Circulating leukemia present** | or | CNS-2 or CNS-3 | or | PD |
| No response | | All required assessments are performed with failure to attain the criteria needed for any response category | | | | |
| Unknown | | Assessment is not done, incomplete, or indeterminate | | | | |
| | | Note: Overall disease response can be assessed as "relapsed disease" if any single element of disease response assessment exhibits relapse, other unknown elements of disease response assessment do not need to be evaluated | | | | |

*The units for Plt and ANC are per μL. ANC and Plt values should be evaluated every time a BM evaluation is performed. If not done, ANC and Plt values used for response assessment can be from any time 7 days prior to the BM result to any time after the BM result.
§In patients evaluated for non-CNS EMD, imaging and bone marrow results used for assessment of overall disease response must be within 30 days of each other.
‡Blasts by morphology in BM.
At day 28 or at the time of first presumed response, whichever is earlier, for patients who achieve a CR.
**No circulating leukemia is <1% circulating blasts by morphology. Circulating leukemia is ≥1% circulating blasts by morphology. If ≥1% blast by morphology and there is no other evidence of leukemia, then flow or molecular studies should be conducted to confirm that blasts are leukemia. ANC, absolute neutrophil count; BM, bone marrow; CNS, central nervous system; CR, complete remission; CRh, complete remission response with partial hematologic recovery; CRi, complete remission response with incomplete hematologic recovery; EMD, extramedullary disease; PD, progressive disease; Plt, platelets; PR, partial response.

Results

Patients

Between 17 Feb. 2016 and 1 Aug. 2018, 31 patients were enrolled and underwent leukapheresis. The median time from leukapheresis to KTE-X19 product release was 14.0 days (range, 9.0-20.0) for all treated patients, 16.5 days (range, 12.0-23.0) from leukapheresis to delivery to study site, and 27.0 days (range, 18.0-41.0) from leukapheresis to infusion. The data cutoff was Sep. 9, 2020. Of the 31 enrolled patients, 24 (77%) received conditioning chemotherapy and were subsequently dosed. Seven patients were not dosed due to the following reasons: adverse event (AE; n=1), product unavailable (n=3), ineligible due to AE (n=1), product unavailable and ineligible (n=1), and death (n=1). Twenty-four patients received conditioning chemotherapy followed by KTE-X19; 4 patients received the $2\times10^6$ CAR T cells/kg dose, 11 patients received the $1\times10^6$ CAR T cells/kg (68 mL) dose formulation, and 9 received the $1\times10^6$ CART cells/kg (40 mL) dose formulation. The median follow-up for all treated patients was 36.1 months (range, 24.0-53.9). The median age of treated patients was 13.5 years (range, 3-20); 42% of patients had received ≥3 prior lines of therapy; 29% had primary refractory disease; 25% were R/R after alloSCT; and median bone marrow blasts at screening were 44% (range, 6-99; Table 13). Prior to enrollment, 6 (25%) patients had undergone prior alloSCT, 8 (33%) received prior blinatumomab, including 3 (13%) of whom received blinatumomab as the last prior therapy, and 1 (4%) had extramedullary disease. Of the 31 enrolled patients, 30 (97%) received bridging therapy per protocol with new baseline disease assessments performed just prior to lymphodepleting chemotherapy. Safety analysis and efficacy analysis are presented for all 24 patients that were dosed.

TABLE 13

Patient Characteristics

| Characteristic | $2 \times 10^6$ cells/kg (n = 4) | $1 \times 10^6$ cells/kg, 68 mL (n = 11) | $1 \times 10^6$ cells/kg, 40 mL (n = 9) | Overall (N = 24) |
|---|---|---|---|---|
| Median age, years (range) | 11.5 (8-18) | 12 (4-17) | 14 (3-20) | 13.5 (3-20) |
| Sex, n (%) | | | | |
| Male | 2 (50) | 8 (73) | 5 (56) | 15 (63) |
| Female | 2 (50) | 3 (27) | 4 (44) | 9 (38) |
| Lansky score, n (%) | | | | |
| 80 | 0 | 1 (9) | 0 | 1 (4) |
| 90 | 1 (25) | 6 (55) | 4 (44) | 11 (46) |
| 100 | 2 (50) | 2 (18) | 2 (22) | 6 (25) |
| Karnofsky score, n (%) | | | | |
| 80 | 0 | 2 (18) | 1 (11) | 3 (13) |
| 90 | 0 | 0 | 2 (22) | 2 (8) |
| 100 | 1 (25) | 0 | 0 | 1 (4) |
| Number of prior lines of therapy, n (%) | | | | |
| ≤2 | 2 (50) | 5 (45) | 7 (78) | 14 (58) |
| ≥3 | 2 (50) | 6 (55) | 2 (22) | 10 (42) |
| Prior blinatumomab, n (%) | 0 | 5 (45) | 3 (33) | 8 (33) |

TABLE 13-continued

| | Patient Characteristics | | | |
|---|---|---|---|---|
| Characteristic | $2 \times 10^6$ cells/kg (n = 4) | $1 \times 10^6$ cells/kg, 68 mL (n = 11) | $1 \times 10^6$ cells/kg, 40 mL (n = 9) | Overall (N = 24) |
| Prior inotuzumab ozogamicin, n (%) | 0 | 1 (9) | 0 | 1 (4) |
| Prior stem cell transplant, n (%) | 1 (25) | 4 (36) | 1 (11) | 6 (25) |
| Refractory subgroup pre-enrollment, n(%) | | | | |
| Relapsed or refractory to ≥2nd-line therapy | 2 (50) | 3 (27) | 6 (67) | 11 (46) |
| Relapsed or refractory post-alloSCT | 1 (25) | 4 (36) | 1 (11) | 6 (25) |
| Primary refractory | 1 (25) | 4 (36) | 2 (22) | 7 (29) |
| Median BM blasts at screening, % (range) | 57 (41-99) | 28 (7-98) | 58 (6-97) | 44 (6-99) |
| Median preconditioning BM blasts, % (range) | 85 (49-100) | 6 (0-89) | 44 (1-82) | 37 (0-100) |

Safety

Among the 3 DLT-evaluable patients receiving $2 \times 10^6$ CAR T cells/kg, no DLTs were observed. All treated patients (n=24) experienced at least one grade≥3 AEs, most commonly hypotension (50%), and anemia (42%; Table 14). Serious AEs of any grade occurred in 71% of patients. Grade≥3 infections occurred in 42% of patients.

In all treated patients (n=24), CRS was reported in 21 patients (88%), with 8 patients (33%) experiencing grade≥3 CRS (Table 15) according to modified Lee grading criteria. Lee D W et al., Blood 124:188-95, 2014. No grade 4 or grade 5 CRS events occurred. The most common grade≥3 CRS symptoms were hypotension (50%) and pyrexia (25%). Any-grade and grade≥3 hypoxia was observed in 13% and

TABLE 14

Adverse Events

| | $2 \times 10^6$ cells/kg (n = 4) | | $1 \times 10^6$ cells/kg, 68 mL (n = 11) | | $1 \times 10^6$ cells/kg, 40 mL (n = 9) | | All patients (N = 24) | |
|---|---|---|---|---|---|---|---|---|
| n (%)* | Any grade | Grade ≥3 | Any grade | Grade ≥3 | Any grade | Grade ≥3 | Any grade | Grade ≥3 |
| Any adverse event | 4 (100) | 4 (100) | 11 (100) | 11 (100) | 9 (100) | 9 (100) | 24 (100) | 24 (100) |
| Pyrexia | 4 (100) | 3 (75) | 11 (100) | 3 (27) | 8 (89) | 2 (22) | 23 (96) | 8 (33) |
| Hypotension | 4 (100) | 4 (100) | 8 (73) | 6 (55) | 6 (67) | 2 (22) | 18 (75) | 12 (50) |
| Headache | 2 (50) | 0 | 8 (73) | 2 (18) | 7 (78) | 0 | 17 (71) | 2 (8) |
| Anemia | 1 (25) | 1 (25) | 3 (27) | 3 (27) | 7 (78) | 6 (67) | 11 (46) | 10 (42) |
| Nausea | 2 (50) | 2 (50) | 5 (45) | 1 (9) | 4 (44) | 0 | 11 (46) | 3 (13) |
| Hypokalemia | 3 (75) | 2 (50) | 3 (27) | 1 (9) | 4 (44) | 3 (33) | 10 (42) | 6 (25) |
| Vomiting | 0 | 0 | 4 (36) | 0 | 6 (67) | 0 | 10 (42) | 0 |
| Neutrophil count decreased | 0 | 0 | 3 (27) | 3 (27) | 6 (67) | 6 (67) | 9 (38) | 9 (38) |
| Tachycardia | 0 | 0 | 4 (36) | 1 (9) | 5 (56) | 0 | 9 (38) | 1 (4) |
| Hypertension | 3 (75) | 2 (50) | 4 (36) | 0 | 1 (11) | 0 | 8 (33) | 2 (8) |
| Febrile neutropenia | 1 (25) | 1 (25) | 3 (27) | 3 (27) | 3 (33) | 3 (33) | 7 (29) | 7 (29) |
| Abdominal pain | 1 (25) | 0 | 3 (27) | 0 | 2 (22) | 0 | 6 (25) | 0 |
| Confusional state | 0 | 0 | 4 (36) | 0 | 2 (22) | 0 | 6 (25) | 0 |
| Constipation | 0 | 0 | 4 (36) | 0 | 2 (22) | 0 | 6 (25) | 0 |
| Decreased appetite | 1 (25) | 1 (25) | 2 (18) | 0 | 3 (33) | 2 (22) | 6 (25) | 3 (13) |
| Fatigue | 0 | 0 | 3 (27) | 0 | 3 (33) | 0 | 6 (25) | 0 |
| Hypogammaglobulinemia | 0 | 0 | 2 (18) | 0 | 4 (44) | 0 | 6 (25) | 0 |
| Hypomagnesemia | 2 (50) | 0 | 1 (9) | 0 | 3 (33) | 0 | 6 (25) | 0 |
| Platelet count decreased | 2 (50) | 2 (50) | 2 (18) | 2 (18) | 2 (22) | 2 (22) | 6 (25) | 6 (25) |
| White blood cell count decreased | 1 (25) | 1 (25) | 2 (18) | 2 (18) | 3 (33) | 2 (22) | 6 (25) | 5 (21) |
| Cough | 0 | 0 | 3 (27) | 0 | 2 (22) | 0 | 5 (21) | 0 (0) |
| Hypophosphatemia | 1 (25) | 0 | 2 (18) | 1 (9) | 2 (22) | 1 (11) | 5 (21) | 2 (8) |
| Hypoxia | 1 (25) | 1 (25) | 3 (27) | 1 (9) | 1 (11) | 1 (11) | 5 (21) | 3 (13) |
| Pain | 2 (50) | 0 | 1 (9) | 0 | 2 (22) | 0 | 5 (21) | 0 (0) |

*Table includes adverse events of any grade occurring in ≥20% of all patients.

8% of patients, respectively. The median time to onset of CRS and duration after KTE-X19 infusion was 5 days (range, 1-14) and 7 days, respectively, with all events resolved.

of patients who received $2\times10^6$ CAR T cells/kg and 27% of patients who received $1\times10^6$ CAR T cells/kg (68 mL) but were lowest (11%) in patients who received $1\times10^6$ CAR T cells/kg (40 mL). In addition, the median time to onset of

TABLE 15

Cytokine release syndrome and neurologic events

| n(%) | $2 \times 10^6$ cells/kg (n = 4) | | $1 \times 10^6$ cells/kg, 68 mL (n = 11) | | $1 \times 10^6$ cells/kg, 40 mL (n = 9) | | All patients (N = 24) | |
|---|---|---|---|---|---|---|---|---|
| Steroids | 1 | (25) | 4 | (36) | 5 | (56) | 10 | (42) |
| Tocilizumab | 3 | (75) | 6 | (55) | 6 | (67) | 15 | (63) |
| Vasopressors for treatment of CRS | 3 | (75) | 4 | (36) | 2 | (22) | 9 | (38) |

| Adverse event, n (%)* | Any grade | Grade ≥3 | Any grade | Grade ≥3 | Any grade | Grade ≥3 | Any grade | Grade ≥3 |
|---|---|---|---|---|---|---|---|---|
| CRS[†,‡] | 4 (100) | 3 (75) | 9 (82) | 3 (27) | 8 (89) | 2 (22) | 21 (88) | 8 (33) |
| Pyrexia | 3 (75) | 3 (75) | 9 (82) | 2 (18) | 5 (56) | 1 (11) | 17 (71) | 6 (25) |
| Hypotension | 4 (100) | 4 (100) | 8 (73) | 6 (55) | 4 (44) | 2 (22) | 16 (67) | 12 (50) |
| Headache | 1 (25) | 0 | 3 (27) | 0 | 3 (33) | 0 | 7 (29) | 0 |
| Tachycardia | 0 | 0 | 2 (18) | 1 (9) | 4 (44) | 0 | 6 (25) | 1 (4) |
| Chills | 0 | 0 | 0 | 0 | 3 (33) | 0 | 3 (13) | 0 |
| Febrile neutropenia | 0 | 0 | 0 | 0 | 3 (33) | 3 (33) | 3 (13) | 3 (13) |
| Hypoxia | 1 (25) | 1 (25) | 1 (9) | 0 | 1 (11) | 1 (11) | 3 (13) | 2 (8) |
| Sinus tachycardia | 0 | 0 | 3 (27) | 0 | 0 | 0 | 3 (13) | 0 |
| Neurologic event[†,‡] | 1 (25) | 1 (25) | 9 (82) | 3 (27) | 6 (67) | 1 (11) | 16 (67) | 5 (21) |
| Confusional state | 0 | 0 | 4 (36) | 0 | 2 (22) | 0 | 6 (25) | 0 (0) |
| Encephalopathy | 1 (25) | 1 (25) | 1 (9) | 1 (9) | 2 (22) | 1 (11) | 4 (17) | 3 (13) |
| Aphasia | 1 (25) | 1 (25) | 1 (9) | 0 | 1 (11) | 0 | 3 (13) | 1 (4) |
| Lethargy | 0 | 0 | 2 (18) | 1 (9) | 1 (11) | 0 | 3 (13) | 1 (4) |
| Tremor | 0 | 0 | 2 (18) | 0 | 1 (11) | 0 | 3 (13) | 0 (0) |
| Days (range) CRS | | | | | | | | |
| Median time to onset | 2 (1-4) | | 6 (3-14) | | 7 (1-9) | | 5 (1-14) | |
| Median duration | 10.5 | | 7 | | 8 | | 7 | |
| Neurologic events | | | | | | | | |
| Median time to onset | 7 (7-7) | | 9 (4-14) | | 10 (3-60) | | 9.5 (3-60) | |
| Median duration | NA[‖] | | 8 | | 11 | | 8 | |

*Includes CRS symptoms and neurologic events occurring in ≥10% of all patients.
[†]Cytokine release syndrome was categorized according to a modified grading system proposed by Lee et al. Blood, 2014.

Among all treated patients, any-grade NEs were reported in 16 patients (67%), and grade≥3 events occurred in 5 patients (21%), with encephalopathy (13%) being the most common grade≥3 event (Table 15). One grade 4 fully reversible NE occurred (brain edema) in a patient who received $1\times106$ CAR T cells/kg (68 mL) dose; for this event, the patient was treated with dexamethasone, mannitol, sodium chloride, and tocilizumab. There were no grade 5 NEs. Overall, the median time to onset of NEs was 9.5 days (range, 3-60) after infusion, and the median duration of NEs was 8 days. NEs resolved in 14 of 16 patients (88%). The NEs of the remaining two patients were ongoing at the time of death due to an AE (n=1) or progressive disease (n=1).

Among all treated patients, 42% received steroids, 63% received tocilizumab, and 46% received vasopressors (Table 15). Improved overall safety was observed in the 9 patients treated with the $1\times10^6$ CAR T cells/kg (40 mL) dose under revised toxicity management, relative to the 4 patients treated with $2\times10^6$ CAR T cells/kg and the 11 patients treated at $1\times10^6$ CAR T cells/kg (68 mL) under the original guidelines. Of the patients receiving $2\times10^6$ CAR T cells/kg, 75% experienced grade≥3 CRS, compared with 27% and 22% of patients receiving $1\times10^6$ CAR T cells/kg (68 mL and 40 mL, respectively). Grade≥3 NEs were observed in 25% NEs, as well as CRS, appeared to be delayed in the $1\times10^6$ CAR T cells/kg dose cohorts compared with the $2\times10^6$ CAR T cells/kg dose cohort.

Among the 8 patients (33%) who died on study, 6 died from progressive disease (median 190.5 days post-KTE-X19 infusion), and 2 patients died from AEs (other than grade 5 B-ALL) considered unrelated to KTE-X19, including disseminated mucormycosis (n=1, day 15 post-KTE-X19 infusion) and *Escherichia* sepsis (n=1, day 409 post-KTE-X19 infusion). Of those who died, 3 patients received $2\times10^6$ CAR T cells/kg, 4 received $1\times10^6$ CAR T cells/kg (68 mL), and 1 received $1\times10^6$ CAR T cells/kg (40 mL). No patient tested positive for replication-competent retrovirus or antibodies to anti-CD19 CAR at any time.

Efficacy

With a median follow-up time of 36.1 months (range, 24.0-53.9), all treated patients (n=24) were evaluable for efficacy. The overall remission rate by investigator assessment was 67%, with 29% of patients (n=7) achieving CR and 38% achieving CRi (n=9; Table 16). In the $2\times10^6$, $1\times10^6$ (68 mL), and $1\times10^6$ (40 mL) CAR T cells/kg dose groups, the CR+CRi rate was 75%, 64%, and 67%, respectively. The median time from infusion to CR+CRi across dose levels was 30 days (range, 26-113 days). The overall MRD-negativity rate was 100% among the 16 patients with CR+CRi. Sixteen patients overall (67%) received alloSCT as subsequent consolidative therapy, including 2, 8, and 6 patients in the $2\times10^6$, $1\times10^6$ (68 mL), and $1\times10^6$ (40 mL) CAR T cells/kg dose groups, respectively. Fourteen of the 16 patients (88%) who achieved CR+CRi (2, 7, and 5 in the in the $2\times10^6$, $1\times10^6$ [68 mL], and $1\times10^6$ [40 mL] CAR T cells/kg dose groups, respectively) underwent subsequent alloSCT. Two of these patients relapsed prior to subsequent alloSCT; both received consolidating chemotherapy prior before proceeding to alloSCT. Of the 2 patients who achieved CR+CRi but did not receive subsequent alloSCT, 1 died due to progressive disease, and 1 was lost to follow-up. The 2 patients who did not achieve any response proceeded to subsequent alloSCT and achieved CR as their response to alloSCT. The median time to transplant for all treated patients was 2.3 months (range, 1.4-24.9) post-KTE-X19.

TABLE 16

Remission rates and minimal residual disease status

| Response Category, n (%) | $2 \times 10^6$ cells/kg (n = 4) | $1 \times 10^6$ cells/kg, 68 mL (n = 11) | $1 \times 10^6$ cells/kg, 40 mL (n = 9) | Overall (N = 24) |
|---|---|---|---|---|
| Overall complete remission rate | 3 (75) | 7 (64) | 6 (67) | 16 (67) |
| Complete remission | 0 | 3 (27) | 4 (44) | 7 (29) |
| Complete remission with incomplete hematologic recovery | 3 (75) | 4 (36) | 2 (22) | 9 (38) |
| Complete remission with partial hematologic recovery | 0 | 1 (9) | 0 | 1 (4) |
| Blast-free hypoplastic/aplastic bone marrow | 0 | 0 | 1 (11) | 1 (4) |
| No response | 0 | 1 (9) | 1 (11) | 2 (8) |
| Unknown or not evaluable | 1 (25) | 2 (18) | 1 (11) | 4 (17) |
| Overall MRD-negativity rate* | 3 (75) | 8 (73) | 7 (78) | 18 (75) |

*MRD negativity was assessed by flow cytometry with a sensitivity of 0.01% at day 28 and months 2 and 3. MRD results after allogeneic stem cell transplant or new anticancer therapies are excluded. MRD, minimal residual disease.

The median DOR for the 16 patients who achieved CR+CRi post-KTE-X19 was 7.2 months (95% CI, 4.1-14.2) after censoring for subsequent alloSCT, and was 4.1 months, 10.7 months, and not reached in the $2\times10^6$, $1\times10^6$ (68 mL), and $1\times10^6$ (40 mL) CAR T cells/kg dose groups, respectively. The median DOR was 14.2 months (95% CI, 3.9—NE) without censoring for subsequent alloSCT and resumption of tyrosine kinase inhibitor. The median DOR among the 14 patients with CR+CRi who received subsequent alloSCT post-KTE-X19 was 10.7 months (95% CI, 7.2-14.2). The median RFS for all treated patients (n=24) was 5.2 months (95% CI, 0.0-17.8). The median RFS for the $1\times10^6$ CART cells/kg (40 mL) group was not reached and was 5.2 months (95% CI, 0.0-5.2) and 9.1 months (95% CI, 0.0-17.8) in the $2\times10^6$ and $1\times10^6$ (68 mL) cells/kg cohorts, respectively. The median RFS among the 16 patients who proceeded to subsequent alloSCT was 9.1 months (95% CI, 9.1-17.8). The median OS was not reached among all treated patients and in the $1\times10^6$ CAR T cells/kg dose groups and was 8.0 months for the $2\times10^6$ CAR T cells/kg dose group. The 24-month OS rate for the $1\times10^6$ cells/kg (40 mL) dose was 87.5% (95% CI, 38.7-98.1) for the $1\times10^6$ cells/kg (40 mL) dose and 72.7% (95% CI, 37.1-90.3) for the $1\times10^6$ cells/kg (68 mL) dose. Overall, as of the data cutoff, 33% of treated patients (8/24) died, 1 patient discontinued due to full consent withdrawal, and 1 was lost to follow-up. The remaining 58% of patients (14/24) were still alive and in continued follow-up as of data cutoff, all of whom received subsequent alloSCT after KTE-X19. Based on the safety and efficacy data analysis, the RP2D was $1\times10^6$ KTE-X19 cells/kg (40 mL formulation) with revised toxicity management.

Translational Analysis

Figures 10A, 10B, 10C, 10D, 10E:
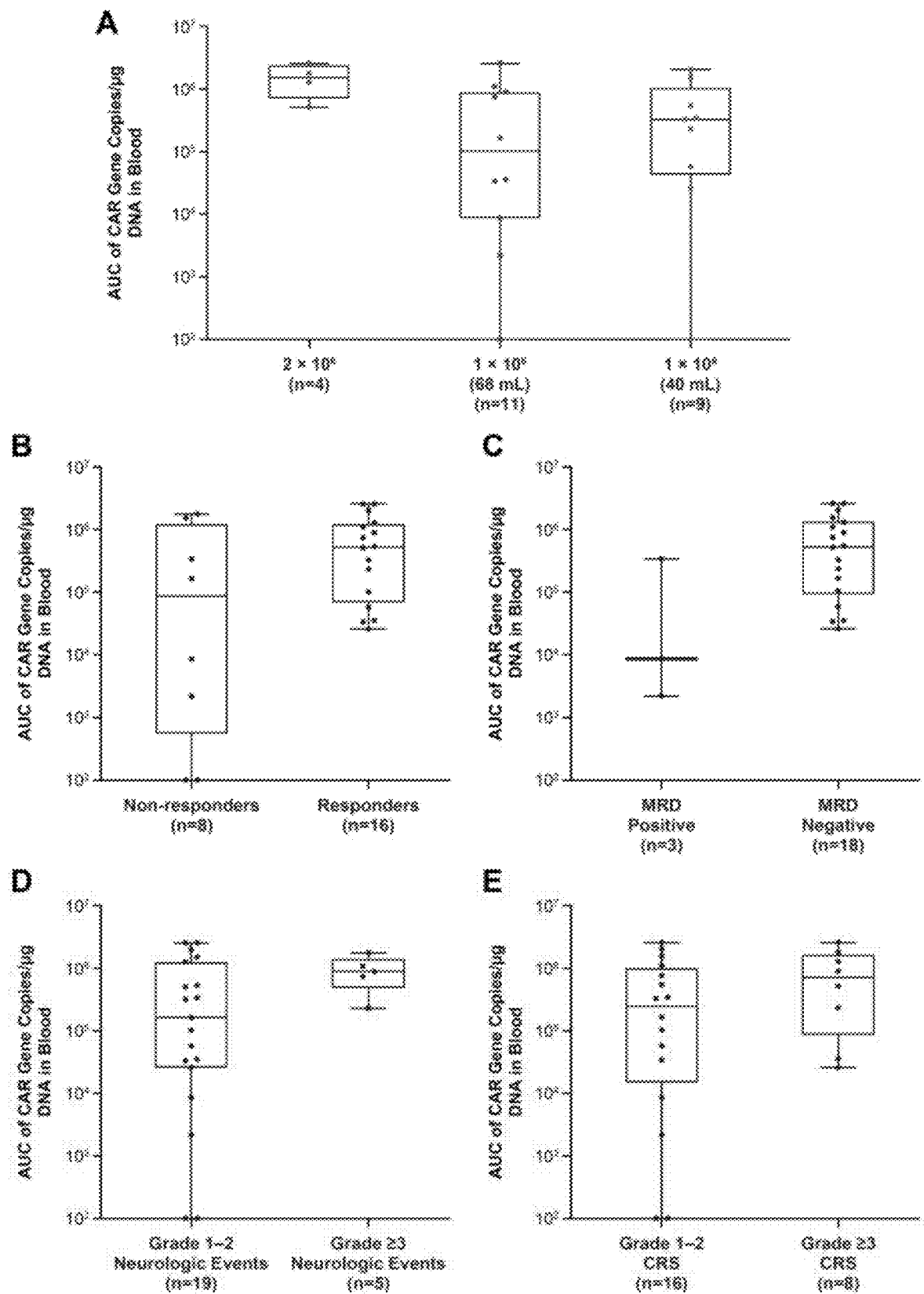
FIGS. 10A, 10B, 10C, 10D, and 10E. Associations between AUC of CAR gene copies/μg DNA (10A), response (10B), MRD rate (10C), and toxicities (10D and 10E).

CAR T-cell expansion in peripheral blood measured by polymerase chain reaction (PCR) and expressed as the number of CAR gene copies/µg DNA in blood was observed across dose groups with peak CAR T-cell levels reached by day 14 followed by a subsequent CAR T-cell contraction to baseline (Table 17). Median CAR T-cell levels were undetectable in blood by PCR across all dose groups at 3 months post-KTE-X19 infusion (Table 17). Median peak CAR gene copies/µg DNA blood were similar between the $1\times10^6$ CAR T cells/kg dose cohorts but were higher in the $2\times10^6$ CAR T cells/kg cohort (FIG. 10A). Patients achieving CR+CRi trended toward higher peak blood CAR gene copies/µg DNA in blood than non-responders, as did patients who were MRD negative versus MRD positive (FIG. 10C). CAR gene copies/µg DNA in blood trended higher in patients who had grade≥3 NEs compared with those who had grade≤2 NEs (FIG. 10D), while there was no apparent difference in peak CAR gene copies/µg DNA in blood for patients with either high- or low-grade CRS in this limited sample size. The median peak CAR gene copies/µg DNA in blood was $5.16\times10^4$ (range, 0-$2.40\times10^5$) in the 16 patients who did not have prior blinatumomab, and was $6.15\times10^3$ (range, 0-$2.49\times10^5$) in the 8 patients who did have prior blinatumomab.

TABLE 17

CAR gene copies in blood over time.

| CAR Gene Copies per µg DNA in Blood | $2 \times 10^6$ | $1 \times 10^6$ 68 mL | $1 \times 10^6$ 40 mL |
|---|---|---|---|
| Baseline | (n = 4) | (n = 11) | (n = 9) |
| Median | 0 | 0 | 0 |
| Range | 0-0 | 0-0 | 0-0 |
| Day 7 | (n = 4) | (n = 11) | (n = 9) |
| Median | 62,600 | 4374 | 10,800 |
| Range | 13,000-232,000 | 0-133,000 | 0-249,000 |
| Week 2 | (n = 4) | (n = 10) | (n = 8) |
| Median | 73,600 | 7249.5 | 25,200 |
| Range | 2414-173,000 | 0-240,000 | 2325-40,100 |
| Week 4 | (n = 3) | (n = 10) | (n = 8) |
| Median | 17,200 | 680 | 453.6 |
| Range | 243-51,800 | 0-4617 | 0-37,800 |
| Week 8 | (n = 1) | (n = 3) | (n = 7) |
| Median | 0 | 607.5 | 0 |

TABLE 17-continued

CAR gene copies in blood over time.

| CAR Gene Copies per μg DNA in Blood | $2 \times 10^6$ | $1 \times 10^6$ 68 mL | $1 \times 10^6$ 40 mL |
|---|---|---|---|
| Range | 0-0 | 105-972 | 0-13,200 |
| Month 3 | (n = 3) | (n = 8) | (n = 5) |
| Median | 0 | 0 | 0 |
| Range | 0-0 | 0-162 | 0-113 |
| Month 6 | (n = 3) | (n = 9) | (n = 3) |
| Median | 0 | 0 | 0 |
| Range | 0-0 | 0-510 | 0-0 |
| Month 9 | (n = 0) | (n = 7) | (n = 4) |
| Median | — | 0 | 0 |
| Range | — | 0-0 | 0-0 |
| Month 12 | (n = 1) | (n = 7) | (n = 0) |
| Median | 0 | 0 | — |
| Range | 0-0 | 0-0 | — |
| Month 15 | (n = 1) | (n = 6) | (n = 3) |
| Median | 0 | 0 | 0 |
| Range | 0-0 | 0-0 | 0-0 |
| Month 18 | (n = 1) | (n = 4) | (n = 0) |
| Median | 0 | 0 | — |
| Range | 0-0 | 0-0 | — |

Figure 11:
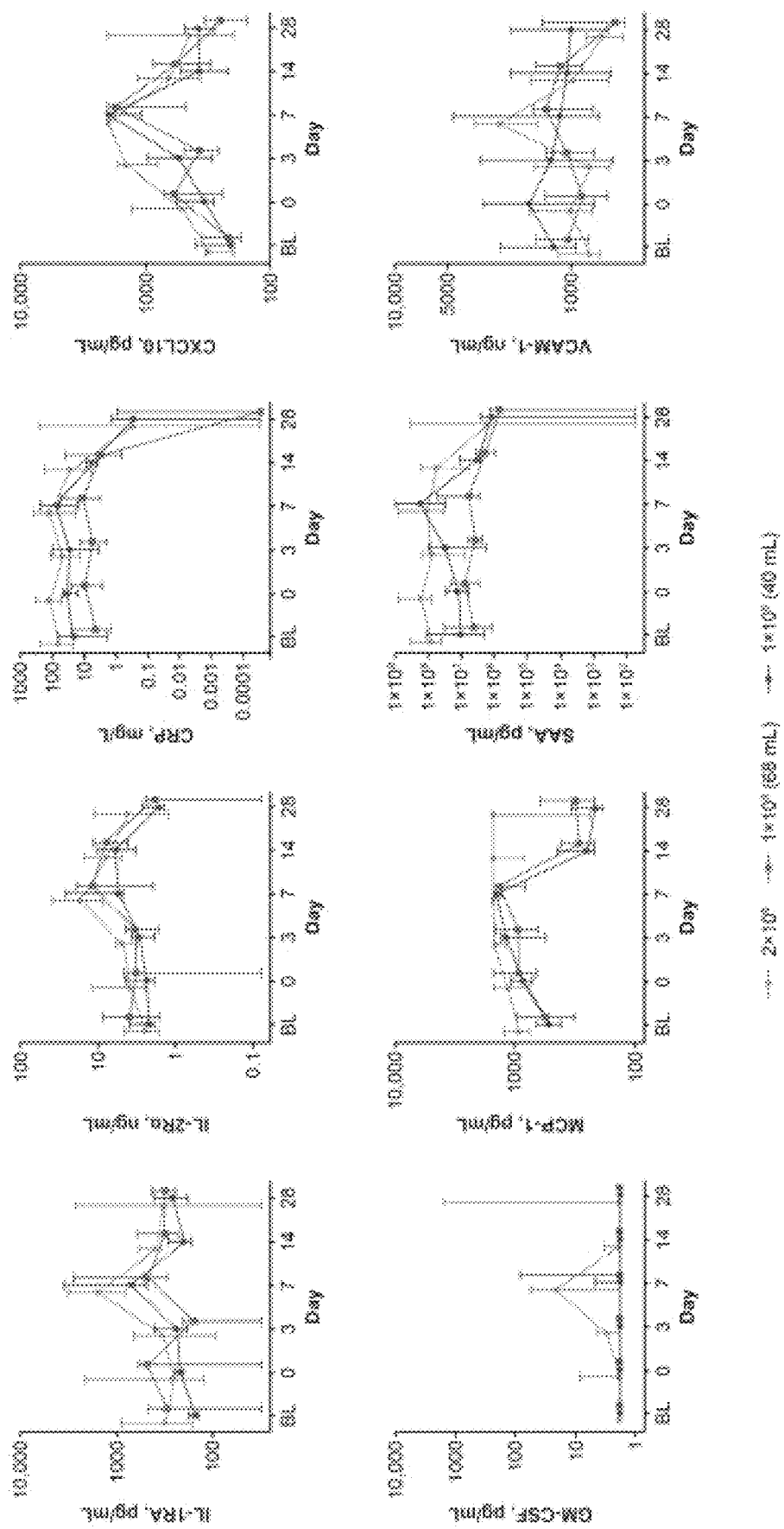
FIG. 11. Additional cytokine and inflammatory marker levels over time. CRP, C-reactive protein; CXCL10, C-X-C motif chemokine ligand 10; GM-CSF, granulocyte-macrophage colony-stimulating factor; IL, interleukin; MCP, monocyte attractant protein; Rα, receptor alpha; RA, receptor antagonist; SAA, serum amyloid A; VCAM, vascular cell adhesion molecule.

Peak levels of multiple key serum cytokines, chemokines, and proinflammatory biomarkers occurred by day 7. Commensurate with peak CAR expansion, some serum analytes trended higher in patients dosed with $2 \times 10^6$ compared with $1 \times 10^6$ CAR T cells/kg (interleukin [IL]-2, IL-5, IL-6, IL-8, IL-10, IL-15, IL-16, ferritin, granzyme B, intercellular adhesion molecule 1 [ICAM-1], interferon gamma [IFN-γ], and tumor necrosis factor alpha [TNF-α] (FIG. 11; Table 18).

TABLE 18

Select serum biomarkers at baseline and at post-infusion peak

| Function | | $2 \times 10^6$ cells/kg (n = 4) | | $1 \times 10^6$ cells/kg, 68 mL (n = 11) | | $1 \times 10^6$ cells/kg, 40 mL (n = 9) | |
|---|---|---|---|---|---|---|---|
| | | Baseline | Peak | Baseline | Peak | Baseline | Peak |
| Homeostatic/pro-liferative | IL-15, pg/mL | | | | | | |
| | Median | 14.9 | 72.0 | 3.3 | 23.2 | 7.3 | 38.2 |
| | Range | 7.5-24.2 | 53.5-116.9 | 1.4*-14.5 | 6.6-91.1 | 1.4*-26.6 | 13.6-65.7 |
| | IL-2, pg/mL | | | | | | |
| | Median | 0.9* | 47.8 | 0.9* | 16.6 | 0.9* | 8.3 |
| | Range | 0.9*-0.9* | 20.8-163.3 | 0.9*-2.1 | 0.9*-690.4 | 0.9*-0.9* | 0.9*-101.1 |
| Pro-inflammatory | IL-6, pg/mL | | | | | | |
| | Median | 9.8 | 976.0† | 1.6* | 90.8 | 1.6* | 23.3 |
| | Range | 1.6*-32.6 | 976.0†-976.0† | 1.6*-13.5 | 1.6*-976.0† | 1.6*-13.9 | 6.7-976.0† |
| | CRP, mg/L | | | | | | |
| | Median | 62.2 | 261.7 | 4.5 | 39.7 | 23.2 | 115.8 |
| | Range | 2.8-379.1 | 149.7-496.0† | 1.2-200.4 | 5.0-300.1 | 0.4-135.5 | 42.3-496.0† |
| | SAA, mg/L | | | | | | |
| | Median | $7.5 \times 10^7$ | $2.7 \times 10^5$ | $3.9 \times 10^6$ | $4.9 \times 10^7$ | $1.0 \times 10^7$ | $5.8 \times 10^8$ |
| | Range | $1.1 \times 10^7$-$6.3 \times 10^8$ | $1.6 \times 10^8$-$1.4 \times 10^{9\dagger}$ | $7.4 \times 10^5$-$1.1 \times 10^8$ | $3.5 \times 10^6$-$1.2 \times 10^9$ | $8.9 \times 10^5$-$9.9 \times 10^8$ | $9.9 \times 10^6$-$1.4 \times 10^{9\dagger}$ |
| | IL-5, pg/mL | | | | | | |
| | Median | 6.3* | 23.6 | 6.3* | 6.3* | 6.3* | 6.3* |
| | Range | 6.3*-6.3* | 23.1-43.8 | 6.3*-56.8 | 6.3*-73.7 | 6.3*-6.3* | 6.3*-6.3* |
| | Ferritin, ng/mL | | | | | | |
| | Median | 3528.4 | $2.5 \times 10^{4\dagger}$ | 2104.0 | 5915.8 | 876.1 | 5745.9 |
| | Range | 2169.1-6570.4 | $1.4 \times 10^4$-$2.5 \times 10^{4\dagger}$ | 595.0-$2.5 \times 10^{4\dagger}$ | 1084.8-$2.5 \times 10^{4\dagger}$ | 83.3-4567.7 | 1116.1-$3.2 \times 10^{4\dagger}$ |
| | IL-1RA, pg/mL | | | | | | |
| | Median | 307.8 | 3366.7 | 292.3 | 2223.8 | 148.7 | 1677.4 |
| | Range | 132.9-1368.5 | 847.3-4000.0† | 31.2-695.4 | 300.1-4000.0† | 77.6-684.0 | 91.9-9000.0† |
| | IL-2Rα, ng/mL | | | | | | |
| | Median | 2.3 | 29.9 | 3.9 | 11.9 | 2.2 | 16.5 |
| | Range | 1.2-6.6 | 11.2-56.3 | 0.1-71.6 | 3.1-60.8 | 1.6-100.0† | 2.4-100.0† |
| | TNF-α, pg/mL | | | | | | |
| | Median | 3.6 | 30.7 | 3.6 | 11.1 | 1.6 | 5.2 |
| | Range | 2.6-8.7 | 14.0-70.2 | 1.6-9.2 | 2.9-34.0 | 0.7*-4.9 | 1.7-31.3 |
| | ICAM-1, ng/mL | | | | | | |
| | Median | 1046.1 | 4868.8 | 622.5 | 1398.2 | 1018.0 | 1875.9 |
| | Range | 674.1-1440.2 | 1626.2-7723.4 | 290.3-1991.8 | 591.9-7204.9 | 264.4-2656.5 | 749.2-5906.3 |
| | VCAM-1, ng/mL | | | | | | |
| | Median | 778.0 | 3417.8 | 1040.7 | 1615.3 | 1254.0 | 2565.3 |
| | Range | 643.6-1553.8 | 823.6-4125.8 | 450.9-2406.4 | 859.1-2778.1 | 514.2-3460.0 | 807.5-5594.2 |

TABLE 18-continued

Select serum biomarkers at baseline and at post-infusion peak

| Function | | 2 × 10⁶ cells/kg (n = 4) | | 1 × 10⁶ cells/kg, 68 mL (n = 11) | | 1 × 10⁶ cells/kg, 40 mL (n = 9) | |
|---|---|---|---|---|---|---|---|
| | | Baseline | Peak | Baseline | Peak | Baseline | Peak |
| Immuno-modulating | GM-CSF, pg/mL | | | | | | |
| | Median | 1.9* | 130.6 | 1.9* | 1.9* | 1.9* | 1.9* |
| | Range | 1.9*-1.9* | 42.1-1500.0† | 1.9*-1.9* | 1.9*-468.9 | 1.9*-1.9* | 1.9*-97.9 |
| | IFN-γ, pg/mL | | | | | | |
| | Median | 7.5* | 1876.0† | 7.5* | 725.7 | 7.5* | 1876.0† |
| | Range | 7.5*-15.2 | 633.5-1876.0† | 7.5*-291.9 | 42.4-1876.0† | 7.5*-61.6 | 7.5*-1876.0† |
| | IL-16, pg/mL | | | | | | |
| | Median | 57.9 | 521.7 | 141.40 | 212.5 | 97.80 | 242.0 |
| | Range | 19.1*-78.1 | 112.7-2502.0 | 69.5-375.8 | 117.9-629.5 | 44.9-112.4 | 104.2-3414.2 |
| Chemokines | IL-10, pg/mL | | | | | | |
| | Median | 1.90 | 124.9 | 0.70* | 42.3 | 0.70* | 47.0 |
| | Range | 0.70*-17.6 | 16.7-466.0* | 0.70*-58.4 | 3.2-466.0† | 0.70*-6.20 | 1.8-466.0† |
| | IL-8, pg/mL | | | | | | |
| | Median | 72.5 | 750.0† | 21.1 | 108.0 | 17.8 | 105.4 |
| | Range | 45.9-371.6 | 428.2-750.0† | 4.6-108.7 | 14.2-750.0† | 10.5-106.2 | 45.6-750.0† |
| | CXCL10, pg/mL | | | | | | |
| | Median | 307.7 | 2000.0† | 217.2 | 2000.0† | 205.7‡ | 2000.0†,‡ |
| | Range | 107.7-331.6 | 2000.0†-2000.0† | 78.0-1034.5 | 487.4-2000.0† | 72.9-475.1 | 277.6-2000.0† |
| | MCP-1, pg/mL | | | | | | |
| | Median | 913.3 | 1500.0† | 554.5 | 1500.0† | 525.6‡ | 1500.0†,‡ |
| | Range | 623.5-1500.0† | 1500.0†-1500.0† | 289.7-1366.7 | 671.2-1500.0† | 318.7-942.1 | 1197.8-1500.0† |
| Effector | Granzyme B, pg/mL | | | | | | |
| | Median | 1.0* | 599.1 | 1.0* | 19.4 | 1.0* | 49.2 |
| | Range | 1.0*-1.0* | 31.4-1.0 × 10⁴† | 1.0*-33.4 | 1.0*-166.1 | 1.0*-65.9 | 1.0*-5477.4 |

Peak serum levels of analytes VCAM-1 and IL-16 were associated with grade≥3 CRS. Such associations were not observed in subjects with ≥3 NE, which may have been due to the small number of patients with ≥3 NE (Table 19).

TABLE 19

Association of serum biomarkers with cytokine release syndrome and neurologic events.

| Function | Peak Value-Median (range) | Cytokine Release Syndrome | | | Neurologic Events | | |
|---|---|---|---|---|---|---|---|
| | | Grade ≥3 (n = 8) | Grade 0-2 (n = 16) | P Value | Grade ≥3 (n = 5) | Grade 0-2 (n = 19) | P Value |
| Homeostat/pro-liferativ | IL-15, pg/mL | 52.4 (13.6-116.9) | 36.4 (6.6-91.1) | 0.3123 | 57.4 (13.6-116.9) | 34.9 (6.6-78.5) | 0.1355 |
| | IL-2, pg/mL | 47.8 (2.1-163.3) | 8.7 (0.9*-690.4) | 0.1112 | 35.3 (2.1-124.0) | 9.0 (0.9*-690.4) | 0.3741 |
| Pro-inflammat. | IL-6, pg/mL | 817.1 (6.7-976.0†) | 71.1 (1.6*-976.0†) | 0.4026 | 976.0† (6.7-976.0†) | 90.8 (1.6*-976.0†) | 0.3137 |
| | CRP, mg/L | 139.4 (5.0-496.0†) | 81.8 (9.2-300.1) | 0.2838 | 129.2 (18.1-496.0†) | 99.5 (5.0-300.1) | 0.6187 |
| | SAA, pg/mL | 5.10 × 10⁸ (3.85 × 10⁶-1.38 × 10⁹†) | 1.01 × 10⁸ (3.48 × 10⁶-1.38 × 10⁹†) | 0.1679 | 1.22 × 10⁹ (1.49 × 10⁷-1.38 × 10⁹†) | 1.61 × 10⁸ (3.48 × 10⁶-1.38 × 10⁹†) | 0.2859 |
| | IL-5, pg/mL | 14.7 (6.3*-26.2) | 6.3* (6.3*-73.7) | 0.4014 | 6.3* (6.3*-42.0) | 6.3* (6.3*-73.7) | 0.7031 |
| | Ferritin, ng/mL | 16,800 (1084.8-2.5 × 10⁴†) | 5921.0 (1116.1-31,600†) | 0.3902 | 10,800 (3046.8-2.5 × 10⁴†) | 6096.1 (1084.8-3.2 × 10⁴†) | 0.6952 |
| | IL-1RA, pg/mL | 1906.6 (395.0-9000.0†) | 2298.7 (91.9-4000.0†) | 0.5193 | 2223.8 (395.0-4000.0†) | 2373.6 (91.9-9000.0†) | 0.9716 |
| | IL-2Rα, ng/mL | 19.6 (3.5-56.3) | 12.7 (2.4-100.0†) | 0.5005 | 18.6 (8.0-34.7) | 13.4 (2.4-100.0†) | 0.5456 |
| | TNF-α, pg/mL | 12.2 (2.8-40.8) | 9.1 (1.7-70.2) | 0.5607 | 12.5 (2.8-40.8) | 9.8 (1.7-70.2) | 0.7223 |
| | ICAM-1, ng/mL | 2758.8 (1398.2-7723.4) | 1516.6 (591.9-7204.9) | 0.0708 | 1611.1 (1347.7-6890.6) | 1717.2 (591.9-7723.4) | 0.8311 |
| | VCAM-1, ng/mL | 2813.8 (1836.7-5101.9) | 1401.9 (807.4-5594.2) | 0.0156 | 1836.7 (963.9-5101.9) | 1883.6 (807.4-5594.2) | 0.6697 |

TABLE 19-continued

Association of serum biomarkers with cytokine release syndrome and neurologic events.

| Function | | Peak Value-Median (range) | Cytokine Release Syndrome | | | Neurologic Events | | |
|---|---|---|---|---|---|---|---|---|
| | | | Grade ≥3 (n = 8) | Grade 0-2 (n = 16) | P Value | Grade ≥3 (n = 5) | Grade 0-2 (n = 19) | P Value |
| Immuno-modulating | GM-CSF, pg/mL | | 52.7 (1.9*-198.0) | 1.9* (1.9*-1500.0†) | 0.2335 | 63.3 (1.9*-100.5) | 1.9* (1.9*-1500.0†) | 0.3312 |
| | IFN-γ, pg/mL | | 1876.0† (42.4-1876.0†) | 720.6 (7.5*-1876.0†) | 0.4041 | 1876.0† (81.2-1876.0†) | 725.7 (7.5*-1876.0†) | 0.3525 |
| | IL-16, pg/mL | | 500.6 (144.7-2502.0) | 213.9 (104.2-3414.2) | 0.0466 | 231.0 (152.6-2502.0) | 265.8 (104.2-3414.2) | 0.8870 |
| Chemokine | IL-10, pg/mL | | 85.8 (6.6-466.0†) | 41.3 (1.8-466.0†) | 0.3421 | 143.4 (9.1-466.0†) | 47.0 (1.8-466.0†) | 0.2550 |
| | IL-8, pg/mL | | 413.0 (14.2-750.0†) | 106.4 (24.3-750.0†) | 0.3709 | 750.0† (45.6-750.0†) | 107.4 (14.2-750.0†) | 0.1236 |
| | CXCL10, pg/mL | | 2000.0† (705.0-2000.0†) | 2000.0† (277.6-2000.0†) | 0.7982 | 2000.0† (1080.4-2000.0†) | 2000.0† (277.6-2000.0†) | 0.5072 |
| | MCP-1, pg/mL | | 1500.0† (823.3-1500.0†) | 1500.0† (671.2-1500.0†) | 1.0000 | 1500.0† (1197.8-1500.0†) | 1500.0† (671.2-1500.0†) | 0.6357 |
| Effector | Granzyme B, pg/mL | | 164.7 (11.5-10,000.0†) | 40.4 (1.0*-5477.4) | 0.0803 | 35.9 (19.4-10,000.0†) | 49.2 (1.0*-5477.4) | 0.6691 |

*Value represents lower limit of quantification in assay used.
†Value represents upper limit of quantification in assay used.
CRP, C-reactive protein; CXCL, C-X-C motif chemokine ligand; GM-CSF, granulocyte-macrophage colony-stimulating factor; IFN-γ, interferon gamma; ICAM, intercellular adhesion molecule; IL, interleukin; IP, interferon γ-induced protein; MCP, monocyte attractant protein; Rα, receptor alpha; RA, receptor antagonist; SAA, serum amyloid A; TNF-α, tumor necrosis factor alpha; VCAM, vascular cell adhesion molecule.

Product characteristics were similar across dose levels (Table 20). Levels of less differentiated CCR7+ T cells in products were higher in patients with CR+CRi and trended higher in MRD-negative patients (Table 21).

TABLE 20

Product characteristics by dose.

| Median characteristic (range) | $2 \times 10^6$ (n = 4) | $2 \times 10^6$, 68 mL (n = 11) | $1 \times 10^6$, 40 mL (n = 9) |
|---|---|---|---|
| T-cell subsets, % | | | |
| Naïve | 32.6 (12.7-67.2) | 53.0 (1.7-93.1) | 38.6 (3.8-75.3) |
| Central memory | 15.4 (10.4-23.2) | 9.1 (3.3-54.2) | 11.9 (1.6-56.7) |
| Effector | 15.7 (4.9-20.1) | 8.6 (1.1-72.0) | 10.4 (1.9-66.1) |
| Effector memory | 36.1 (4.6-57.8) | 10.8 (2.1-74.7) | 14.6 (3.1-61.5) |
| CD4, % | 36.2 (12.4-63.9) | 38.3 (8.3-80.4) | 40.1 (16.5-56.9) |
| CD8, % | 63.9 (35.3-87.6) | 61.7 (19.3-91.7) | 56.6 (43.1-82.8) |
| CD4/CD8 ratio | 0.6 (0.1-1.8) | 0.6 (0.1-4.2) | 0.7 (0.2-1.3) |
| CCR7+, % | 48.0 (23.1-90.4) | 73.8 (17.3-96.6) | 80.2 (6.8-89.4) |
| IFN-γ production in co-culture (pg/mL)* | 4325.0 (2145.0-8299.0) | 5234.0 (42.0-19,500.0) | 7341.0 (2824.0-13,500.0) |
| Transduction, % | 49.9 (31.1-66.5) | 67.7 (33.6-87.8) | 49.0 (32.0-72.0) |
| Viability, % | 90.3 (83.6-95.0) | 91.0 (76.0-97.0) | 91.0 (87.0-94.0) |

*Co-culture experiments were performed using Toledo cells mixed in a 1:1 ratio with KTE-X19 product cells. IFN-γ was measured in cell culture media 24 hours post-incubation using a qualified ELISA. ELISA, enzyme-linked immunosorbent assay; IFN-γ, interferon gamma.

This product profile also appeared to trend with higher levels of neurotoxicity but was not associated with CRS. The ratio of CD4 to CD8 T cells was not associated with response or toxicity.

TABLE 21

Product characteristics by response, MRD status, cytokine release syndrome, and neurologic events.

| Median characteristic (range) | Complete remission (CR + CRi) (n = 16) | No response (n = 8) |
|---|---|---|
| CCR7+, % | 81.0 (9.7-96.6) | 38.0 (6.8-87.4) |
| CD4/CD8 ratio | 0.7 (0.1-1.8) | 0.5 (0.1-4.2) |

| Median characteristic (range) | MRD negative (n = 18) | MRD positive (n = 3) |
|---|---|---|
| CCR7+, % | 81.0 (9.7-96.6) | 18.8 (6.8-82.3) |
| CD4/CD8 ratio | 0.7 (0.1-1.8) | 0.2 (0.1-0.5) |

| Median characteristic (range) | Grade ≥3 CRS (n = 8) | Grade ≤2 CRS (n = 16) |
|---|---|---|
| CCR7+, % | 78.2 (38.7-92.0) | 73.2 (6.8-96.6) |
| CD4/CD8 ratio | 0.7 (0.4-1.8) | 0.6 (0.1-4.2) |

| Median characteristic (range) | Grade ≥3 NE (n = 5) | Grade ≤2 NE (n = 19) |
|---|---|---|
| CCR7+, % | 86.9 (57.2-92.0) | 69.4 (6.8-96.6) |
| CD4/CD8 ratio | 0.7 (0.5-1.6) | 0.6 (0.1-4.2) |

CR, complete remission; CRi, complete remission with incomplete hematologic recovery; CRS, cytokine release syndrome; MRD, minimal residual disease; NE, neurologic event.

In phase 1 of CLINICAL TRIAL-4, no DLTs were observed with KTE-X19 among the DLT-evaluable pediatric or adolescent patients with R/R B-ALL. Although no DLTs were observed at the initial dose of $2 \times 10^6$ CAR T cells/kg, a lower dose of $1 \times 10^6$ CAR T cells/kg with a 68 mL formulation was explored in a second cohort of patients in an effort to further improve the risk:benefit ratio, and dosing and toxicity management were further optimized in a third cohort at $1 \times 10^6$ CAR T cells/kg with a 40 mL formulation and revised toxicity management. This led to a more optimal risk:benefit ratio for the $1 \times 10^6$ CAR T cells/kg (40 mL) dose level with noticeable improvements for CRS and NE. In addition, while MRD-negativity rates were ≥73% for all formulations, rates of MRD negativity and CR alone were highest in patients who received $1 \times 10^6$ CAR T cells/kg (40 mL). After 36.1 months of follow-up in all treated patients, the medians for DOR, RFS, and OS were still not reached in the $1 \times 10^6$ CAR T cells/kg (40 mL) cohort and the 24-month OS rate was 87.5%, potentially suggesting a meaningful durability of response with optimized dosing/formulation of KTE-X19 in pediatric/adolescent patients with R/R B-ALL.

The role of alloSCT following anti-CD19 CAR T-cell therapy in pediatric/adolescent patients with R/R B-ALL is still not well understood; studies in adult populations have provided somewhat conflicting results. (Park J H et al., N Engl J Med 378:449-459, 2018; Hay K A et al., Blood 133:1652-1663, 2019). In the present study, the medians for DOR censored at subsequent alloSCT and OS were not reached in patients treated at the RP2D of $1 \times 10^6$ CAR T cells/kg (40 mL) after 36.1 months median follow-up (median for all treated patients). Fourteen of the 16 patients (88%) who achieved CR+CRi, including 5 treated at the RP2D, received alloSCT as subsequent therapy. AlloSCT was not required per the protocol but was allowed per investigator discretion. Although CLINICAL TRIAL-4 was not designed to assess outcomes after subsequent therapies, given that most responding patients proceeded to alloSCT post-KTE-X19, an evaluation of DOR without censoring for subsequent therapies including alloSCT revealed a favorable median of 14.2 months. Additionally, the median RFS with censoring for subsequent alloSCT was 5.2 months, but was 9.1 months without censoring, indicating a potential favorable impact of alloSCT post-KTE-X19. It has been previously reported that pediatric and young adults with R/R CD19+ ALL who have no history of alloSCT, but who receive consolidative alloSCT following anti-CD19 CAR T-cell therapy, trend toward improved leukemia-free survival with ≥1 year follow-up. (Summers C. et al., Blood 132:967-967, 2018). In a recently published phase I study of anti-CD19 CAR T-cell therapy in children and young adults with R/R B-ALL with 75% of MRD-negative responding patients proceeding to alloSCT, the median OS at 4.8 years follow-up was 70.2 months following alloSCT, the 5-year event-free survival following alloSCT was 61.9%, and the cumulative incidence of relapse following alloSCT was only 9.5%. (Shah N N. et al., Journal of Clinical Oncology 0:JCO.20.02262.) These data suggest that subsequent alloSCT may be important for maintaining remissions following CAR T-cell therapy in pediatric R/R B-ALL. A retrospective review in pediatric and young adult patients found that CD34-selected T-cell depleted alloSCT following CAR T-cell therapy may result in improved transplant-related mortality and OS versus that with unmodified alloSCT. (Fabrizio V A et al., Bone Marrow Transplant 55:2160-2169, 2020.) The median blood CAR T-cell levels in CLINICAL TRIAL-4 were undetectable across all doses at 3 months post-infusion with the median time to alloSCT being 2.3 months, which should consider the association between CAR T-cell persistence and durability of response given the low number of overall patients and the high rate of subsequent alloSCT. In studies with tisagenlecleucel, and in contrast to our study, subsequent alloSCT was performed in a minority of responding patients (12% to 13%) with a short median follow-up of 13.1 months, while approximately 40% of responding patients receiving tisagenlecleucel had already relapsed, mostly with CD19-negative leukemia despite persistent CART cells. (Maude S L et al, N Engl J Med 378:439-448, 2018; Grupp S A et al, Blood 132:895-895, 2018; Pasquini M C et al., Blood Adv 4:5414-5424, 2020).

Figure 12:
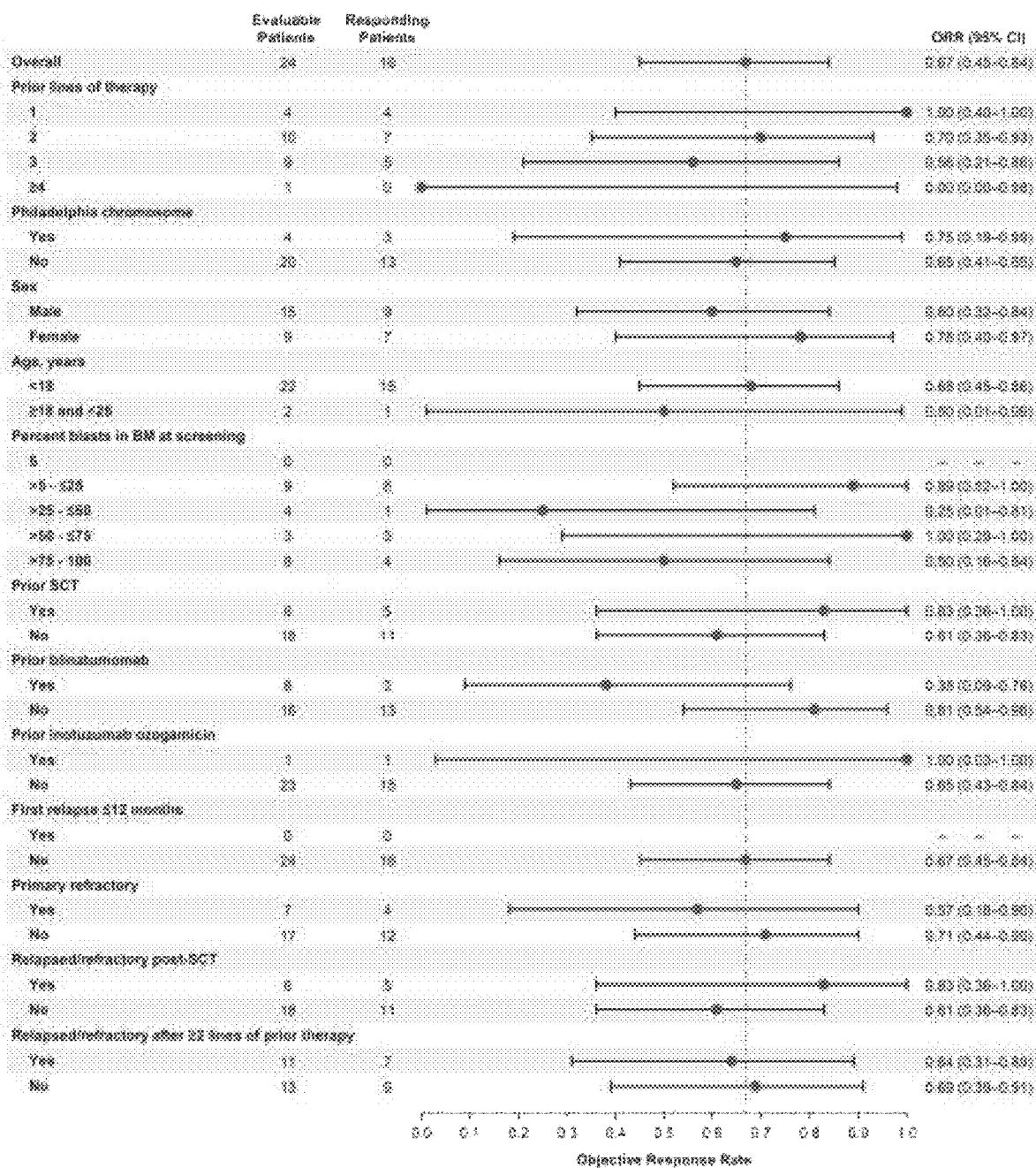
FIG. 12. Subgroup analysis of overall remission rate. BM, bone marrow; ORR, overall remission rate; SCT, stem cell transplant.

While differences in trial designs and patient populations preclude direct trial-to-trial comparisons, recent studies with blinatumomab, which also targets CD19, indicate a median OS of just 7.7 months in pediatric R/R B-ALL, similar to results in adult ALL. (Kantarjian H et al, N Engl J Med 376:836-847, 2017.) Also, for blinatumomab, consolidation with subsequent alloSCT has presented improved outcomes (12-month RFS rate for patients with vs without subsequent alloSCT: 70% vs 30%, respectively). (Locatelli F et al, Blood 136:24-25, 2020.) Additionally, remission rates with blinatumomab are higher among pediatric patients with lower baseline tumor burden (<50% blasts at baseline; 56% CR) vs those with higher tumor burden (≥50% blasts at baseline; 33% CR). (von Stackelberg A et al., J Clin Oncol 34:4381-4389, 2016.) In CLINICAL TRIAL-4, a clear association between remission rates and baseline bone marrow blasts was not apparent, as CR rates were 89%, 25%, 100%, and 50% in patients with >5 to ≤25%, ≥25 to ≤50%, >50 to ≤75%, and >75 to 100% blasts at baseline tumor burden, respectively. However, the small number of patients in each quartile, as well as the relatively high median tumor burden at baseline, limits interpretation (FIG. 12). This is in line with another pediatric and young adult study using CD19-directed CAR T-cell therapy with no difference in response rates based on disease burden. (Gardner R A et al., Blood 129:3322-3331, 2017.) Data from CLINICAL TRIAL-4 suggest that KTE-X19 has the potential to offer more favorable efficacy in patients with high disease burden patients compared to results reported with blinatumomab. There appeared to be an observed trend toward lower CR+CRi rates in patients with prior blinatumomab in CLINICAL TRIAL-4.

The AE profile in CLINICAL TRIAL-4 was consistent with prior studies of anti-CD19 CAR T-cell therapies. For the 24 patients who received KTE-X19, the median time from leukapheresis to delivery to the study site was 16.5 days. In comparison, tisagenlecleucel has a median throughput time of 23 days from receipt of leukapheresed product to delivery to the study site. (Tyagarajan S et al., Mol Ther Methods Clin Dev 16:136-144, 2020.) The rapid turnaround time for treated patients in CLINICAL TRIAL-4 supports the feasibility in the setting of rapidly proliferating ALL. With the RP2D established, CLINICAL TRIAL-4 has transitioned into the phase 2 portion of the study.

The unmet medical need in R/R pediatric ALL is highest for patients who relapse early or have primary refractory disease with a 5-year OS rate of 21% to 28%. (Sun W et al., Leukemia 32:2316-2325, 2018; Crotta A et al., Curr Med Res Opin 34:435-440, 2018; Nguyen K et al., Leukemia 22:2142-50, 2008; Rheingold S R et al., Journal of Clinical Oncology 37:10008-10008, 2019; Oskarsson T et al., Haematologica 101:68-76, 2016; Schrappe M et al., N Engl J Med 366:1371-81, 2012.) In addition, the risk of treatment-related morbidity and mortality is 3-5 times greater in patients who have MRD-positive disease at the end of initial and later lines of therapy than in patients who have undetectable MRD.3 To address this evolving unmet medical need, CLINICAL TRIAL-4 was further amended to broaden the eligibility criteria to include patients with MRD-positive disease as well as patients with early first relapse (≤18 months). Additionally, a second cohort was opened for pediatric patients with R/R NHL (diffuse large B-cell lymphoma, Burkitt's lymphoma, and primary mediastinal B-cell lymphoma).

Example 5

An open-label, global, multicenter, Phase 3 study was conducted to evaluate the safety and efficacy of axicabtagene ciloleucel versus current standard of care for second-line therapy (platinum-based salvage combination chemotherapy regimen followed by high-dose therapy and autologous stem cell transplant in those who respond to salvage chemotherapy) in adult patients with relapsed or refractory Diffuse Large B-Cell Lymphoma (DLBCL). In this study, 359 patients were randomized (1:1) to receive a single infusion of axicabtagene ciloleucel or the current standard of care second-line therapy. The primary endpoint was event-free survival (EFS), defined as the time from randomization to the earliest date of disease progression per Lugano Classification (see Cheson et al, J Clin Oncol. 2014 Sep. 20; 32(27):3059-68), commencement of new lymphoma therapy, or death from any cause. Key secondary endpoints include objective response rate (ORR) and overall survival (OS). Other secondary endpoints include modified event-free survival, progression-free survival (PFS) and duration of response (DOR). Patients enrolled in the study ranged in age from 22 to 81, with 30% of the patients over the age of 65. The study described in this example evaluated a one-time infusion of the cell therapy axicabtagene ciloleucel compared to second-line standard of care (SOC) in adult patients with relapsed or refractory LBCL. The study SOC arm was a 2-step process: following initial relapse, immunochemotherapy was reintroduced and if the patient responded and can tolerate further treatment, then they move on to high-dose chemotherapy plus stem cell transplant.

Key Inclusion Criteria:
1. Histologically proven large B-cell lymphoma including the following types defined by
    WHO 2016 (see Swerdlow et al Blood. 2016 May 19; 127(20):2375-90. doi: 10.1182/blood-2016-01-643569. Epub 2016 Mar. 15. Review.)
    DLBCL not otherwise specified (ABC/GCB)
    HGBL with or without MYC and BCL2 and/or BCL6 rearrangement
    DLBCL arising from FL
    T-cell/histiocyte rich large B-cell lymphoma
    DLBCL associated with chronic inflammation
    Primary cutaneous DLBCL, leg type
    Epstein-Barr virus (EBV)+DLBCL
2. Relapsed or refractory disease after first-line chemo-immunotherapy
    Refractory disease defined as no complete remission to first-line therapy; individuals who are intolerant to first-line therapy are excluded.
    Progressive disease (PD) as best response to first-line therapy
    Stable disease (SD) as best response after at least 4 cycles of first-line therapy (eg, 4 cycles of R-CHOP)
    Partial response (PR) as best response after at least 6 cycles and biopsy-proven residual disease or disease progression≤12 months of therapy
    Relapsed disease defined as complete remission to first-line therapy followed by biopsy-proven relapse≤12 months of first-line therapy
3. Individuals must have received adequate first-line therapy including at a minimum:
    Anti-CD20 monoclonal antibody unless investigator determines that tumor is CD20 negative, and
    An anthracycline containing chemotherapy regimen
4. No known history or suspicion of central nervous system involvement by lymphoma
5. Eastern cooperative oncology group (ECOG) performance status of 0 or 1
6. Adequate bone marrow function as evidenced by:
    Absolute neutrophil count (ANC)≥1000/uL
    Platelet≥75,000/uL
    Absolute lymphocyte count≥100/uL
7. Adequate renal, hepatic, cardiac, and pulmonary function as evidenced by:
    Creatinine clearance (Cockcroft Gault)≥60 mL/min
    Serum Alanine aminotransferase/Aspartate aminotransferase (ALT/AST)≤2.5 Upper limit of normal (ULN)
    Total bilirubin≤1.5 mg/dl
    Cardiac ejection fraction≥50%, no evidence of pericardial effusion as determined by an Echocardiogram (ECHO), and no clinically significant Electrocardiogram (ECG) findings
    No clinically significant pleural effusion
    Baseline oxygen saturation>92% on room air Key Exclusion Criteria were:
1. History of malignancy other than nonmelanoma skin cancer or carcinoma in situ (eg cervix, bladder, breast) unless disease free for at least 3 years
2. Received more than one line of therapy for DLBCL 3. History of autologous or allogeneic stem cell transplant
4. Presence of fungal, bacterial, viral, or other infection that is uncontrolled or requiring intravenous antimicrobials for management.
5. Known history of infection with human immunodeficiency virus (HIV) or hepatitis B (HBsAg positive) or hepatitis C virus (anti-HCV positive). If there is a positive history of treated hepatitis B or hepatitis C, the viral load must be undetectable per quantitative polymerase chain reaction (PCR) and/or nucleic acid testing.
6. Individuals with detectable cerebrospinal fluid malignant cells or known brain metastases, or with a history of cerebrospinal fluid malignant cells or brain metastases.
7. History or presence of non-malignant central nervous system (CNS) disorder such as seizure disorder, cerebrovascular ischemia/hemorrhage, dementia, cerebellar disease, or any autoimmune disease with CNS involvement
8. Presence of any indwelling line or drain. Dedicated central venous access catheter such as a Port-a-Cath or Hickman catheter are permitted.
9. History of myocardial infarction, cardiac angioplasty or stenting, unstable angina, New York Heart Association Class II or greater congestive heart failure, or other clinically significant cardiac diseases within 12 months of enrollment
10. History of symptomatic deep vein thrombosis or pulmonary embolism within 6 months of enrollment
11. History of autoimmune disease, requiring systemic immunosuppression and/or systemic disease modifying agents within the last 2 years
12. History of anti-CD19 or CAR-T therapy or history of prior randomization A primary analysis of the study showed superiority of axicabtagene ciloleucel compared to standard of care (SOC) in second-line relapsed or refractory large B-cell lymphoma (LBCL). The study met the primary endpoint of event free survival (EFS; hazard ratio 0.398, p<0.0001), and the key secondary endpoint of objective response rate (ORR). The interim analysis of overall survival (OS) showed a trend favoring axicabtagene ciloleucel but the data is immature and additional analysis and/or studies may be warranted.

Safety results from the study were consistent with the known safety profile of axicabtagene ciloleucel for the treatment of LBCL in the third-line setting. Six percent of patients experienced CRS grade 3 or higher, and 21% experienced neurological events grade 3 or higher. No new safety concerns were identified in this second-line setting.

T cell phenotype was assessed in axicabtagene ciloleucel products from this study, employing a validated FLOW cytometry method and analyzing know surface markers of T cell differentiation, CCR7 and CD45RA. The metrics were analyzed by Grades of cytokine release syndrome (CRS) and Neurologic events. P values were obtained by Kruskal-Wallis test.

Table 22 shows the total number of infused central memory T cells (CCR7+ CD45RA−) associated with occurrence of Grade>=2 CRS events (compared to Grades 1 and no event), while Table 23 shows the total number of infused effector memory and effector T cells (CCR7−) associated with occurrence of Grade>=3 Neurologic events (compared to Grades 2, 1 and no event). These data uncover that different T Cell Subsets in axicabtagene ciloleucel are differentially associated with toxicity.

TABLE 22

Total number of infused central memory T cells (CCR7+ CD45RA−) associated with occurrence of Grade >= 2 CRS events (compared to Grades 1 and no event) (No. of cells × $10^6$)

| Grade of CRS | No. of cells |
| --- | --- |
| G0/1 CRS | 105.1090714 |
| G0/1 CRS | 44.39781818 |
| G0/1 CRS | 11.60596491 |
| G0/1 CRS | 93.14148148 |
| G0/1 CRS | 40.0555102 |
| G0/1 CRS | 29.86883721 |
| G0/1 CRS | 64.48509804 |
| G0/1 CRS | 24.13728 |
| G0/1 CRS | 36.66526316 |
| G0/1 CRS | 105.3589474 |
| G0/1 CRS | 100.7322034 |
| G0/1 CRS | 69.54385965 |
| G0/1 CRS | 72.03763636 |
| G0/1 CRS | 63.31 |
| G0/1 CRS | 55.233 |
| G0/1 CRS | 37.55630508 |
| G0/1 CRS | 15.52191549 |
| G0/1 CRS | 35.49304348 |
| G0/1 CRS | 9.4646875 |
| G0/1 CRS | 101.1441475 |
| G0/1 CRS | 21.20516129 |
| G0/1 CRS | 59.7279661 |
| G0/1 CRS | 179.0171429 |
| G0/1 CRS | 59.61142857 |
| G0/1 CRS | 117.2214815 |
| G0/1 CRS | 0 |
| G0/1 CRS | 44.681 |
| G0/1 CRS | 21.46720588 |
| G0/1 CRS | 57.22428571 |
| G0/1 CRS | 53.57647059 |
| G0/1 CRS | 26.64675 |
| G0/1 CRS | 23.29811321 |
| G0/1 CRS | 13.2847 |
| G0/1 CRS | 0 |
| G0/1 CRS | 28.45086207 |
| G0/1 CRS | 24.02475 |
| G0/1 CRS | 93.49166667 |
| G0/1 CRS | 36.34605 |
| G0/1 CRS | 55.51101818 |
| G0/1 CRS | 104.4293878 |
| G0/1 CRS | 22.31538462 |
| G0/1 CRS | 30.26928814 |
| G0/1 CRS | 47.64658824 |
| G0/1 CRS | 52.37572131 |
| G0/1 CRS | 24.89569811 |
| G0/1 CRS | 22.4 |
| G0/1 CRS | 10.211625 |
| G0/1 CRS | 26.2695082 |
| G0/1 CRS | 106.6921739 |
| G0/1 CRS | 99.25963636 |
| G0/1 CRS | 52.61556 |
| G0/1 CRS | 131.97552 |
| G0/1 CRS | 23.56614815 |
| G0/1 CRS | 38.9345098 |
| G0/1 CRS | 42.94646154 |
| G0/1 CRS | 11.0416 |
| G0/1 CRS | 68.11234043 |
| G0/1 CRS | 52.997 |
| G0/1 CRS | 46.33659574 |
| G0/1 CRS | 46.26167442 |
| G0/1 CRS | 26.23636364 |
| G0/1 CRS | 173.95 |
| G0/1 CRS | 99.47504348 |
| G0/1 CRS | 42.87966667 |
| G0/1 CRS | 63.51958209 |
| G0/1 CRS | 38.84 |
| G0/1 CRS | 24.15665672 |
| G0/1 CRS | 37.93671429 |
| G0/1 CRS | 56.60745763 |
| G0/1 CRS | 38.44285714 |
| G0/1 CRS | 107.4675 |
| G0/1 CRS | 32.25333333 |
| G0/1 CRS | 84.03316364 |
| G0/1 CRS | 90.02608696 |

TABLE 22-continued

Total number of infused central memory T cells (CCR7+ CD45RA−) associated with occurrence of Grade >= 2 CRS events (compared to Grades 1 and no event) (No. of cells × 10⁶)

| Grade of CRS | No. of cells |
| --- | --- |
| G0/1 CRS | 21.59020408 |
| G0/1 CRS | 149.3085714 |
| G0/1 CRS | 42.345 |
| G0/1 CRS | 23.53391304 |
| G0/1 CRS | 19.16684211 |
| G0/1 CRS | 108.1845797 |
| G0/1 CRS | 16.13410909 |
| G0/1 CRS | 29.07253521 |
| G2+ CRS | 64.70288696 |
| G2+ CRS | 47.67126389 |
| G2+ CRS | 49.89705882 |
| G2+ CRS | 73.5803125 |
| G2+ CRS | 57.39428571 |
| G2+ CRS | 62.20373333 |
| G2+ CRS | 147.2090566 |
| G2+ CRS | 57.61320755 |
| G2+ CRS | 41.8787234 |
| G2+ CRS | 96.82043478 |
| G2+ CRS | 91.324 |
| G2+ CRS | 34.66536585 |
| G2+ CRS | 11.83756364 |
| G2+ CRS | 81.08571429 |
| G2+ CRS | 39.47432143 |
| G2+ CRS | 68.521125 |
| G2+ CRS | 51.26907937 |
| G2+ CRS | 84.41125926 |
| G2+ CRS | 65.30644068 |
| G2+ CRS | 74.8638 |
| G2+ CRS | 31.15601351 |
| G2+ CRS | 51.48457674 |
| G2+ CRS | 69.38697826 |
| G2+ CRS | 102.3616216 |
| G2+ CRS | 66.65454545 |
| G2+ CRS | 63.631 |
| G2+ CRS | 83.748 |
| G2+ CRS | 86.4552 |
| G2+ CRS | 49.14088235 |
| G2+ CRS | 38.9559375 |
| G2+ CRS | 68.7344 |
| G2+ CRS | 72.45356364 |
| G2+ CRS | 55.0386383 |
| G2+ CRS | 50.86759615 |
| G2+ CRS | 47.33752941 |
| G2+ CRS | 25.02073171 |
| G2+ CRS | 48.58530909 |
| G2+ CRS | 51.67795652 |
| G2+ CRS | 38.07707143 |
| G2+ CRS | 57.528 |
| G2+ CRS | 85.11624 |
| G2+ CRS | 22.68664407 |
| G2+ CRS | 41.40792727 |
| G2+ CRS | 74.85 |
| G2+ CRS | 140.0704762 |
| G2+ CRS | 33.39571429 |
| G2+ CRS | 49.50695652 |
| G2+ CRS | 81.20114286 |
| G2+ CRS | 65.856 |
| G2+ CRS | 77.50638806 |
| G2+ CRS | 39.91534615 |
| G2+ CRS | 66.5345625 |
| G2+ CRS | 89.66511628 |
| G2+ CRS | 20.23266667 |
| G2+ CRS | 93.61635556 |
| G2+ CRS | 65.85565574 |
| G2+ CRS | 80.91237931 |
| G2+ CRS | 42.94 |
| G2+ CRS | 53.53225532 |
| G2+ CRS | 32.41942 |
| G2+ CRS | 232.1469388 |
| G2+ CRS | 36.98 |
| G2+ CRS | 18.5059875 |
| G2+ CRS | 43.69334694 |
| G2+ CRS | 34.55847458 |
| G2+ CRS | 56.145 |
| G2+ CRS | 99.41438596 |
| G2+ CRS | 35.10257143 |
| G2+ CRS | 21.6138 |
| G2+ CRS | 34.1048 |
| G2+ CRS | 29.94642857 |
| G2+ CRS | 44.9085 |
| G2+ CRS | 33.306 |
| G2+ CRS | 2.003021212 |
| G2+ CRS | 61.26689655 |
| G2+ CRS | 86.92625 |
| G2+ CRS | 15.96617647 |
| G2+ CRS | 70.55878261 |
| G2+ CRS | 28.21065789 |
| G2+ CRS | 64.00625 |
| G2+ CRS | 48.68237288 |
| G2+ CRS | 44.70967742 |

TABLE 23

Total number of infused effector memory and effector T cells (CCR7−) associated with occurrence of Grade >= 3 Neurologic events (compared to Grades 2, 1 and no event) (No. of cells × 10⁶)

| Grade of NE | No. of cells |
| --- | --- |
| G0/1/2 NE | 100.3846261 |
| G0/1/2 NE | 196.778375 |
| G0/1/2 NE | 153.7058824 |
| G0/1/2 NE | 169.75375 |
| G0/1/2 NE | 119.6286429 |
| G0/1/2 NE | 188.496 |
| G0/1/2 NE | 91.35017544 |
| G0/1/2 NE | 293.4514286 |
| G0/1/2 NE | 133.2696296 |
| G0/1/2 NE | 133.2881633 |
| G0/1/2 NE | 112.8724528 |
| G0/1/2 NE | 58.49313953 |
| G0/1/2 NE | 116.3784314 |
| G0/1/2 NE | 159.8301887 |
| G0/1/2 NE | 177.6772 |
| G0/1/2 NE | 166.5575439 |
| G0/1/2 NE | 139.3279661 |
| G0/1/2 NE | 113.8880727 |
| G0/1/2 NE | 103.751 |
| G0/1/2 NE | 54.88682927 |
| G0/1/2 NE | 186.4514286 |
| G0/1/2 NE | 178.334 |
| G0/1/2 NE | 247.9817818 |
| G0/1/2 NE | 89.39783051 |
| G0/1/2 NE | 128.7988732 |
| G0/1/2 NE | 66.82660714 |
| G0/1/2 NE | 148.2498551 |
| G0/1/2 NE | 39.19640625 |
| G0/1/2 NE | 269.5909375 |
| G0/1/2 NE | 83.78965574 |
| G0/1/2 NE | 80.00129032 |
| G0/1/2 NE | 88.3352381 |
| G0/1/2 NE | 119.5354074 |
| G0/1/2 NE | 172.304 |
| G0/1/2 NE | 161.447619 |
| G0/1/2 NE | 110.979 |
| G0/1/2 NE | 112.5896296 |
| G0/1/2 NE | 192.7483871 |
| G0/1/2 NE | 316.695 |
| G0/1/2 NE | 122.6395946 |
| G0/1/2 NE | 84.76794118 |
| G0/1/2 NE | 228.5482143 |
| G0/1/2 NE | 198.3882353 |
| G0/1/2 NE | 129.3477656 |
| G0/1/2 NE | 88.75471698 |

TABLE 23-continued

Total number of infused effector memory and effector T cells (CCR7−) associated with occurrence of Grade >= 3 Neurologic events (compared to Grades 2, 1 and no event) (No. of cells × $10^6$)

| Grade of NE | No. of cells |
|---|---|
| G0/1/2 NE | 55.79574 |
| G0/1/2 NE | 201.058 |
| G0/1/2 NE | 125.0340517 |
| G0/1/2 NE | 79.22411163 |
| G0/1/2 NE | 75.99194444 |
| G0/1/2 NE | 95.9066087 |
| G0/1/2 NE | 55.05045 |
| G0/1/2 NE | 46.92648649 |
| G0/1/2 NE | 66.96567273 |
| G0/1/2 NE | 474.1133333 |
| G0/1/2 NE | 100.94625 |
| G0/1/2 NE | 100.42104 |
| G0/1/2 NE | 167.2383673 |
| G0/1/2 NE | 122.2883077 |
| G0/1/2 NE | 101.6367647 |
| G0/1/2 NE | 139.1934375 |
| G0/1/2 NE | 94.91893333 |
| G0/1/2 NE | 37.96646809 |
| G0/1/2 NE | 214.7406102 |
| G0/1/2 NE | 84.48194118 |
| G0/1/2 NE | 309.0089412 |
| G0/1/2 NE | 133.8920727 |
| G0/1/2 NE | 34.49645902 |
| G0/1/2 NE | 102.3286415 |
| G0/1/2 NE | 98.41778571 |
| G0/1/2 NE | 210.936 |
| G0/1/2 NE | 131.88 |
| G0/1/2 NE | 116.684835 |
| G0/1/2 NE | 54.16488 |
| G0/1/2 NE | 169.1934426 |
| G0/1/2 NE | 116.4989831 |
| G0/1/2 NE | 120.1266667 |
| G0/1/2 NE | 82.62857143 |
| G0/1/2 NE | 58.6075 |
| G0/1/2 NE | 149.8822857 |
| G0/1/2 NE | 125.0188657 |
| G0/1/2 NE | 80.18196078 |
| G0/1/2 NE | 138.8004444 |
| G0/1/2 NE | 81.1504 |
| G0/1/2 NE | 100.5644444 |
| G0/1/2 NE | 32.61422951 |
| G0/1/2 NE | 167.6457931 |
| G0/1/2 NE | 237.9778723 |
| G0/1/2 NE | 143.514 |
| G0/1/2 NE | 63.36842553 |
| G0/1/2 NE | 314.4156279 |
| G0/1/2 NE | 98.42 |
| G0/1/2 NE | 237.8763636 |
| G0/1/2 NE | 109.7579574 |
| G0/1/2 NE | 80.28702 |
| G0/1/2 NE | 46.06 |
| G0/1/2 NE | 180.2746957 |
| G0/1/2 NE | 85.75933333 |
| G0/1/2 NE | 35.01877551 |
| G0/1/2 NE | 34.572 |
| G0/1/2 NE | 150.2494737 |
| G0/1/2 NE | 83.6265 |
| G0/1/2 NE | 112.914 |
| G0/1/2 NE | 95.14305085 |
| G0/1/2 NE | 47.84105263 |
| G0/1/2 NE | 177.7285714 |
| G0/1/2 NE | 180.7225 |
| G0/1/2 NE | 53.37514286 |
| G0/1/2 NE | 66.26648571 |
| G0/1/2 NE | 167.490375 |
| G0/1/2 NE | 192.9733333 |
| G0/1/2 NE | 94.794 |
| G0/1/2 NE | 147.0580364 |
| G0/1/2 NE | 38.08 |
| G0/1/2 NE | 216.2742857 |
| G0/1/2 NE | 77.94365152 |
| G0/1/2 NE | 124.6627586 |
| G0/1/2 NE | 71.16625 |
| G0/1/2 NE | 114.2982857 |
| G0/1/2 NE | 56.60735294 |
| G0/1/2 NE | 146.0741739 |
| G0/1/2 NE | 134.8701316 |
| G0/1/2 NE | 134.6070833 |
| G0/1/2 NE | 192.5068846 |
| G0/1/2 NE | 126.8145763 |
| G0/1/2 NE | 104.9797101 |
| G0/1/2 NE | 57.2283871 |
| G0/1/2 NE | 42.10421053 |
| G0/1/2 NE | 30.26457971 |
| G0/1/2 NE | 171.9556364 |
| G0/1/2 NE | 55.17186957 |
| G0/1/2 NE | 100.3943662 |
| G0/1/2 NE | 211.5659615 |
| G3+ NE | 176.7537778 |
| G3+ NE | 146.1102128 |
| G3+ NE | 131.0783158 |
| G3+ NE | 48.68070175 |
| G3+ NE | 220.0852174 |
| G3+ NE | 177.7879365 |
| G3+ NE | 106.5877119 |
| G3+ NE | 127.6444068 |
| G3+ NE | 179.36925 |
| G3+ NE | 70.55454545 |
| G3+ NE | 143.8769818 |
| G3+ NE | 100.3750962 |
| G3+ NE | 262.550878 |
| G3+ NE | 151.6158 |
| G3+ NE | 146.8330182 |
| G3+ NE | 85.99787234 |
| G3+ NE | 124.7582609 |
| G3+ NE | 127.3112727 |
| G3+ NE | 188.07264 |
| G3+ NE | 217.68376 |
| G3+ NE | 133.672 |
| G3+ NE | 192.2897407 |
| G3+ NE | 136.1817692 |
| G3+ NE | 194.7298462 |
| G3+ NE | 29.7373125 |
| G3+ NE | 257.127907 |
| G3+ NE | 282.0761125 |
| G3+ NE | 199.6894286 |
| G3+ NE | 127.826597 |
| G3+ NE | 154.7618644 |
| G3+ NE | 156.4692537 |
| G3+ NE | 99.4404 |
| G3+ NE | 266.0357143 |

Example 6

This example presents additional and follow-up results from Example 4 above.

Phase 1 explored two dose levels and formulations; the primary endpoint was the incidence of dose-limiting toxicities (DLTs). Of 31 enrolled patients, KTE-X19 was administered to 24 (median age 13.5 years, range 3-20; median follow-up 36.1 months). No DLTs were observed. All treated patients had grade≥3 adverse events, commonly hypotension (50%) and anemia (42%). Grade 3 cytokine release syndrome rates were 33%, 75%, 27%, and 22% in the all-treated, $2\times10^6$, $1\times10^6$ (68 mL formulation), and $1\times10^6$ (40 mL formulation) CAR T cells/kg groups; 21%, 25%, 27%, and 11% of patients experienced grade≥3 neurologic events, respectively. Overall complete remission (CR) rates (including CR with incomplete hematologic recovery) were 67%, 75%, 64%, and 67% in the all-treated, $2\times10^6$, $1\times10^6$ (68 mL), and $1\times10^6$ (40 mL) CAR T cells/kg groups, respectively. Overall minimal residual disease (MRD)-negativity rates were 100% among responders; 88% of responders underwent subsequent allogeneic stem-cell transplant (alloSCT). In the $1\times10^6$ (40 mL) group (recommended phase 2 dose), median duration of remission censored at alloSCT and median overall survival were not reached. Pediatric/adolescent patients with R/R B-ALL achieved high MRD-negative remission rates with manageable safety after a single dose of KTE-X19. Phase 2 is ongoing at the $1\times10^6$ CAR T cells/kg (40 mL) dose.

Results

Patients

Between 17 Feb. 2016 and 1 Aug. 2018, 31 patients were enrolled and underwent leukapheresis. The median time from leukapheresis to KTE-X19 product release was 14.0 days (range, 9.0¬-20.0) for all treated patients, 16.5 days (range, 12.0-23.0) from leukapheresis to delivery to study site, and 27.0 days (range, 18.0-41.0) from leukapheresis to infusion. Of the 31 enrolled patients, 24 (77%) received conditioning chemotherapy and were subsequently dosed. Seven patients were not dosed due to the following reasons: adverse event (AE; n=1), unsuccessful product manufacture (n=3), ineligible due to AE (n=1), unsuccessful product manufacture and ineligible (n=1), and death (n=1). Twenty-four patients received conditioning chemotherapy followed by KTE-X19; 4 patients received the $2\times10^6$ CAR T cells/kg dose, 11 received the $1\times10^6$ CAR T cells/kg (68 mL) dose formulation, and 9 received the $1\times10^6$ CAR T cells/kg (40 mL) dose formulation. The median follow-up for all treated patients was 36.1 months (range, 24.0-53.9). The median age of treated patients was 13.5 years (range, 3-20); 42% of patients had received ≥3 prior lines of therapy; 29% had primary refractory disease; 25% were R/R after alloSCT; and median bone marrow blasts at screening were 44% (range, 6-99). Prior to enrollment, 6 (25%) patients had undergone prior alloSCT, 8 (33%) received prior blinatumomab, including 3 (13%) who received blinatumomab as the last prior therapy, and 1 (4%) had extramedullary disease. Of the 31 enrolled patients, 30 (97%) received bridging therapy per protocol with new baseline disease assessments performed just prior to lymphodepleting chemotherapy.

Safety

Among the 3 DLT-evaluable patients receiving $2\times10^6$ CAR T cells/kg, no DLTs were observed. All treated patients (n=24) experienced at least one grade≥3 AE, most commonly hypotension (50%) and anemia (42%). Serious AEs of any grade occurred in 71% of patients. Grade≥3 infections occurred in 42% of patients.

CRS was reported in 21 of the 24 treated patients (88%), with 8 (33%) experiencing grade≥3 CRS according to modified Lee grading criteria.33 No grade 4 or grade 5 CRS events occurred. The most common grade≥3 CRS symptoms were hypotension (50%) and pyrexia (25%). Any-grade and grade≥3 hypoxia was observed in 13% and 8% of patients, respectively. The median time to onset of CRS and duration after KTE-X19 infusion was 5 days (range, 1-14) and 7 days (range, respectively, with all events resolved.

Among all treated patients, any-grade NEs were reported in 16 patients (67%), and grade≥3 events occurred in 5 patients (21%), with encephalopathy (13%) being the most common grade≥3 event. One grade 4 fully reversible NE occurred (brain edema) in a patient who received $1\times10^6$ CAR T cells/kg (68 mL); for the management of this event, the patient was treated with dexamethasone, mannitol, sodium chloride, and tocilizumab. There were no grade 5 NEs. Overall, the median time to onset of NEs was 9.5 days (range, 3-60) after infusion, the median time from resolution of first CRS to onset of first NE was 4 days (range, −3 to 52 [first CRS resolved after onset of first NE in 4 patients]), and the median duration of NEs was 8 days. NEs resolved in 14 of 16 patients (88%). The NEs of the remaining two patients were ongoing at the time of death due to an AE (n=1) or progressive disease (n=1). Ten of 16 patients (63%) who experienced NEs had concurrent CRS.

Among all treated patients, 42% received steroids, 63% received tocilizumab, and 46% received vasopressors. Improved overall safety was observed in the 9 patients treated with the $1\times10^6$ CAR T cells/kg (40 mL) dose under revised toxicity management, relative to the 4 patients treated with $2\times10^6$ CAR T cells/kg and the 11 patients treated at $1\times10^6$ CAR T cells/kg (68 mL) under the original guidelines. Of the patients receiving $2\times10^6$ CAR T cells/kg, 75% experienced grade≥3 CRS, compared with 27% and 22% of patients receiving $1\times10^6$ CAR T cells/kg (68 mL and 40 mL, respectively). Grade≥3 NEs were observed in 25% of patients who received $2\times10^6$ CART cells/kg and 27% of patients who received $1\times10^6$ CART cells/kg (68 mL) but were lowest (11%) in patients who received $1\times10^6$ CART cells/kg (40 mL). In addition, the median time to onset of NEs, as well as CRS, appeared to be delayed in the $1\times10^6$ CART cells/kg dose cohorts compared with the $2\times10^6$ CAR T cells/kg dose cohort.

Among the 8 patients (33%) who died on study, 6 died from progressive disease (median 190.5 days post¬¬-KTE-X19 infusion), and 2 patients died from AEs (other than grade 5 B-ALL) considered unrelated to KTE-X19, including disseminated mucormycosis (n=1, day 15 post-KTE-X19 infusion) and *Escherichia* sepsis (n=1, day 409 post-KTE-X19 infusion). Of those who died, 3 patients received $2\times10^6$ CAR T cells/kg, 4 received $1\times10^6$ CAR T cells/kg (68 mL), and 1 received $1\times10^6$ CART cells/kg (40 mL). No patient tested positive for replication competent retrovirus or antibodies to anti-CD19 CAR at any time.

Efficacy

With a median follow-up time of 36.1 months (range, 24.0-53.9), all treated patients (n=24) were evaluable for efficacy. The overall remission rate by investigator assessment was 67%, with 29% of patients (n=7) achieving CR and 38% achieving CRi (n=9). In the $2\times10^6$, $1\times10^6$ (68 mL), and $1\times10^6$ (40 mL) CAR T cells/kg dose groups, the CR+CRi rate was 75%, 64%, and 67%, respectively. The median time from infusion to CR+CRi across dose levels was 30 days (range, 26-113 days). The overall MRD-negativity rate was 100% among the 16 patients with CR+CRi. Sixteen patients overall (67%) received alloSCT as subsequent consolidative therapy, including 2, 8, and 6 patients in the $2\times10^6$, $1\times10^6$ (68 mL), and $1\times10^6$ (40 mL) CAR T cells/kg dose groups, respectively. Fourteen of the 16 patients (88%) who achieved CR+CRi (2, 7, and 5 in the $2\times10^6$, $1\times10^6$ [68 mL], and $1\times10^6$ [40 mL] CAR T cells/kg dose groups, respectively) underwent subsequent alloSCT. Additionally, the patients who achieved CR with partial hematologic recovery (n=1) and blast-free hypoplastic/aplastic bone marrow (n=1) both proceeded to alloSCT; they subsequently achieved CR. The median time to transplant for all treated patients was 2.3 months (range, 1.4-24.9) post-KTE-X19. Of the 2 patients who achieved CR+CRi but did not receive subsequent alloSCT, 1 died due to progressive disease, and 1 was lost to follow-up.

The median DOR for the 16 patients who achieved CR+CRi post-KTE-X19 was 7.2 months (95% CI, 4.1-14.2)

after censoring for subsequent alloSCT, and was 4.1 months, 10.7 months, and not reached in the $2\times10^6$, $1\times10^6$ (68 mL), and $1\times10^6$ (40 mL) CAR T cells/kg dose groups, respectively. The median DOR was 14.2 months (95% CI, 3.9—not estimable) without censoring for subsequent alloSCT and resumption of tyrosine kinase inhibitor. The median DOR among the 14 patients with CR+CRi who received subsequent alloSCT post-KTE-X19 was 10.7 months (95% CI, 7.2-14.2). The median RFS for all treated patients (n=24) was 5.2 months (95% CI, 0.0-17.8). The median RFS for the $1\times10^6$ CAR T cells/kg (40 mL) group was not reached and was 5.2 months (95% CI, 0.0-5.2) and 9.1 months (95% CI, 0.0-17.8) in the $2\times10^6$ and $1\times10^6$ (68 mL) cells/kg cohorts, respectively. The median RFS among the 16 patients who proceeded to subsequent alloSCT was 9.1 months (95% CI, 9.1-17.8). The median OS was not reached among all treated patients and in both $1\times10^6$ CAR T cells/kg dose groups and was 8.0 months for the $2\times10^6$ CAR T cells/kg dose group. The 24-month OS rate was 87.5% (95% CI, 38.7-98.1) for the $1\times10^6$ cells/kg (40 mL) dose and 72.7% (95% CI, 37.1-90.3) for the $1\times10^6$ cells/kg (68 mL) dose. Overall, as of the data cutoff, 8 of 24 treated patients (33%) died, 1 discontinued due to consent withdrawal, and 1 was lost to follow-up. The remaining 14 patients (58%) were still alive and in continued follow-up as of data cutoff, all of whom received subsequent alloSCT after KTE-X19.

Based on the safety and efficacy data analysis, the RP2D was $1\times10^6$ KTE-X19 cells/kg (40 mL formulation) with revised toxicity management.

Translational Analysis

CAR T-cell expansion in peripheral blood measured by polymerase chain reaction (PCR) and expressed as the number of CAR gene copies/μg DNA in blood was observed across dose groups with peak CAR T-cell levels reached by day 14 followed by a subsequent CAR T-cell contraction to baseline. Median CAR T-cell levels were undetectable in blood by PCR across all dose groups at 3 months post-KTE-X19 infusion. Median peak CAR gene copies/μg DNA blood were similar between the $1\times10^6$ CAR T cells/kg dose cohorts but were higher in the $2\times10^6$ CAR T cells/kg cohort. Patients achieving CR+CRi trended toward higher peak blood CAR gene copies/μg DNA in blood than non-responders, as did patients who were MRD negative versus MRD positive. CAR gene copies/μg DNA in blood trended higher in patients who had grade≥3 NEs compared with those who had grade≤2 NEs, while there was no apparent difference in peak CAR gene copies/μg DNA in blood for patients with either high- or low-grade CRS in this limited sample size. The median peak CAR gene copies/μg DNA in blood was $5.16\times10^4$ (range, $0$-$2.40\times10^5$) in the 16 patients who did not have prior blinatumomab, and was $6.15\times10^3$ (range, $0$-$2.49\times10^5$) in the 8 patients who did have prior blinatumomab.

Peak levels of multiple key serum cytokines, chemokines, and proinflammatory biomarkers occurred by day 7. Commensurate with peak CAR expansion, some serum analytes trended higher in patients dosed with $2\times10^6$ compared with $1\times10^6$ CAR T cells/kg (interleukin [IL]-2, IL-5, IL-6, IL-8, IL-10, IL-15, IL-16, ferritin, granzyme B, intercellular adhesion molecule 1 [ICAM-1], interferon gamma [IFN-γ], and tumor necrosis factor alpha [TNF-α].

Peak serum levels of analytes VCAM-1 and IL-16 were associated with grade≥3 CRS. Such associations were not observed in subjects with ≥3 NEs, which may have been due to the small number of patients with ≥3 NEs. Product characteristics were similar across dose levels. Levels of less differentiated CCR7+ T cells in products were higher in patients with CR+CRi and trended higher in MRD-negative patients. This product profile also appeared to trend with higher levels of neurotoxicity but was not associated with CRS. The ratio of CD4 to CD8 T cells was not associated with response or toxicity.

Discussion

In phase 1 of Clinical Trial-4, no DLTs were observed with KTE-X19 among the DLT-evaluable pediatric or adolescent patients with R/R B-ALL. Although no DLTs were observed at the initial dose of $2\times10^6$ CAR T cells/kg, a lower dose of $1\times10^6$ CAR T cells/kg with a 68 mL formulation was explored in a second cohort of patients in an effort to further improve the risk:benefit ratio, and dosing and toxicity management were further optimized in a third cohort at $1\times10^6$ CAR T cells/kg with a 40 mL formulation and revised toxicity management. This led to a more optimal risk:benefit ratio for the $1\times10^6$ CAR T cells/kg (40 mL) dose level with noticeable improvements for CRS and NE. In addition, while MRD-negativity rates were ≥73% for all formulations, rates of MRD negativity and CR alone were highest in patients who received $1\times10^6$ CAR T cells/kg (40 mL). Importantly, the medians for DOR, RFS, and OS were not reached among the 9 patients in the $1\times10^6$ CAR T cells/kg (40 mL) cohort, with most responders (5/6 [83%]) proceeding to subsequent alloSCT. Recognizing the limitations of a small cohort, nevertheless the 24-month OS rate in this group was 87.5%. These results potentially suggest a meaningful durability of response with optimized dosing/formulation of KTE-X19 followed by a subsequent alloSCT in pediatric/adolescent patients with R/R B-ALL.

The role of alloSCT following anti-CD19 CAR T-cell therapy in pediatric/adolescent patients with R/R B-ALL is still not well defined; studies in adult populations have provided somewhat conflicting results. In the present study, the medians for DOR censored at subsequent alloSCT and OS were not reached in patients treated at the RP2D of $1\times10^6$ CAR T cells/kg (40 mL). Fourteen of the 16 patients (88%) who achieved CR+CRi, including 5 treated at the RP2D, received alloSCT as subsequent therapy. AlloSCT was not required per the protocol but was allowed per investigator discretion. Clinical Trial-4 was not designed to assess outcomes after subsequent therapies; however, most responding patients proceeded to alloSCT post-KTE-X19 per investigators' decision.

An evaluation of DOR in Clinical Trial-4 without censoring for subsequent therapies including alloSCT revealed a favorable median of 14.2 months. Additionally, the median RFS with censoring for subsequent alloSCT was 5.2 months, but was 9.1 months without censoring. It has been previously reported that pediatric and young adults with R/R CD19+ ALL who have no history of alloSCT, but who receive consolidative alloSCT following anti-CD19 CAR T-cell therapy, trend toward improved leukemia-free survival with ≥1 year follow-up. In a recently published phase 1 study of anti-CD19 CAR T-cell therapy in children and young adults with R/R B-ALL with 75% of MRD-negative responding patients proceeding to alloSCT, the median OS at 4.8 years follow-up was 70.2 months following alloSCT, the 5-year event-free survival following alloSCT was 61.9%, and the cumulative incidence of relapse following alloSCT was only 9.5%. Interestingly, a retrospective review in pediatric and young adult patients found that CD34-selected T-cell depleted alloSCT following CAR T-cell therapy may result in improved transplant-related mortality and OS versus that with unmodified alloSCT.

Data presented herein support the promising potential role for KTE-X19 in extending response durability and survival in pediatric/adolescent patients with R/R B-ALL, particularly if followed by alloSCT.

While differences in trial designs and patient populations preclude direct trial-to-trial comparisons, recent studies with blinatumomab, which also targets CD19, indicate a median OS of just 7.7 months in pediatric R/R B-ALL, similar to results in adult ALL.40 Also for blinatumomab, consolidation with subsequent alloSCT has shown improved outcomes (70% vs 30% 12-month RFS rate for patients with vs without subsequent alloSCT, respectively). Additionally, remission rates with blinatumomab are higher among pediatric patients with lower baseline tumor burden (<50% blasts; 56% CR) vs those with higher tumor burden (≥50% blasts; 33% CR). In Clinical Trial-4, a clear association between remission rates and baseline bone marrow blasts was not apparent, as CR rates were 89%, 25%, 100%, and 50% in patients with >5 to ≤25%, >25 to ≤50%, >50 to ≤75%, and >75 to 100% blasts at baseline, respectively. This is in line with another pediatric and young adult study using CD19-directed CAR T-cell therapy with no difference in response rates based on disease burden. Data from Clinical Trial-4 suggest that KTE-X19 has the potential to offer more favorable efficacy in patients with high disease burden compared to results reported with blinatumomab. There appeared to be an observed trend toward lower CR+CRi rates in patients with prior blinatumomab in Clinical Trial-4.

The AE profile in Clinical Trial-4 was consistent with prior studies of anti-CD19 CAR T-cell therapies. For the patients who received KTE-X19, the median time from leukapheresis to delivery to study site was 16.5 days. In comparison, for the first 37 commercially manufactured tisagenlecleucel products for patients with B-ALL, the reported median throughput time was 23 days from receipt of leukapheresed product to delivery to clinical site. The rapid turnaround time for treated patients in Clinical Trial-4 supports the feasibility in the setting of rapidly proliferating ALL.

The unmet medical need in R/R pediatric ALL is highest for patients who relapse early or have primary refractory disease with a 5-year OS rate of 21% to 28%. 2, 4, 8, 43-45 In addition, the risk of treatment-related morbidity and mortality is 3-5 times greater in patients who have MRD-positive disease at the end of initial and later lines of therapy than in patients who have undetectable MRD.3.

To address this evolving unmet medical need, Clinical Trial-4 was further amended to broaden the eligibility criteria to include patients with MRD-positive disease and patients with early first relapse (≤18 months). Additionally, a second cohort was opened for pediatric patients with R/R NHL (diffuse large B-cell lymphoma, Burkitt lymphoma, and primary mediastinal B-cell lymphoma). Among US Food and Drug Administration/European Medicines Agency-approved or investigational agents in a registrational trial in pediatric R/R B-ALL, Clinical Trial-4 is the first CAR T-cell therapy trial to report more than 3-years follow-up with positive results.

All publications, patents, patent applications and other documents cited in this application are hereby incorporated by reference in their entireties for all purposes to the same extent as if each individual publication, patent, patent application or other document were individually indicated to be incorporated by reference for all purposes. While various specific embodiments/aspects have been illustrated and described, it will be appreciated that various changes may be made without departing from the spirit and scope of the disclosure.

We claim:

1. A method of treating Relapsed/Refractory B-precursor Acute Lymphoblastic Leukemia in a subject comprising administering to the subject about $1\times10^6$ cells per kg body weight of brexucabtagene autoleucel in a total volume of about 40 ml, wherein the subject is a pediatric or adolescent subject, further comprising preconditioning the subject with fludarabine administered at a dose of about 25 mg/m$^2$ on the fourth, third, and second day before infusion of brexucabtagene autoleucel and with cyclophosphamide administered at a dose of about 900 mg/m$^2$ on the second day before infusion of brexucabtagene autoleucel.

2. The method of claim 1, wherein the brexucabtagene autoleucel is administered as a first, second, third, fourth, fifth, or sixth line of therapy, or prior to disease progression.

3. The method of claim 1, further comprising at least one of administering tocilizumab for management of a neurologic event only in the context of cytokine release syndrome, and administering a corticosteroid for management of a grade 2 neurologic event.

4. The method of claim 1, wherein the subject is at high-risk of disease progression, wherein the subject is at high-risk if the subject shows progression of disease within 24 months after initial diagnosis.

\* \* \* \* \*

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Thr Ser Gly Ser Gly Lys Pro Gly Ser Gly Glu Gly Ser Thr
1               5                   10                  15

Lys Gly

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Gly Ser
1               5
```